(12) United States Patent
Ullman et al.

(10) Patent No.: US 7,635,571 B2
(45) Date of Patent: Dec. 22, 2009

(54) AMPLIFIED SIGNAL IN BINDING ASSAYS

(75) Inventors: Edwin F. Ullman, Atherton, CA (US); Rajendra Singh, San Jose, CA (US); Steve De Keczer, San Jose, CA (US); Dariush Davalian, San Jose, CA (US)

(73) Assignee: Siemens Healthcare Diagnostics Products GmbH, Marburg (DE)

(*) Notice: Subject to any disclaimer, the term of this patent is extended or adjusted under 35 U.S.C. 154(b) by 1321 days.

(21) Appl. No.: 09/732,047

(22) Filed: Dec. 7, 2000

(65) Prior Publication Data

US 2004/0175696 A1   Sep. 9, 2004

(51) Int. Cl.
G01N 33/00   (2006.01)

(52) U.S. Cl. .......... 435/7.94; 435/7.1; 435/7.9; 435/7.92; 435/283.1; 435/287.2; 435/288.3; 435/288.7

(58) Field of Classification Search .......... 435/4, 435/6, 7.1, 7.4, 91.53, 91.2, 7.5, 7.92–7.95; 436/501, 518, 523–534, 164, 172, 905; 536/24.3, 536/24.33, 25.32; 977/711
See application file for complete search history.

(56) References Cited

U.S. PATENT DOCUMENTS

| | | | |
|---|---|---|---|
| 3,679,655 A | 7/1972 | Jager | |
| 3,689,391 A * | 9/1972 | Ullman | 204/157.91 |
| 3,720,622 A * | 3/1973 | Bollyky | 252/700 |
| 4,038,282 A | 7/1977 | Hirschmann et al. | |
| 4,256,834 A | 3/1981 | Zuk et al. | |
| 4,275,149 A | 6/1981 | Litman et al. | |
| 4,279,992 A | 7/1981 | Boguslaski et al. | |
| 4,374,925 A | 2/1983 | Litman et al. | |
| 4,476,051 A | 10/1984 | Fujino et al. | |
| 4,478,817 A | 10/1984 | Campbell et al. | |
| 4,598,044 A | 7/1986 | Kricka et al. | |
| 4,663,278 A | 5/1987 | DiNello | |
| 4,729,950 A | 3/1988 | Kricka et al. | |
| 4,847,240 A | 7/1989 | Ryser et al. | |
| 4,910,300 A | 3/1990 | Urdea et al. | |
| 4,931,223 A * | 6/1990 | Bronstein et al. | 252/700 |
| 5,034,317 A * | 7/1991 | Arnost et al. | 435/18 |
| 5,093,232 A | 3/1992 | Urdea et al. | |
| 5,184,020 A * | 2/1993 | Hearst et al. | 250/455.11 |
| 5,212,287 A | 5/1993 | Tolle et al. | |
| 5,216,141 A | 6/1993 | Benner | |
| 5,237,016 A | 8/1993 | Ghosh et al. | |
| 5,256,575 A | 10/1993 | Hu et al. | |
| 5,258,506 A | 11/1993 | Urdea et al. | |
| 5,332,662 A | 7/1994 | Ullman | |
| 5,340,716 A | 8/1994 | Ullman et al. | |

(Continued)

OTHER PUBLICATIONS

Holtz, K.M. et al. A model of the transition state in the alkaline phosphatase reaction. J. Biol. Chem. 1999;274:8351-8354.*

(Continued)

*Primary Examiner*—Melanie J. Yu
(74) *Attorney, Agent, or Firm*—Theodore J. Leitereg

(57) ABSTRACT

Methods are disclosed for determining minute quantities of an analyte in a medium suspected of containing the analyte. One method comprises treating a medium suspected of containing an analyte under conditions such that the analyte, if present, causes a substrate having an oxidant cleavable linker and a photosensitizer to come into close proximity. The photosensitizer generates singlet oxygen which oxidatively cleaves the linker to form a product which can be detected in a sandwich detection assay such as LOCI. The amount of product detected is related to the amount of analyte in the medium. Compositions, kits, and compounds are also disclosed.

3 Claims, 20 Drawing Sheets

Dig-Linked-Biotin-AnthraceneR-CO₂Me

U.S. PATENT DOCUMENTS

| | | | |
|---|---|---|---|
| 5,357,043 A | 10/1994 | Delahaye et al. | |
| 5,362,866 A | 11/1994 | Arnold, Jr. | |
| 5,384,265 A | 1/1995 | Kidwell et al. | |
| 5,393,877 A | 2/1995 | McLean et al. | |
| 5,445,944 A | 8/1995 | Ullman | |
| 5,474,895 A | 12/1995 | Ishii et al. | |
| 5,478,893 A | 12/1995 | Ghosh et al. | |
| 5,482,867 A | 1/1996 | Barrett et al. | |
| 5,491,063 A | 2/1996 | Fisher et al. | |
| 5,494,793 A | 2/1996 | Schindele et al. | |
| 5,510,270 A | 4/1996 | Fodor et al. | |
| 5,512,659 A | 4/1996 | Ullman et al. | |
| 5,516,636 A | 5/1996 | McCapra | |
| 5,532,138 A | 7/1996 | Singh et al. | |
| 5,534,620 A * | 7/1996 | Oh et al. | 530/413 |
| 5,536,644 A | 7/1996 | Ullman et al. | |
| 5,536,815 A | 7/1996 | Carpino et al. | |
| 5,536,834 A | 7/1996 | Singh et al. | |
| 5,539,097 A | 7/1996 | Arnold, Jr. | |
| 5,547,932 A | 8/1996 | Curiel et al. | |
| 5,574,142 A | 11/1996 | Meyer, Jr. et al. | |
| 5,578,498 A | 11/1996 | Singh et al. | |
| 5,583,211 A | 12/1996 | Coassin et al. | |
| 5,607,924 A | 3/1997 | Magda et al. | |
| 5,616,719 A | 4/1997 | Davalian et al. | |
| 5,618,732 A | 4/1997 | Pease et al. | |
| 5,622,826 A | 4/1997 | Varma | |
| 5,624,803 A | 4/1997 | Noonberg et al. | |
| 5,639,873 A | 6/1997 | Barascut et al. | |
| 5,650,270 A * | 7/1997 | Giese et al. | 435/6 |
| 5,652,099 A | 7/1997 | Conrad | |
| 5,658,751 A | 8/1997 | Yue et al. | |
| 5,672,478 A | 9/1997 | Singh et al. | |
| 5,688,940 A | 11/1997 | Lyttle | |
| 5,705,622 A | 1/1998 | McCapra | |
| 5,709,994 A | 1/1998 | Pease et al. | |
| 5,728,399 A | 3/1998 | Wu et al. | |
| 5,728,525 A | 3/1998 | Conrad | |
| 5,728,527 A | 3/1998 | Singer et al. | |
| 5,756,705 A | 5/1998 | Wang | |
| 5,756,726 A | 5/1998 | Hemmi et al. | |
| 5,763,594 A | 6/1998 | Hiatt et al. | |
| 5,767,267 A | 6/1998 | Glazer et al. | |
| 5,770,367 A | 6/1998 | Southern et al. | |
| 5,770,692 A | 6/1998 | Anteunis et al. | |
| 5,780,646 A | 7/1998 | Singh et al. | |
| 5,807,675 A | 9/1998 | Davalian et al. | |
| 5,811,311 A | 9/1998 | Singh et al. | |
| 5,851,770 A * | 12/1998 | Babon et al. | 435/18 |
| 5,851,778 A * | 12/1998 | Oh et al. | 435/7.9 |
| 6,027,890 A * | 2/2000 | Ness et al. | 435/6 |
| 6,143,514 A * | 11/2000 | Ullman et al. | 435/28 |
| 6,243,980 B1 * | 6/2001 | Bronstein et al. | 435/7.72 |
| 6,287,765 B1 * | 9/2001 | Cubicciotti | 435/6 |
| 6,627,400 B1 * | 9/2003 | Singh et al. | 435/6 |
| 6,770,439 B2 * | 8/2004 | Singh et al. | 435/6 |
| 6,844,166 B1 * | 1/2005 | Wolf | 435/7.93 |
| 2001/0049105 A1 * | 12/2001 | Singh et al. | 435/6 |

OTHER PUBLICATIONS

Smith, K.K. et al. Photodissociation of tetramethyldioxetane. J. Phys. Chem. 1978;82:2291-2293.*

Ullmari et al., *Luminescent oxygen channeling immunoassay: Measurement of particle binding kinetics by chemiluminescence.* Proc. Nat'l Acad. Sci. USA, vol. 91. pp. 5426-5430, Jun. 1994 Biochemistry.

* cited by examiner

14

Dig-Linked-Biotin-AnthraceneR-CO₂Me

Bead Preparation for Nucleic Acid Detection Amplification

16

1 S1AX
2 Oligo

18

19

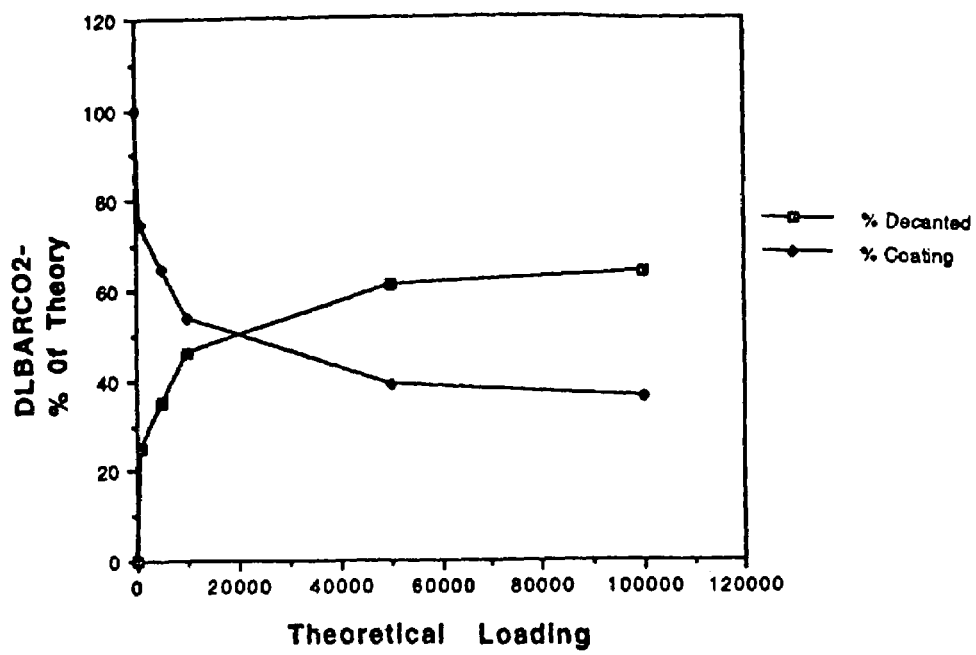
Fig. 6
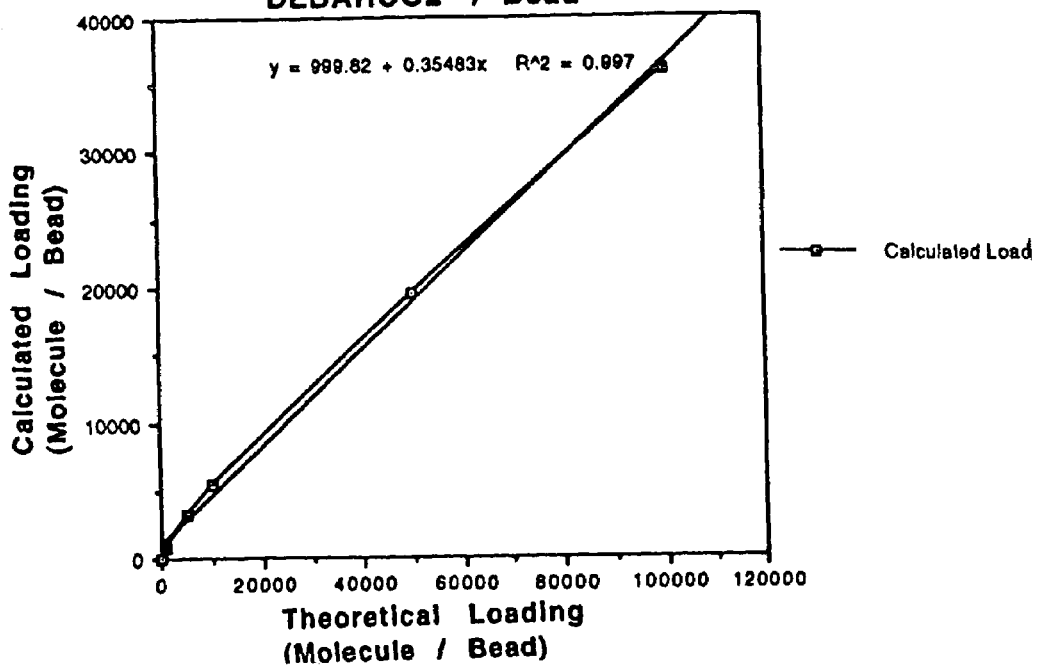

TEST:

Dig-Linked-Biotin Release From DLBAR-Beads

STEP 1

STEP 2

SIGNAL

Procedure:
Combine 100μL (100μg) of each bead, incubate for 1hr at 37⁰. Dilute with 0.8mL IHBB. Remove 100μL for $T_0$ and each $T_n$ illumination (D-J lamp). Add 10μL (10μg) of each bead (for step 2) to each $T_n$ and incubate for 1 hr at 37⁰. Add 1ml LOCI buffer to each, and equilibrate for 1h at 37⁰. Read 1s/1s x 10.

Deprotection of DLBARCO2-BEADS
Detection by LOCI
Sens-SAv and CL-anti-dig

Deprotection of Stressed 050 DLBAR/OLIGO-BEADS
Detection by LOCI
Sens-SAv and CL-anti-dig Preparation of DLBAR/Oligo Beads 20K DLBAR/Bead
20K Oligo/Bead

AMPLIFIED SIGNAL IN BINDING ASSAYS

FIELD OF THE INVENTION

This invention relates to methods, compositions and kits for determining the concentration or presence of an analyte in a sample. In particular, this invention relates to specific binding assays which utilize substrates having oxidant cleavable linkers for enhancing the detection of an analyte by amplifying the signal of a specific binding assay regardless of which detection method is used.

BACKGROUND OF THE INVENTION

Luminescence-based immunoassays such as FOCI and LOCI have proved to be exceptionally sensitive and versatile homogeneous immunoassay techniques capable of detection of materials (analytes) such as nucleic acids, antigens, antibodies, other receptors and small molecules. Although detection in the range of several hundreds of thousand of molecules per milliliter is routinely accessible, it has not been possible to further increase the sensitivity. Nevertheless there remains a need for assays with enhanced sensitivity that can detect as few as 100 molecules per milliliter. Such improved assays would be particularly important in the detection of microbial antigens or nucleic acids which may indicate an infection when as little as one molecule is present. Other applications of the improved assay would include the detection of cytokines and other intercellular messengers that are increasingly implicated as playing a role in disease processes.

In developing an assay there are many considerations. One consideration is the signal response to changes in the concentration of an analyte. A second consideration is the ease with which the protocol for the assay may be carried out. A third consideration is the variation in interference from sample to sample. Ease of preparation and purification of the reagents, availability of equipment, ease of automation and interaction with material of interest are some of the additional considerations in developing a useful assay.

One broad category of techniques involves the use of a receptor which can specifically bind to a particular spacial and polar organization of a labeled ligand as a function of the presence of an analyte. The observed effect of binding by the receptor will depend upon the label. In some instances the binding of the receptor merely provides for a differentiation in molecular weight between bound and unbound labeled ligand. In other instances the binding of the receptor will facilitate separation of bound labeled ligand from free labeled ligand or it may affect the nature of the signal obtained from the label so that the signal varies with the amount of receptor bound to labeled ligand. A further variation is that the receptor is labeled and the ligand unlabeled. Alternatively, both the receptor and ligand are labeled or different receptors are labeled with two different labels, whereupon the labels interact when in close proximity and the amount of ligand present affects the degree to which the labels of the receptor may interact.

In specific binding assays, one molecule, usually the analyte, often serves as a bridge to cause the association of two receptors such as antibodies or DNA probes to form a complex. The complex is detected by having a label attached to at least one of the receptors. The unbound labeled receptor can be physically removed and the remaining label can be measured or the complex can be detected without separation by using a homogeneous immunoassay method. In homogeneous immunoassays involving small molecules, it is unnecessary to separate the bound and unbound label have previously been described for small molecules and thus the assay is conducted in a single or homogenous reaction mixture. These assays include SYVA's FRAT® assay, EMIT® assay, enzyme channeling immunoassay, and fluorescence energy transfer immunoassay (FETI); enzyme inhibitor immunoassays (Hoffmann LaRoche and Abbott Laboratories): fluorescence polarization immunoassay (Dandlicker), among others. All of these methods have limited sensitivity, and only a few including FETI and enzyme channeling, are suitable for large multiepitopic analytes. In contrast to homogeneous immunoassays, heterogeneous immunoassays require a separation step and are generally useful for both small and large molecules. Various labels have been used including enzymes (ELISA), fluorescent labels (FIA), radiolabels (RIA), chemiluminescent labels (CLA), etc.

In both the homogeneous and heterogeneous methods, the signal is limited by the number of labels that can be attached to the receptor and considerable effort has been expended to create structures that have many labels. In LOCI, multiple chemiluminescer molecules are incorporated into latex particles. In enzyme channeling immunoassays, multiple enzymes are attached to a particle. In heterogeneous immunoassays multiple labels are often assembled by creating avidin-biotin complexes. Many biotin molecules are attached to the antibody and avidin that is bound to multiple labels is allowed to bind to the biotin molecules. In the Chiron b-DNA assay, a complex tree-like structure is created by using branched DNA as the receptor. Each of the branches of the DNA then serves as a binder for complementary DNA that is attached to an enzyme. In all of these methods, the signal that is produced is limited by the choice of the particular label. The greatest success has been with enzyme and chemiluminescent labels. See U.S. Pat. Nos. 4,230,797; 4,238,565; 4,279,992; 4,318,981; 4,318,982; 5,710,264; Li et al. "Homogeneous Substrate-labeled Fluorescent Immunoassay for Theophylline ins Serum," Clin. Chem., Vol. 27, pp. 22-26 (1981); and Carrico et al., "Specific Protein-Binding Reactions Monitored with Ligand-ATP Conjugates and Firefly Luciferase," Anal. Biochem., Vol. 76, pp. 95-110 (1976).

Detection of signal depends upon the nature of the label or reporter group. If the label or reporter group is an enzyme, additional members of the signal producing system include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule, the medium can be irradiated and the fluorescence determined. Where the label is a radioactive group, the medium can be counted to determine the radioactive count.

When very low concentrations of analyte must be detected as required for small clinical samples, the current methods are slow and labor intensive, and nonisotopic labels that are less readily detected than radiolabels are frequently not suitable. A method for increasing the sensitivity to permit the use of simple, rapid, nonisotopic, homogeneous or heterogeneous methods for detecting analytes is therefore desirable.

SUMMARY OF THE INVENTION

The present invention provides a method for enhancing the detection of an analyte by amplifying the signal from a binding assay regardless of which detection method is used. This is accomplished by causing the binding reaction to initiate a process that leads to the formation of multiple copies of a product that itself can be detected by any standard sandwich binding assay method. The assay will often be carried out in two stages although it may be possible to combine all reagents at once in some of the homogeneous formats. In the first stage, a sandwich is formed in which one of the receptors of the sandwich has a label and the other receptor of the sandwich has multiple copies of a substrate associated with it, usually on a support or polymer. Instead of detecting the label directly, the label mediates the oxidative cleavage of a linker attaching the substrate to a support and leads to the release of multiple copies of a product from the support or polymer. The mediation process involves the generation of an oxidant by the label either enzymatically or by irradiation and the subsequent oxidative cleavage of the substrate to release the product. The product can then be detected by a second sandwich binding assay using specific binding reagents. For this strategy to be successful, at least one of the specific binding reagents required for the second sandwich assay must not bind to the substrate either because it is incapable of binding or because the substrate has been removed from the product. Thus, usually at least one binding site must be created in the product that was not present in the substrate. Any sandwich assay method can then be used to detect the product. There are a number of embodiments of the invention that involve substrates that are convertible to a detectable product having two binding sites.

In one embodiment of the invention, an oxidant cleavable linker may be used to attach substrate molecules having two binding sites where the substrate is attached to a surface or support. Subsequent to binding of a target molecule or analyte to produce a sandwich comprising both a receptor having the substrate molecules and a receptor having a label wherein the receptors are in close proximity, the label generates an oxidant which cleaves a linker joining the substrate and the support. The resulting detectable product is released from the surface or support and is physically separated from the substrate by centrifugation, decantation, chromatography or the like. The main advantage of this approach is that any suitable oxidatively cleavable link may suffice. However, this embodiment is usually suitable for heterogeneous assays and the sensitivity of the assay will therefore depend strongly on efficiency of the separation of free and bound receptor to which the substrate is bound.

In a second embodiment of the invention, an oxidant cleavable linker may be used to attach to a support a substrate molecule having two binding sites wherein one of the binding sites is at least partially masked and is completely unmasked upon cleavage of the link and formation of the product. Masking, whereby a binding site is unable to bind to its specific binding reagent, can arise simply by virtue of the substrate being bound to a surface. For instance, the substrate may be bound within pores of the support or surface, i.e., an agarose gel, that are too small to accommodate the specific binding reagent. Alternatively, numerous substrate molecules bound to a relatively smooth surface will be unavailable for binding to a specific binding reagent provided that the specific binding reagent is sufficiently bulky, as for example when it is attached to latex particles. Thus, release of the substrate with formation of a first binding site may be accompanied by unmasking of at least some of a second binding site. This embodiment of the invention does not require separation of the product from the substrate and is equally suitable for both heterogeneous and homogeneous assays.

In a third embodiment of the invention, the substrate attached to a support or surface reacts with the oxidant to simultaneously yield a detectable product comprising two binding sites that are linked together in a manner that permits binding of two specific binding reagents. For example, two hapten precursors can be attached to a support or surface by an oxidant cleavable linker and also attached to each other by another chain of atoms that is sufficiently long to allow antibodies to bind to the released haptens once the cleavable link has been severed. This approach would be suitable for homogeneous assays.

In a fourth embodiment of the invention, a substrate attached to a support or surface via an oxidant cleavable linker that reacts with an oxidant to release a product having a chemically reactive group, usually an electrophilic group. This chemically reactive group is designed to react with a chemical-specific binding reagent, which can be a nucleophile such as an amine or sulfhydryl. The product therefore becomes covalently bound to the specific binding reagent. The product also contains a hapten or ligand that was originally present in the substrate or unmasked as a result of the oxidation or subsequent reaction. For example, oxidation of a substrate that contains one haptenic group linked to a support through an oxidizable linker can yield an active ester as the chemically reactive group. The specific binding reagent could then be an amine, which reacts with the ester. If the amine is attached to a label, reaction with the oxidation product not only releases the product from the support or polymer but also binds the product to the label. If the amine is not attached to a label, it can react with the product to produce a new groups, which can serve as a ligand. A labeled receptor for the ligand can then be used in the subsequent detection step. Any assay method that permits detection of a label bound to an antibody can then be used for detection. The fourth strategy likewise allows for homogeneous assays.

A fifth embodiment of the invention relates to a method for the reversible coupling of a ligand or receptor, usually a polynucleotide, to a molecule, support or surface via a singlet oxygen cleavable linker. Ligands or receptors, e.g., oligonucleotide, that are attached to a surface or molecule through a thioether linkage may be detached from the surface or support using singlet oxygen generated from an enzyme reaction or from a photosensitizer that is associated with the surface and that is excited by light to produce singlet oxygen. The method of the present invention allows for the reversible coupling of oligonucleotides onto a support or surface via a thioether linker that is cleavable by singlet oxygen.

A sixth embodiment of the invention relates to a method for the selective protection or masking of biotin and analogues thereof at the ureido nitrogen using a singlet oxygen cleavable group. The inventive method employs a copper catalyzed coupling reaction to couple the ureido nitrogen of biotin with a variety of unsaturated singlet oxygen sensitive compounds such as oxazole and anthracene halides, vinyl halides, and aryl halides. Deprotection or demasking of the biotin may be accomplished in the presence of singlet oxygen which cleaves off the masking linking group. The cleavable group may function as a protective mask to shield biotin in the presence of proteins such as avidin and streptavidin which strongly bind to biotin. Alternatively, the cleavable group may functions simultaneously as a linker to attach biotin to a molecule, support or surface and as a protective mask to shield the biotin in the presence of binding proteins. Singlet oxygen cleavage of the cleavable group simultaneously frees the biotin from the support or surface and unmasks the biotin, allowing the unmasked biotin to bind to an appropriate protein as desired.

In a seventh embodiment of the invention, singlet oxygen activatable indicator precursors are provided for use in FOCI assays such as the ones described in U.S. Pat. Nos. 5,616,719 and 5,807,675. These precursors that are conjugates of a fluorescent compound and a quencher have been developed that are not fluorescent but become fluorescent when they are exposed to singlet oxygen. They have the structure F-Q where F is a fluorescent group that has an emission maximum preferably greater than 300 nm and Q is a group that reacts rapidly and specifically with singlet oxygen. Q quenches the fluorescence of F. Upon reaction with singlet oxygen F-Q is converted to the fluorescent indicator $F-Q_o$ which has at least five times as much fluorescence intensity as F-Q: A special class of F-Q has the structure F-L-Q'. The group Q' is comprised of a quencher Q' and a linker L that joins F to Q'. Q' quenches the fluorescence of F in F-L-Q'. When exposed to singlet oxygen the linker L is cleaved by the singlet oxygen, F and Q' are separated, and the fluorescent indicator, F, becomes fluorescent.

BRIEF DESCRIPTION OF THE DRAWINGS

These and other features, aspects, and advantages of the present invention will become better understood with reference to the following description, appended claims, and accompanying drawings where:

FIG. 6 illustrates (a) the % of theoretical loading of $DLBAR-CO_2$ versus theoretical loading (molecules/bead) for % decanted and % coating; (b) illustrates UV analysis of coating $DLBAR-CO_2$-/bead (Example 2).

DETAILED DESCRIPTION OF THE INVENTION

Figure 1:
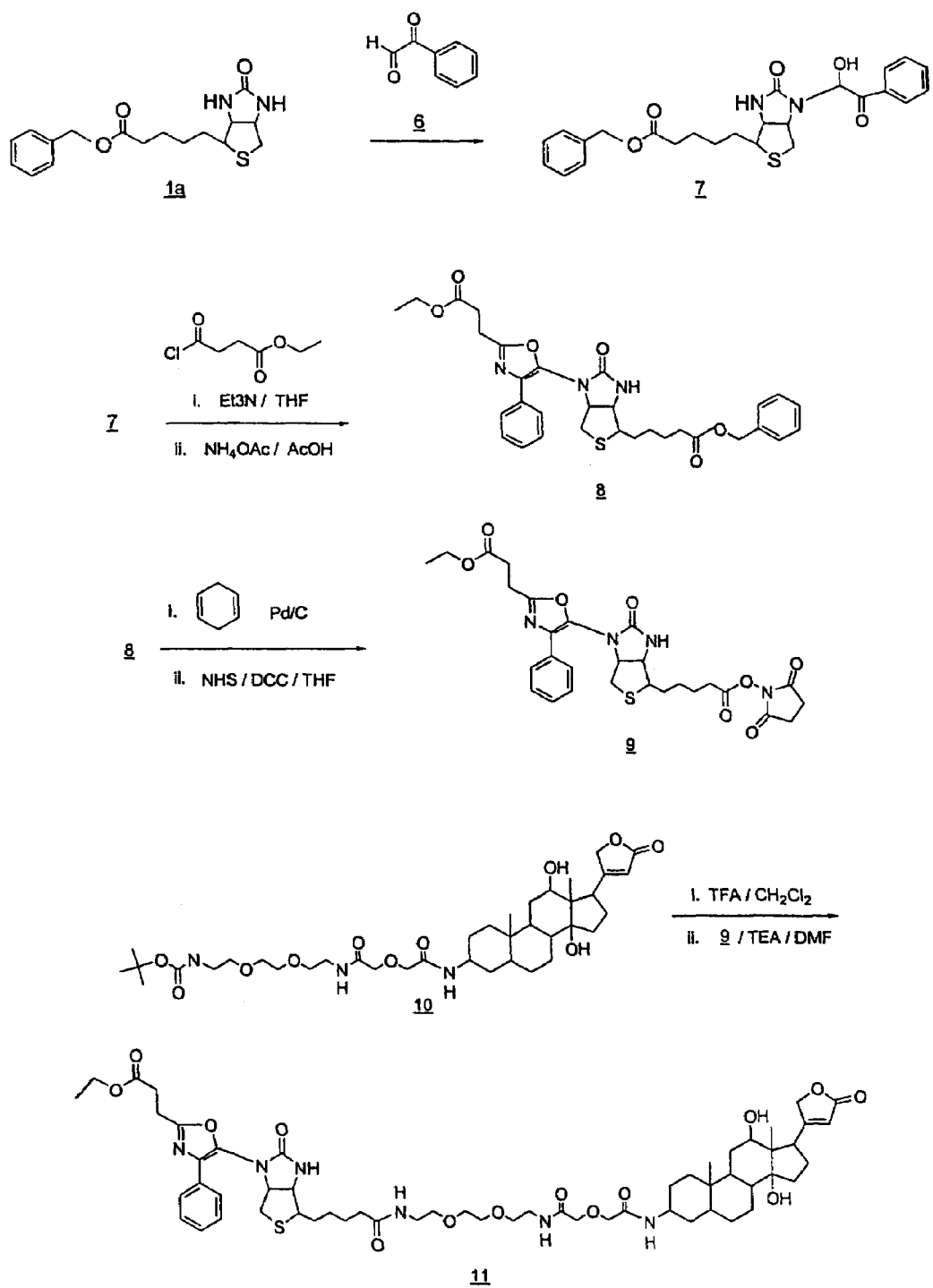
FIG. 1 illustrates the preparation of $DLBOR-CO_2$methyl ester.

The present invention provides a method for enhancing the detection of minute quantities of an analyte or target molecule by amplifying the signal from a binding assay that utilizes a catalyst that is capable of generating an oxidant, e.g., a peroxide or singlet oxygen. This catalyst is generally associated with a support or surface such as a particle to form what is referred herein as a sensitizer particle. The method of the invention entails a first step of forming a sandwich of a first receptor bound to the sensitizer particle, an analyte or target, and a second receptor associated with multiple copies of a substrate. The substrate is attached to a support or surface such as a particle to form what is referred to herein as an acceptor particle. The analyte binds to the first and second receptor, drawing the catalyst and substrate in close proximity. When peroxide or singlet oxygen is generated, an oxidant cleavable linker is cleaved, releasing detectable product. The product includes two binding sites and may be detected using any standard sandwich assay, which utilizes specific binding reagents to form a detectable ternary complex containing the product. In practicing this invention, it is preferred that one of the specific binding reagents be incapable of binding to substrate when it is bound to the acceptor particle which is required for homogenous assays. In addition, it is preferred that the catalyst generate singlet oxygen as the oxidant and that linkers that attach the substrate to the surface or support be singlet oxygen cleavable.

Ligands or receptors, usually a polynucleotide, may be attached to a molecule, support or surface via a singlet oxygen cleavable thioether linker. The thioether linker may be cleaved from the surface or support using singlet oxygen generated from an enzyme reaction or from a photosensitizer that is associated with the surface and that is excited by light to produce singlet oxygen. The thioether linkage is stable even on heating the bound surface to 95° C. or exposing the bound surface to irradiation.

Finally, an active oxygen cleavable linker may also function to mask at least partially an sbp member such as biotin until cleavage occurs. Biotin and analogues thereof may be selectively masked or protected at the ureido nitrogen using a singlet oxygen cleavable group. The inventive method employs a copper catalyzed coupling reaction to couple the ureido nitrogen of biotin with a variety of unsaturated singlet oxygen sensitive compounds such as oxazoles, anthracenes, vinyls, and aryls. Deprotection or demasking of the biotin was accomplished in the presence of singlet oxygen, which cleaves off the masking group. The cleavable group may function as a protective mask to shield biotin in the presence of proteins such as avidin and streptavidin, which strongly bind to biotin. Alternatively, the cleavable group may function simultaneously as a linker to attach biotin to a molecule, support or surface and as a protective mask to shield the biotin in the presence of binding proteins. Singlet oxygen cleavage of the cleavable group simultaneously frees the biotin from the support or surface and unmasks the biotin, allowing the unmasked biotin to bind to an appropriate protein as desired. Before proceeding further with a description of the specific embodiments of the present invention, a number of terms will be defined and described in detail.

Definitions:

In this specification and appended claims, unless specified to the contrary, the terms:

"Analyte" refers to the compound or composition to be detected. The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

The types of proteins, blood clotting factors, protein hormones, antigenic polysaccharides, microorganisms and other pathogens of interest in the present invention are specifically disclosed in U.S. Pat. No. 4,650,770, the disclosure of which is incorporated by reference herein in its entirety.

The monoepitopic ligand analytes will generally be from about 100 to 2,000 molecular weight, more usually from 125 to 1,000 molecular weight.

The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

Other groups of drugs include steroids, which includes the estrogens, androgens, adrenocortical steroids, bile acids, cardiotonic glycosides and aglycones, which includes digoxin and digoxigenin, saponins and sapogenins, their derivatives and metabolites; steroid mimetic substances such as diethylstilbestrol; lactams having from 5 to 6 annular members, which include the barbiturates, e.g., phenobarbital and secobarbital, diphenylhydantoin, primidone, ethosuximide, and their metabolites; aminoalkylbenzenes with alkyl of from 2 to 3 carbon atoms, which includes the amphetamines; catecholamines, which includes ephedrine, L-dopa, epinephrine; narceine; papaverine; and metabolites of the above; benzheterocyclics which include oxazepam, chlorpromazine, tegretol, their derivatives and metabolites, the heterocyclic rings being azepines, diazepines and phenothiazines; purines which include theophylline, caffeine, their metabolites and derivatives; marijuana and its derivatives which includes cannabinol and tetrahydrocannabinol; hormones such as thyroxine, cortisol, triiodothyronine, testosterone, estradiol, estrone, progesterone, polypeptides such as angiotensin, LHRH, and immunosuppressants such as cyclosporin, FK506, mycophenolic acid, rapamycin, and so forth; vitamins such as A, B (e.g., $B_{12}$), C, Q, E and K, folic acid, thiamine; prostaglandins which differ by the degree and sites of hydroxylation and unsaturation; tricyclic antidepressants which include imipramine, dismethylimipramine, amitriptyline, nortriptyline, protriptyline, trimipramine, chlomipramine, doxepine, and desmethyldoxepin; anti-neoplastics which include methotrexate; antibiotics which include penicillin, chloromycetin, actinomycetin, tetracycline, terramycin, the metabolites and derivatives; nucleosides and nucleotides which include ATP, AND, FMN, adenosine, guanosine, thymidine, and cytidine with their appropriate sugar and phosphate substituents; miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives; and aminoglycosides such as gentamicin, kanamycin, tobramycin, and amikacin;

Metabolites related to diseased states include spermine, galactose, phenylpyruvic acid, and porphyrin Type 1.

Among pesticides of interest are polyhalogenated biphenyls, phosphate esters, thiophosphates, carbamates, polyhalogenated sullenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, streptavidin, DNA, RNA, thyroxine binding globulin, thyroxine binding prealbmin, transcortin, etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

"Specific binding pair (sbp) member" refers to one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

"Polynucleotide" refers to a compound or composition which is a polymeric nucleotide having in the natural state about 6 to 500,000 or more nucleotides and having in the isolated state about 6 to 50,000 or more nucleotides, usually about 6 to 20,000 nucleotides, more frequently 6 to 10,000 nucleotides. The term "polynucleotide" also includes oligonucleotides and nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

"Polynucleotide probe" refers to single-stranded nucleic acid molecules having base sequences complementary to that of the target polynucleotide analyte. Probes will generally consist of chemically or synthesized DNA or RNA polynucleotides from 6 to 200 base pair in length and must be capable of forming a stable hybridization complex with the target polynucleotide analyte.

"Ligand" refers to any organic compound for which a receptor naturally exists or can be prepared. The term ligand also includes ligand analogs, which are modified ligands, usually an organic radical or analyte analog, usually of a molecular weight greater than 100, which can compete with the analogous ligand for a receptor, the modification providing means to join the ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

"Receptor" or "antiligand" refers to any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, avidin, protein A, barstar, complement component Clq, and the like. Avidin is intended to include egg white avidin and biotin binding proteins from other sources, such as streptavidin.

"Specific binding" refers to the specific recognition of one of at least two different molecules for the others compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

"Non-specific binding" refers to the non-covalent binding between molecules that is relatively independent of specific surface structures. Non-specific binding may result from several factors including hydrophobic interactions between molecules.

"Antibody" refers to an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

"Label or reporter group or reporter molecule" refers to a member of a signal producing system. Usually the label or reporter group or reporter molecule is conjugated to, i.e., is part of, an oligonucleotide, a nucleoside triphosphate or becomes bound thereto and is capable of being detected directly or, through a specific binding reaction, and can produce a detectible signal. In general, any label that is detectable can be used. The label can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectible group, and the like. Labels include an oligonucleotide or specific polynucleotide sequence that can provide a template for amplification or ligation or act as a ligand such as for a repressor protein. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence (and thus the nucleotide sequence is convertible to a label). The label can be a specific polynucleotide sequence within a nucleotide sequence and thus is comprising a label. When the label is bound to a nucleotide triphosphate it will preferably be small, usually less than 1000 daltons, preferably less than 400 daltons.

"Signal Producing System" refers to a system having one or more components, at least one component being the label or reporter group or reporter molecule. The signal producing system generates a signal that relates to the presence or amount of target, e.g., polynucleotide sequence or a polynucleotide analyte, in a sample. The signal producing system includes all of the reagents required to produce a measurable signal. When the label is not conjugated to a nucleotide sequence, the label is normally bound to an sbp member complementary to an sbp member that is bound to, or part of, a nucleotide sequence. Other components of the signal producing system may be included in a developer solution and can include substrates, enhancers, activators, chemiluminescent and fluorescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination.

The signal-producing system is described more fully in U.S. patent application Ser. No. 07/555,323, now U.S. Pat. No. 5,595,891, filed Jul. 19, 1990, the relevant disclosure of which is incorporated herein by reference.

"Linking group" refers to the covalent linkage between molecules. The linking group will vary depending upon the nature of the molecules, such as a photosensitizer, a singlet-oxygen activatable indicator precursor compound, a sbp member or the molecule associated with or part of a particle, being linked. The linking group comprises functional groups that are normally present or are introduced on a photosensitizer or a singlet-oxygen activatable indicator precursor compound when employed for linking these molecules to an sbp member or to a particle such as a lipophilic component of a liposome or oil droplet, latex particle, silicon particle, metal sol, or dye crystallite.

For the most part, carbonyl functionalities are useful as linking groups, such as oxocarbonyl groups such as aldehydes, acetyl, amides and carboxy groups; and non-oxocarbonyl groups (including nitrogen and sulfur analogs) such as amidine, amidate, thiocarboxy and thionocarboxy. Alternative functionalities of oxo are also useful as linking groups, such as halogen, diazo, mercapto, olefin (particularly activated olefin), amino, phosphoro and the like. A good description of linking groups may be found in U.S. Pat. No. 3,817,837, which disclosure is incorporated herein by reference.

The linking groups may vary from a bond to a chain of from 1 to 100 atoms, usually from about 1 to 70 atoms, preferably 1 to 50 atoms, more preferably 1 to 20 atoms, each independently selected from the group normally consisting of carbon, oxygen, sulfur, nitrogen and phosphorous. The number of heteroatoms in the linking groups will normally range from about 0 to 20, usually from about 1 to 15, more preferably 2 to 6. The atoms in the chain may be substituted with atoms other than hydrogen in a manner similar to that described for organic groups. As a general rule, the length of a particular linking group can be selected arbitrarily to provide for convenience of synthesis, minimize interference of binding sbp members, and permit the attachment of any desired group such as a fluorescent energy acceptor, or a catalyst of inter-system crossing such as a heavy atom, and the like. The linking groups may be aliphatic or aromatic, although with azo groups, aromatic groups will usually be involved.

When heteroatoms are present, oxygen will normally be present as oxo or oxy, bonded to carbon, sulfur, nitrogen or phosphorous; nitrogen will normally be present as nitro, nitroso or amino, normally bonded to carbon, oxygen, or phosphorous; sulfur would be analogous to oxygen; while phosphorous will be bonded to carbon, sulfur, oxygen or nitrogen, usually as phosphonate and phosphate mono- or diester.

Common functionalities which are found in precursors to a conjugate and are used to form a covalent bond between the linking group and the molecule to be conjugated are an alkylating agent (e.g., such as halo or tosylalkyl), alkylamine, amidine, thioamide, ether, urea, thiourea, guanidine, azo, thioether and carboxylate, sulfonate, an active olefin such as a vinyl sulfone, or an $\alpha$, $\beta$-unsaturated ester or amide, and phosphate esters, amides and thioesters.

For the most part, where the photosensitizer and the singlet-oxygen activatable indicator precursor compound of the present invention are linked to a particle, surface or sbp member, the linked product will have a non-oxocarbonyl group (including nitrogen and sulfur analogs), a phosphate group, an amino group, an ether group, a thioether group, an oxocarbonyl group (e.g., aldehyde or ketone). These functionalities will be linked to a particle, surface or a sbp member having functionalities such as amine groups, carboxyl groups, active olefins, or alkylating agents, e.g., bromoacetyl. Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed.

"A group or functionality imparting hydrophilicity or water solubility" refers to a hydrophilic functionality, which increases wettability of solids with water and the solubility in water of compounds to which it is bound. Such a functional group or functionality can be an organic group and can include a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, CO-(glucosamine), sugars, dextran, cyclodextrin, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Most of the above functionalities can also be utilized as attaching groups, which permit attachment of the photosensitizer or singlet-oxygen activatable indicator precursor compound to an sbp member or a support.

"A group or functionality imparting lipophilicity or lipid solubility" is a lipophilic functionality, which decreases the wettability of surfaces by water and the solubility in water of compounds to which it is bound. Such a functional group or functionality can contain 1 to 50 or more atoms, usually carbon atoms substituted with hydrogen or halogen and can include alkyl, alkylidene, aryl and aralkyl. The lipophilic group or functionality will normally have one to six straight or branched chain aliphatic groups of at least 6 carbon atoms, more usually at least 10 carbon atoms, and preferably at least 12 carbon atoms, usually not more than 30 carbon atoms. The aliphatic group may be bonded to rings of from 5 to 6 members, which may be alicyclic, heterocyclic, or aromatic.

"Sensitizer" refers to a molecule which, for the purposes of this invention, can generate a reactive oxygen species, preferably singlet oxygen. Examples of sensitizers include photosensitizers and enzymes. Enzymes which function as sensitizers include haloperoxidases which form singlet oxygen by catalyzing the reaction of a halide-compound, such as a sodium halide, with hydrogen peroxide.

"Photosensitizer" refers to a molecule which, for the purposes of this invention, can be excited to a metastable state, usually a triplet state, which in the proximity of molecular oxygen can directly or indirectly transfer its energy to the oxygen with concomitant excitation of the oxygen to a highly reactive excited state of oxygen often referred to as singlet oxygen or $^1O_2$ ($^1\Delta_g$). The photosensitizer will usually be excited by the absorption of light or by an energy transfer from an excited state of a suitable donor but may also be excited by chemiexcitation, electrochemical activation or by other means. Usually excitation of the photosensitizer will be caused by irradiation with light from an external source. The photosensitizers of this invention will usually have an absorption maximum in the wavelength range of 250-1100 nm, preferably 300-1000 nm, and more preferably 450-950 nm, with an extinction coefficient at its absorbance maximum greater than 500 $M^{-1}cm^{-1}$, preferably at least 5000 $M^{-1}cm^{-1}$, more preferably at least 50,000 $M^{-1}cm^{-1}$. The lifetime of the excited state, usually a triplet state, produced following absorption of light by the photosensitizer will usually be at least 100 nsec, preferably at least 1 nsec in the absence of oxygen. In general, the lifetime must be sufficiently long to permit the energy transfer to oxygen, which will normally be present at concentrations in the range of $10^{-5}$ to $10^{-2}$M (depending on the medium). The excited state of the photosensitizer will usually have a different spin quantum number (S) than its ground state and will usually be in a triplet (S=1) state when, as is usually the case, the ground state is a singlet (S=0). Preferably, the photosensitizer will have a high intersystem crossing yield. That is, excitation of a photosensitizer will produce the long lived state (usually triplet) with an efficiency of at least 10%, desirably at least 40%, preferably greater than 80%. The photosensitizer will usually be at most weakly fluorescent under the assay conditions (quantum yield usually less than 0.5, preferably less that 0.1).

Photosensitizers used in invention are relatively photostable and will not react efficiently with the singlet molecular oxygen so generated. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3-6 of the periodic table, especially iodine or bromine, or they will frequently have polyaromatic structures. Typical photosensitizers include ketones such as benzophenone and 9-thioxanthone; xanthenes such as eosin and rose bengal; polyaromatic compounds such as buckminsterfullerene and 9,10-dibromoanthracene; porphyrins including metalloporphyrins such as hematoporphyrin and chlorophylls; oxazines; cyanines; squarate dyes; phthalocyanines; naphthalocyanines; merocyanines; thiazines such as methylene blue, etc., and derivatives of these compounds substituted by an organic group for enhancing intersystem crossing and rendering such compounds more lipophilic or more hydrophilic and/or as attaching groups for attachment, for example, to an sbp member. Examples of other photosensitizers that may be utilized in the present invention are those that have the above properties and are enumerated in N. J. Turro, "Molecular Photochemistry", page 132, W. A. Benjamin Inc., N.Y. 1965.

The photosensitizers of the instant invention are preferably relatively non-polar to assure dissolution into a lipophilic member when the photosensitizer is incorporated into a suspendible particle such as an oil droplet, liposome, latex particle, and the like.

"Singlet-oxygen activatable indicator precursor compound" refers to molecules that become fluorescent when they react with singlet oxygen. There are several types of reactions of singlet oxygen that can give a fluorescent photoactive indicator compound. The type of reaction that is employed and the choice of the photoactive indicator that is desired provides a guide to the structures of the singlet-oxygen activatable indicator precursor compounds and any auxiliary compounds used in the present invention.

The singlet-oxygen activatable indicator precursor compound will preferably undergo a reaction with singlet oxygen that is very rapid, usually at least $10^4$-$10^6$ $sec^{-1}$, preferably at least $10^6$-$10^8$ $sec^{-1}$, more preferably >$10^8$ $sec^{-1}$. When the initial product of the reaction is an intermediate that reacts to give the photoactive precursor, the intermediate will preferably have a lifetime that is short relative to the desired time between forming singlet oxygen and detecting the fluorescence emitted from the photoactive indicator upon exposure to light. For simultaneous singlet oxygen generation and fluorescence detection the lifetime will usually be <$10^{-3}$-10 sec, preferably <$10^{-3}$ sec. When generation of singlet oxygen and fluorescence detection are sequential the lifetime may vary from $10^{-3}$ sec to 30 minutes or more, preferably <1 sec-60 sec.

Higher rates of reaction of singlet oxygen are achieved by providing singlet oxygen reactive groups in the singlet-oxygen activatable indicator precursor compound that are electron rich. These groups will usually be an olefin or acetylene, hydrazine and hydroxylamine derivatives, selenide and telluride ethers, benzidines, hydroquinones, and aminophenols but are not limited to these groups. For example, telluride ethers have been found to be particularly useful because they react rapidly with singlet oxygen to produce an olefin. The reaction rate depends on the electron availability (oxidation potential) of the tellurium. For example, electron donating groups on an aryl ring substituent on the tellurium atom can increase the rate. Changing from tellurium to selenium (the next lower chalcogenide) will decrease the rate, but increase the oxidation stability of the molecule.

"Photoactive indicator" refers to a molecule which, following excitation emits light by fluorescence. By fluorescence is meant emission of light following excitation by any suitable means including absorption of light, x-rays, electrochemical excitation, chemical excitation, and the like. Alternatively, it may be excited by energy transfer from a donor molecule and it may transfer its excitation energy to an acceptor molecule which thereupon emits light by fluorescence or phosphorescence. Preferably the emission quantum yield will be high, usually at least 0.1, preferably at least 0.4, more preferably greater than 0.7 and the extinction coefficient of the absorption maximum will usually be greater than 5000 $M^{-1}$ $cm^{-1}$. The critical properties of the photoactive indicator are an ability to be electronically excited. The ability of the resultant excited state to be deactivated (quenched), and the ability of the excited state to emit light or induce emission of light from an acceptor.

Photoactive indicators of this invention are typically fluorescent compounds, such as fluorescent brighteners, which typically absorb light between 300 and 600 nanometers and emit between 400 and 800 nanometers; xanthenes such as rhodamine and fluorescein; bimanes; coumarins such as umbelliferone; aromatic amines such as dansyl; squarate dyes; benzofurans; cyanines, merocyanines, rare earth chelates, porphyrins, phthalocyanines, polyaromatic compounds such as pyrene, anthracene, acenaphthene, and the like. Photoactive indicators also include chromenes. Photoactive indicators that can transfer energy to an acceptor molecule will usually absorb at 250 to 550 nm. Such acceptor molecules are luminescent and can include any of the above-mentioned fluorescent and phosphorescent photoactive indicators.

"Measuring the fluorescence" refers to the detection and calculation of the amount of light directly or indirectly emitted from an excited photoactive indicator of the invention. While the fluorescence of the photoactive indicator will usually be measured by exciting the photoactive indicator by irradiation with light and simultaneously detecting the light that is emitted therefrom (i.e., the fluorescence), other methods of detecting the fluorescence are contemplated by this invention. The measurement of fluorescence is intended to include detection of light emitted by the photoactive indicator simultaneous with or immediately following irradiation with light regardless of whether the light is absorbed directly or indirectly or whether the emission is from an excited singlet state or state of higher multiplicity. Measurement of fluorescence is also intended to include the measurement of light emitted from the photoactive indicator following transfer of energy from a donor that is excited through chemiexcitation other than chemiexcitation initiated by absorption of light by the photosensitizer. For example, measurement of fluorescence of the photoactive indicator includes activation of a chemiluminescent molecule, for example, by addition of hydrogen peroxide and peroxidase to luminol, and measurement of the light emitted from the photoactive indicator as a result of the energy transfer from the luminol reaction product to the photoactive indicator.

"Support" or "surface" refers to a surface comprised of porous or non-porous water insoluble material. The surface can have any one of a number of shapes, such as strip, well, rod, particle, including bead, and the like. The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, modified dextran such as the ones described in U.S. Pat. No. 5,929,049, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, lipid vesicles, and cells can also be employed.

Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

The surface will usually be polyfunctional or be capable of being polyfunctionalized or be capable of binding a polynucleotide, an sbp member, a photosensitizer, and/or a photoactive chemiluminescent compound through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well know and is amply illustrated in the literature. See for example Cautrecasas, *J. Biol. Chem.* 245,3059 (1970). The length of a linking group to the oligonucleotide or sbp member may vary widely, depending upon the nature of the compound being linked, the effect of the distance between the compound being linked and the surface on the specific binding properties and the like.

"Suspendible particles" refers to particles capable of being suspended in water which are at least about 20 nm and not more than about 20 microns, usually at least about 40 nm and less than about 10 microns, preferably from about 0.10 to 2.0 microns in diameter, and which normally have a volume of less than about 4 picoliters. The suspendible particles may be organic or inorganic, swellable or non-swellable, porous or non-porous and composed of material that can be transparent, partially transparent, or opaque. The suspendible particles will usually be charged, preferably negatively charged. The suspendible particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or other lipids such as dialkyl phosphates or natural such as cells and organelles). The suspendible particles may be latex particles or other particles comprised of organic or inorganic polymers; lipid vesicles, e.g., liposomes; phospholipid vesicles; oil droplets; silicon particles; metal sols; cells; and dye crystallites.

If organic, the suspendible particles may be polymers, either addition or condensation polymers, which are readily suspendible in the assay medium. The organic suspendible particles will also be adsorptive or functionalizable so as to bind at their surface an sbp member (either directly or indirectly) and to bind at their surface or incorporate within their volume a photosensitizer or a singlet-oxygen activatable indicator precursor compound.

The suspendible particles can be derived from naturally occurring materials, naturally occurring materials which are synthetically modified and synthetic materials. Natural or synthetic assemblies such as lipid bilayers, e.g., liposomes and non-phospholipid vesicles, are preferred. Among organic polymers of particular interest are polysaccharides, particularly cross-linked polysaccharides, such as agarose, which is available as Sepharose, dextran, available as Sephadex and Sephacryl, cellulose, starch, and the like; addition polymers, such as polystyrene, polyacrylamide, homopolymers and copolymers of derivatives of acrylate and methacrylate, particularly esters and amides having free hydroxyl functionalities including hydrogels, and the like. Inorganic polymers include silicones, glasses, available as Bioglas, and the like. Sols include gold, selenium, and other metals. Suspendible particles may also be dispersed water insoluble dyes such as porphyrins, phthalocyanines, etc., which may also act as photosensitizers. Suspendible particles may also include diatoms, cells, viral particles, oil droplets, fat particles such as alkyl triglycerides, magnetosomes, cell nuclei and the like.

Where non-polymeric particles are used, the particle size may be varied by breaking larger particles into smaller particles by mechanical means, such as grinding, sonication, agitation, etc.

Like the surface or support defined above, the suspendible particles will usually be polyfunctional or be capable of being polyfunctionalized or be capable of being bound to an sbp member, photosensitizer, or singlet-oxygen activatable indicator precursor compound through specific or non-specific covalent or non-covalent interactions. A wide variety of functional groups are available or can be incorporated. Exemplary functional groups include carboxylic acids, aldehydes, amino groups, cyano groups, ethylene groups, hydroxyl groups, mercapto groups and the like. When covalent attachment of a sbp member, chemiluminescent compound or photosensitizer to the particle is employed, the manner of linking is well known and is amply illustrated in the literature. See for example Cautrecasas, *J. Biol. Chem.*, 245:3059 (1970). The length of a linking group may vary widely, depending upon the nature of the compound being linked, the nature of the particle, the effect of the distance between the compound being linked and the particle on the binding of sbp members and the analyte and the like.

The photosensitizer and/or singlet-oxygen activatable indicator precursor compound can be chosen to dissolve in, or covalently bind to suspendible particles. When noncovalently bound, the compounds and the particles may be hydrophobic to reduce the ability of the compounds to dissociate from the particles, called leakage. When these compounds are bound to the surface of a particle, they will preferably be bound covalently. When either one or both of the compounds are covalently bound to particles each compound may be either hydrophilic or hydrophobic.

The number of photosensitizer or singlet-oxygen activatable indicator precursor compound molecules associated with each particle will be at least one and may be sufficiently high enough so that the particle consists entirely of photosensitizer or singlet-oxygen activatable indicator precursor compound molecules. The preferred number of molecules will be selected empirically to provide the highest signal. In general, the more molecules the more photoactive indicator molecules can potentially be formed, but this must be balanced by a reduction in the fluorescence efficiency. Normally, the concentration of photosensitizer and singlet-oxygen activatable indicator precursor compound in the particles will range from $10^{-8}$ to 5M, usually from $10^{-5}$ to 0.5 M, preferably from $10^{-3}$ to 0.5 M. Similar concentrations of the singlet oxygen activatable indicator precursor compound will be preferred when the compound is incorporated into non-particulate materials.

"Oil droplets" refers to fluid or waxy particles comprised of a lipophilic compound coated and stabilized with an emulsifier that is an amphiphilic molecule such as, for example, phospholipids, sphingomyelin, albumin and the like.

The phospholipids are based upon aliphatic carboxylic acid esters of aliphatic polyols, where at least one hydroxylic group is substituted with a carboxylic acid ester of from about 8 to 36, more usually of from about 10 to 20 carbon atom, which may have from 0 to 3, more usually from 0 to 1 site of ethylenic unsaturation and at least 1, normally only 1, hydroxyl group substituted with phosphate to form a phosphate ester. The phosphate group may be further substituted with small aliphatic compounds which are of di or higher functionality, generally having hydroxyl or amino groups.

The oil droplets can be made in accordance with conventional procedures by combining the appropriate lipophilic compounds with a surfactant, anionic, cationic or nonionic, where the surfactant is present in from about 0.1 to 40, more usually from about 0.1 to 20 weight percent of the mixture and subjecting the mixture in an aqueous medium to agitation, such as sonication or vortexing. Illustrative lipophilic compounds include hydrocarbon oils, halocarbons including fluorocarbons, alkyl phthalates, trialkyl phosphates, triglycerides, etc.

An sbp member will usually be adsorbed to the surface of the oil droplet or bonded directly or indirectly to a surface component of the oil droplet. The sbp member may be incorporated into the liquid particles either during or after the preparation of the liquid particles. The sbp member will normally be present in from about 0.5 to 100, more usually 1 to 90, frequently from about 5 to 80 and preferably from about 50 to 100 mole percent of the molecules present on the surface of the particle.

The following is a list, by way of illustration and not limitation, of amphiphilic compounds, which may be utilized for stabilizing oil droplets: phosphatidyl ethanolamine, phosphatidyl choline, phosphatidyl serine, dimyristoylphosphatidyl choline, egg phosphatidyl choline, diapalmitoylphosphatidyl choline, phosphatidic acid, cardiolipin, lecithin, galactocerebroside, sphingomyelin, dicetylphosphate, phosphatidyl inositol, 2-trihexadecylammoniumethylamine, 1,3-bis(octadecyl phosphate)-propanol, stearoyloxyethylene phosphate, phospholipids, dialkylphosphates, sodium dodecyl sulfate, cationic detergents, anionic detergents, proteins such as albumin, non-ionic detergents, etc.

Stabilization of oil droplets can also be achieved by coating with a polymer such as polycyanoacrylates, dextran, polymerized proteins such as albumin, hydroxybutyl methacrylate, polyacrylamide and the like.

Other compounds may also be used which have lipophilic groups and which have been described previously. For the most part, these compounds will be alkylbenzenes, having alkyl groups of from 6 to 20 carbon atoms, usually mixtures of alkyl groups, which may be straight or branched chain, and having a carboxyl group, an hydroxylic group, a polyoxy alkylene group (alkylene of from 2 to 3 carbon atoms), carboxylic group, sulfonic acid group, or amino group. Aliphatic fatty acids may be used which will normally be of from about 10 to 36, more usually of from about 12 to 20 carbon atoms. Also, fatty alcohols having the carbon limits indicated for the fatty acids, fatty amines of similar carbon limitations and various steroids may also find use.

The oil droplets can comprise a fluorocarbon oil or a silicone oil (silicon particle). Such droplets are described by Giaever in U.S. Pat. Nos. 4,634,681 and 4,619,904 (the disclosures of which are incorporated herein in their entirety). These droplets are formed by dispersing a fluorocarbon oil or silicone oil in an aqueous phase. The droplets are prepared by placing a small amount of the selected oil (generally, such oils are commercially available) in a container with a larger amount of the aqueous phase. The liquid system is subjected to agitation to bring about emulsification and then centrifuged. The homogeneous phase is removed and the residual droplets are resuspended in an aqueous buffered medium. The above centrifugation and decantation steps can be repeated one or more times before the droplets are utilized.

Sbp members can be bound to the droplets in a number of ways. As described by Giaever (U.S. Pat. Nos. 4,634,681 and 4,619,904), the particular sbp member, particularly a proteinaceous sbp member, can be coated on the droplets by introducing an excess of the sbp member into the aqueous medium prior to or after the emulsification step. Washing steps are desirable to remove excess sbp member. Functionalization of the oil introduces functionalities described above for linking to sbp members. Such functionalities can also be employed to link the droplets to a photosensitizer or a singlet-oxygen activatable indicator precursor compound. On the other hand, the photosensitizer or singlet-oxygen activatable indicator precursor compound will frequently be chosen to be soluble in the oil phase of the oil droplet and will not be covalently bound. When the oil is a fluorocarbon, a fluorinated photosensitizer or singlet-oxygen activatable indicator precursor compound will often be more soluble than the corresponding unfluorinated derivation.

"Liposomes" refers to microvesicles of approximately spherical shape and are one of the preferred materials for use in the present invention. The liposomes have a diameter that is at least about 20 nm and not more than about 20 microns, usually at least about 40 nm and less than about 10 microns. Preferably, the diameter of the liposomes will be less than about two microns so as to limit settling or floatation.

The outer shell of a liposome consists of an amphiphilic bilayer that encloses a volume of water or an aqueous solution. Liposomes with more than one bilayer are referred to as multilamellar vesicles. Liposomes with only one bilayer are called unilamellar vesicles. Multilamellar vesicles are preferred in the present invention when using a lipophilic photosensitizer or singlet-oxygen activatable indicator precursor compound because of their ability to incorporate larger quantities of these materials than unilamellar vesicles. The amphiphilic bilayer is frequently comprised of phospholipids. Phospholipids employed in preparing particles utilizable in the present invention can be any phospholipid or phospholipid mixture found in natural membranes including lecithin, or synthetic glyceryl phosphate diesters of saturated or unsaturated 12-carbon to 24-carbon linear fatty acids wherein the phosphate can be present as a monoester, or as an ester of a polar alcohol such as ethanolamine, choline, inositol, serine, glycerol and the like. Particularly preferred phospholipids include L-α-palmitoyl oleoyl-phosphatidylcholine (POPC), palmitoyl oleoylphosphatidyl-glycerol (POPG), L-α-dioleoylphosphatidylglycerol, L-α-(dioleoyl)-phosphatidyl ethanolamine (DOPE) and L-α-(dioleoyl)-phosphatidyl α-(4-(N-maleimidomethyl)-cyclohexane-1-carboxyamido) ethanol (DOPE-MCC).

The phospholipids in the bilayer may be supplemented with cholesterol and may be replaced with other amphiphilic compounds that have a polar head group, usually charged, and hydrophobic portion usually comprised of two linear hydrocarbon chains. Examples of such substituents include dialkylphosphate, dialkoxypropylphosphates wherein the alkyl groups have linear chains of 12-20 carbon atoms, N-(2, 3-di(9-(Z)-octadecenyloxy))-prop-1-yl-N,N,N-trimethylammonium chloride (DOTMA), sphingomyelin, cardiolipin, and the like.

Liposomes utilized in the present invention preferably have a high negative charge density to stabilize the suspension and to prevent spontaneous aggregation.

Liposomes may be produced by a variety of methods including hydration and mechanical dispersion of dried phospholipid or phospholipid substitute in an aqueous solution. Liposomes prepared in this manner have a variety of dimensions, compositions and behaviors. One method of reducing the heterogeneity and inconsistency of behavior of mechanically dispersed liposomes is by sonication. Such a method decreases the average liposome size. Alternatively, extrusion is usable as a final step during the production of the liposomes. U.S. Pat. No. 4,529,561 discloses a method of extruding liposomes under pressure through a uniform pore-size membrane to improve size uniformity.

For use in the present invention the liposomes should be capable of binding to an sbp member and be capable of having a photosensitizer or singlet-oxygen activatable indicator precursor compound associated with either the aqueous or the nonaqueous phase. The liposomes utilized in the present invention will usually have sbp members bound to the outer surface of the lipid vesicle.

Preparation of liposomes containing a hydrophobic or amphiphilic photosensitizer or a singlet-oxygen activatable indicator precursor compound dissolved in the lipid bilayer can be carried out in a variety of methods, including a method described by Olsen, et al., *Biochemica et Biophysica Acta*, 557(9), 1979. Briefly, a mixture of lipids containing the appropriate compound in an organic solvent such as chloroform is dried to a thin film on the walls of a glass vessel. The lipid film is hydrated in an appropriate buffer by shaking or vortexing. Thereafter, the lipid suspension is extruded through a series of polycarbonate filter membranes having successively smaller pore sizes, for example, 2.0, 1.0, 0.8, 0.6, 0.4, and 0.2 microns. Repeated filtration through any of the filters, and in particular through the smallest filter, is desirable. The liposomes can be purified by, for example, gel filtration, such as through a column of Sephacryl S-1000. The column can be eluted with buffer and the liposomes collected. Storage in the cold prolongs shelf-life of the liposomes produced by this method. Alternatively, the photosensitizer or singlet-oxygen activatable indicator precursor compound can be added to the liquid suspension following preparation of the liposomes.

Labeling of droplets and liposomes will often involve, for example, inclusion of thiol or maleimide or biotin groups on the molecules comprising the lipid bilayer. Photosensitizers, singlet-oxygen activatable indicator precursor compound molecules or sbp members may then be bound to the surface by reaction of the particles with one of these materials that is bound to a sulfhydryl reactive reagent, a sulfhydryl group, or avidin, respectively. Sulfhydryl reactive groups include alkylating reagents such as haloacetamide and maleimide.

Sbp members can be attracted to the surface of the liposome particles by weak hydrophobic interactions, however such interactions are not generally sufficient to withstand the shear force encountered during incubation and washing. It is preferable to covalently bond sbp members to a liposome particle that has been functionalized, for example by use of DOPE-MCC, as shown above, by combining said liposome with the selected sbp member functionalized with a mercaptan group. For example, if the sbp member is an antibody, it may be reacted with S-acetyl-mercaptosuccinic anhydride (SAMSA) and hydrolyzed to provide a sulfhydryl modified antibody.

"Latex particles" refers to a particulate water-suspendible water-insoluble polymeric material usually having particle dimensions of 20 nm to 40000 nm, more preferably 100 to 1000 nm in diameter. The latex is frequently a substituted polyethylene such as the following: polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, and the like. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

The association of the photosensitizer or singlet-oxygen activatable indicator precursor compound with latex particles utilized in the present invention may involve incorporation during formation of the particles by polymerization but will usually involve incorporation into preformed particles, usually by noncovalent dissolution into the particles. Usually, a solution of the singlet-oxygen activatable indicator precursor compound or photosensitizer will be employed. Solvents that may be utilized include alcohols (including ethanol), ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like, and water. The use of solvents having high boiling points in which the particles are insoluble permits the use of elevated temperatures to facilitate dissolution of the compounds into the particles and are particularly suitable. The solvents may be used singly or in combination. Particularly preferred solvents for incorporating a photosensitizer are those that will not quench the triplet excited state of the photosensitizer either because of their intrinsic properties or because they can subsequently be removed from the particles by virtue of their ability to be dissolved in a solvent such as water that is insoluble in the particles. Aromatic solvents are preferred, and generally solvents that are soluble in the particle. For incorporating singlet-oxygen activatable indicator precursor compounds in particles a solvent should be selected that does not interfere with the fluorescence of the photoactive indicator so formed because of their intrinsic properties or ability to be removed from the particles. Frequently, aromatic solvents will also be preferred. Typical aromatic solvents include dibutylphthalate, benzonitrile, naphthonitrile, dioctylterephthalate, dichlorobenzene, diphenylether, dimethoxybenzene, etc.

Except when the photosensitizer or singlet-oxygen activatable indicator precursor compound is to be covalently bound to the surface of the particles, it will usually be preferable to use electronically neutral photosensitizers or singlet-oxygen activatable indicator precursor compounds. It is preferable that the liquid medium selected does not soften the polymer beads to the point of stickiness. A preferred technique comprises suspending the selected latex particles in a liquid medium in which the photosensitizer or singlet-oxygen activatable indicator precursor compound has at least limited solubility. Preferably, the concentrations of the photosensitizer and singlet-oxygen activatable indicator precursor compound in the liquid media will be selected to provide particles that have the highest efficiency of singlet oxygen formation and highest quantum yield of emission from the photoactive indicator so formed in the media but less concentrated solutions will sometimes be preferred. Distortion or dissolution of the particles in the solvent can be prevented by adding a miscible cosolvent in which the particles are insoluble.

Generally, the temperature employed during the procedure will be chosen to maximize the singlet oxygen formation ability of the photosensitizer-labeled particles and the quantum yield of the photoactive indicator so formed from the singlet-oxygen activatable indicator precursor compound-labelled particles with the proviso in that the particles should not become aggregated at the selected temperature. Elevated temperatures are normally employed. The temperatures for the procedure will generally range from 20° C. to 200° C., more usually from 50° C. to 170° C. It has been observed that some compounds that are nearly insoluble in water at room temperature, are soluble in, for example, low molecular weight alcohols, such as ethanol and ethylene glycol and the like, at elevated temperatures. Carboxylated modified latex particles have been shown to tolerate low molecular weight alcohols at such temperatures.

An sbp member may be physically adsorbed on the surface of the latex particle or may be covalently bonded to the particle. In cases wherein the sbp member is only weakly bound to the surface of the latex particle, the binding may in certain cases be unable to endure particle-to-particle shear forces encountered during incubation and washings. Therefore, it is usually preferable to covalently bond sbp members to the latex particles under conditions that will minimize adsorption. This may be accomplished by chemically activating the surface of the latex. For example, the N-hydroxysuccinimide ester of surface carboxyl groups can be formed and the activated particles are then contacted with a linker having amino groups that will react with the ester groups or directly with an sbp member that has an amino group. The linker will usually be selected to reduce nonspecific binding of assay components to the particle surface and will preferably provide suitable functionality for both attachment to the latex particle and attachment of the sbp member. Suitable materials include maleimidated aminodextran (MAD), polylysine, aminosaccharides, and the like. MAD can be prepared as described by Hubert, et al., *Proc. Natl. Acad. Sci.*, 75(7), 3143, 1978.

In one method, MAD is first attached to carboxyl-containing latex particles using a water soluble carbodiimide, for example, 1-(3-dimethylaminopropyl)-3-ethyl carbodiimide. The coated particles are then equilibrated in reagents to prevent nonspecific binding. Such reagents include proteins such as bovine gamma globulin (BGG), and detergent, such as Tween 20, TRITON X-100 and the like. A sbp member having a sulfhydryl group, or suitably modified to introduce a sulfhydryl group, is then added to a suspension of the particles, whereupon a covalent bond is formed between the sbp member and the MAD on the particles. Any excess unreacted sbp member can then be removed by washing.

"Metal sols" refers to those suspendible particles comprised of a heavy metal, i.e., a metal of atomic number greater than 20 such as a Group IB metal, e.g., gold or silver.

Metal sol particles are described, for example, by Leuvering in U.S. Pat. No. 4,313,734, the disclosure of which is incorporated herein by reference in its entirety. Such sols include colloidal aqueous dispersion of a metal, metal compound, or polymer nuclei coated with a metal or metal compound.

The metal sols may be of metals or metal compounds, such as metal oxides, metal hydroxides and metal salts or of polymer nuclei coated with metals or metal compounds. Examples of such metals are platinum, gold, silver, mercury, lead, palladium, and copper, and of such metal compounds are silver iodide, silver bromide, copper hydrous oxide, iron oxide, iron hydroxide or hydrous oxide, aluminum hydroxide or hydrous oxide, chromium hydroxide or hydrous oxide, vanadium oxide, arsenic sulphide, manganese hydroxide, lead sulphide, mercury sulphide, barium sulphate and titanium dioxide. In general, the metals or metal compounds useful may be readily demonstrated by means of known techniques.

It is sometimes advantageous to use sols comprised of dispersed particles consisting of polymer nuclei coated with the above mentioned metals or metal compounds. These particles have similar properties as the dispersed phase of pure metals or metal compounds, but size, density and metal contact can be optimally combined.

The metal sol particles may be prepared in a large number of ways which are in themselves known. For example, for the preparation of a gold sol Leuvering refers to an article by G. Frens in *Nature Physical Science* 241, 20 (1973).

The metal sol particles can be modified to contain various functional groups as described above for linking to an sbp member or a photosensitizer or a singlet-oxygen activatable indicator precursor compound. For example, polymeric bonding agents can be used to coat the particles such as polymers containing thiol groups that bond strongly to many heavy metals or silylating agents that can bond and form polymeric coatings as, for example, by reaction of metal particles with trialkoxy aminoalkylsilanes as described in European Published Patent Application 84400952.2 by Advanced Magnetics for coating magnetic particles.

One method for preparing dye crystallites is described in U.S. Pat. No. 4,373,932 (Gribnau, et al.), the disclosure of which is incorporated herein by reference in its entirety. Gribnau describes colloidal dye particles and aqueous dispersions of a hydrophobic dye or pigment, which may have an immunochemically reactive component directly or indirectly attached. The dye particles are prepared in general by dispersing a dye in water and then centrifuging. A dye pellet is obtained and resuspended in water, to which glass beads are added. This suspension is rolled for several days at room temperature. The liquid is decanted and centrifuged, and the dye particles are obtained after aspiration of the liquid.

Another method for preparing dye crystallites is by slow addition of a solution of the dye in a water miscible solvent to water. Another method is by sonication of a suspension of the solid dye in water.

Binding of sbp members to the dye particles can be achieved by direct or indirect adsorption or covalent chemical attachment. The latter is governed by the presence of suitable functional groups in any coating material and in the dye. For example, functional groups can. be introduced onto the surface of a dye crystalline by coupling a compound containing a diazotized aromatic amino group and the desired functional group to a phenolic or anilino group of the dye.

Where the dye has a carboxyl group, the dye crystallite can be activated by a carbodiimide and coupled to a primary amino component. Aliphatic primary amino groups and hydroxyl groups can be activated, for example, by cyanogen bromide or halogen-substituted di- or tri-azines, after which attachment with a primary amino component or, for example, with a component containing a —SH or —OH group can take place. Use can also be made of bifunctional reactive compounds. For example, glutaraldehyde can be used for the mutual coupling of primary amino components of the dye and an sbp member, and, for example, a hetero-bifunctional reagent such as N-succinimidyl 3-(2-pyridyldithio) propionate can be employed for the coupling of a primary amino component to a component containing a thiol group.

"Wholly or partially sequentially" refers to the condition when the components of the methods of the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

DETAILED DESCRIPTION OF THE PREFERRED EMBODIMENTS

The present invention is directed to a method for enhancing the detection of an analyte by amplifying the signal from a binding assay regardless of which detection method is used. This is accomplished by causing the binding reaction to initiate a process that ultimately leads to the formation of multiple copies of a product that itself can be detected by any standard sandwich binding assay method. The assay will often be carried out in two stages although it may be possible to combine all reagents at once in some of the homogeneous formats. In the first stage, a sandwich is formed in which one of the receptors has a label and the second receptor has multiple copies of a substrate associated with it, usually on a support or polymer. Instead of detecting the label directly, the label mediates the reaction of the substrate that leads to the release of multiple copies of a product from the support or polymer. The mediation process involves the generation of oxidant by the label either enzymatically or by irradiation and the subsequent cleavage of the substrate to release product. The product can then be detected by a second sandwich binding assay. For this strategy to be successful, at least one of the specific binding reagents required for the sandwich assay must not bind to the substrate either because it is incapable of binding or because the substrate has been removed from the product. Thus usually at least one functional group must be created in the product that was not present in the substrate. Any sandwich assay method can then be used to detect the product.

The label is a catalyst capable of forming an oxidant, usually singlet oxygen or hydrogen peroxide. While certain enzymes and electron transfer catalysts are useful, photosensitizers that generate singlet oxygen upon absorption of light are preferred because of the high efficiency of formation and the specificity of the reactions of singlet oxygen. Enzymes that generate singlet oxygen include peroxidases such as lactoperoxidase and chloroperoxidase. Enzymes that generate hydrogen peroxide include most oxidases. Electron transfer catalysts such as Meldola blue can act like oxidases to form hydrogen peroxide.

A number of groups can be used in the cleavable link of the substrate that will react with singlet oxygen with release of the product. Oxazoles, as exemplified above, are particularly attractive because they are quite stable. Reaction with singlet oxygen yields an active ester which will spontaneously hydrolyze or react with an added nucleophilic compound. The reactions lead to the release of groups attached to the oxazole. See, for instance, Wasserman et al. (1992), *Tetrahedron Lett.*, Vol. 33 (47), pp. 7207-7210. Similarly 2,3-disubstituted dioxenes, thioxenes, oxazines, thiazines, dithienes and anthracenes react with singlet oxygen to produce diesters that can hydrolyze or react with an added nucleophile. Singlet oxygen also reacts with diacylhydrazides to form azodicarbonyl compounds that spontaneously hydrolyze or react with nucleophiles, and reaction of singlet oxygen with olefins such as N-methyl-9-benzalacridan leads to rupture of the double bond linking the benzal group to the acridan. Any of these groups can be used as part of the link of the substrate to the polymer or support.

Cleavable linking groups susceptible to hydrogen peroxide cleavage are more limited. See, for instance, U.S. Pat. No. 5,258,506 describing photolabile cleavable sites into polynucleotide chains. Hydrogen peroxides oxidize disulfides to thiosulfonic esters which spontaneously hydrolyze and alkylborons are cleaved to give alkanols. For a description of reversible immobilization of thiol biomolecules based on solid phase bound thiosulfonate groups, see Batista-Viera et al. (1991) *Appl. Biochem. Biotechnol.*, Vol. 31(2), pp. 175-195. Additionally hydrogen peroxide can be used together with a peroxidase to cleave p-hydroxy and p-aminophenyl ethers, reactions which are strongly catalyzed by benzidines such as dicarboxidine. Thus these groups can likewise form a part of the cleavable link of the substrate to the support or polymer. See, for instance, U.S. Pat. No. 5,332,662 which is incorporated by reference in its entirety.

Another aspect of the present invention allows for the reversible coupling of oligonucleotides onto a support or surface via a thioether linker that is cleavable by singlet oxygen. By reacting oligonucleotides labeled with sulfhydryl groups with a surface labeled with alpha iodoacetamide, the oligonucleotides may be attached to the support in high coupling efficiencies and yields. The thioether linkage is stable even on heating the bound surface to 95° C. or exposing the bound surface to irradiation. Exposing the surface to singlet oxygen releases the oligonucleotides from the surface or support by selective cleavage of the thioether linkage. In practicing the invention, singlet oxygen can be generated by a variety of sources including an enzyme reaction or activation of photosensitizer, preferably a photosensitizer. The bound oligonucleotide may be removed from the surface by singlet oxygen cleavage of the linker.

Coupling of aminooligonucleotides to active esters and acids is an inefficient process because the negative charge of the oligonucleotide makes it difficult to deprotonate an attached ammonium group at a pH that is practical for coupling. Activation of a carboxyl group attached to an oligonucleotide is also difficult because of this negative charge environment. Reductive alkylation of an oligonucleotide amine to carboxaldehydes could be carried out successfully, but the reaction occurs in competition with coupling of the amines of the bases to the aldehyde. The integrity of the oligonucleotides was therefore compromised. On the other hand sulfhydryl groups attached to oligonucleotides were known to react efficiently with alpha, beta-unsaturated amides and alpha-haloamides. See U.S. Pat. Nos. 4,775,619; 4,891,324; 5,663,242; 5,237,016; 5,478,893; EP 0275 139 A2; and E. F. Ullman et al., *Proc. Natl. Acad. Sci. USA* (1994), Vol. 91, pp. 5426-5430 describing the coupling of sulfhydryl oligonucleotides with maleimide-containing particles. Of these reactants, only the alpha-haloamide product was expected to be stable at high temperature. The reaction of sulfhydryl oligonucleotides with support particles labeled with alpha-iodoacetamides was therefore exploited to achieve the required coupling efficiencies and stability. Without being bound by any theory of operation for this invention, it is believed that the thioether-carbon bond is cleaved by reaction with singlet oxygen because intact oligonucleotide appears to be released and because the cleavage can be blocked by first reacting the thioether with hydrogen peroxide, presumably oxidizing the thioether to sulfoxide or sulfone. See Ishiguro et al. *J. Am. Chem. Soc.*, Vol. 118, pp. 7265-7271 (1996) and E. J. Corey et al., Tetrahedron Lett. 1976, p. 4263.

Unexpectedly, when oligonucleotides having a sulfhydryl group were coupled to a support or surface, e.g., LOCI sensitizer particles, the coupling can be reversed upon cleavage of the thioether linker with singlet oxygen. The method of the invention can be extended to gene therapy of cells that are capable of endocytosis of particles (for example monocytes). After endocytosis, the cells would be irradiated to release a new gene from the particle. The method of the invention may also be useful in diagnostics. For example, a biotinylated oligonucleotide having a thioether linkage could be bound reversibly to a streptavidin surface. This would provide a method for separation and specific release. For example a DNA probe attached to a surface through a thioether linker could bind a target nucleic acid to which a second labeled probe was bound. After washing away as much non-specifically bound labeled probe as possible, the particles could be irradiated to selectively release the probe:target:lableled probe complex via singlet oxygen cleavage.

Sulfhydryl groups may be introduced to a ligand or target such as oligonucleotides by a variety of ways. For a review of sulfhydrylation reactions, see U.S. Pat. No. 5,663,242 and references cited therein. The sulfhydrylated ligand or target is then attached to any suitable molecule, support or surface. See for instance, E. F. Ullman et al., *Proc. Natl. Acad. Science USA*, Vol. 92, 1994, pp.5426-5430.

Yet another aspect of the invention relates to a method for the selective protection or masking of biotin and analogues thereof at the ureido nitrogen using an singlet oxygen cleavable group. The inventive method employs a copper catalyzed coupling reaction to couple the ureido nitrogen of biotin with a variety of unsaturated singlet oxygen sensitive compounds such as oxazole and anthracene halides, vinyl halides, and aryl halides. Deprotection or demasking of the biotin was accomplished in the presence of singlet oxygen which cleaves off the masking group. The cleavable group may function as a protective mask to shield biotin in the presence of proteins such as avidin and streptavidin which strongly bind to biotin. Alternatively, the cleavable group may functions simultaneously as a linker to attach biotin to a molecule, support or surface and as a protective mask to shield the biotin in the presence of binding proteins. Singlet oxygen cleavage of the cleavable group simultaneously frees the biotin from the support or surface and unmasks the biotin, allowing the unmasked biotin to bind to an appropriate protein as desired.

To date, copper couplings of biotin ureido nitrogens have not been previously reported. For a review of copper coupling reactions, see Renger B., Synthesis-Stuttgart (9), 856-860 (1985); Aalten, H., et al., Tetrahedron Vol. 45. No. 17. pp. 5565-5578, 1989; Suzuki, H., et. al., Chem. Lett., pp. 1443-1446, 1991; Bacon, R., J. Chem. Soc. (C), pp. 312-315, 1969. Attempts to use palladium coupling reaction has failed, resulting in debromination of a bromooxazole derivative.

The coupling reaction for the selective coupling of singlet oxygen cleavable groups to the ureido nitrogen of biotin is generally conducted in solution and typically requires the presence of copper and a base. The inventive method of the invention is illustrated by the reaction below.

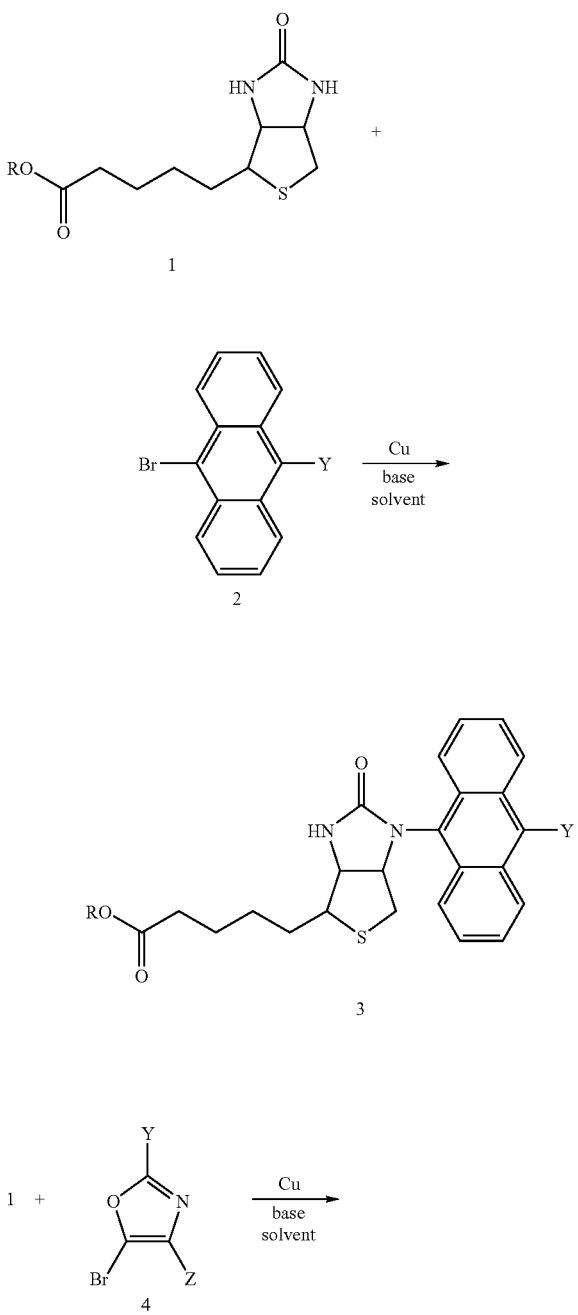

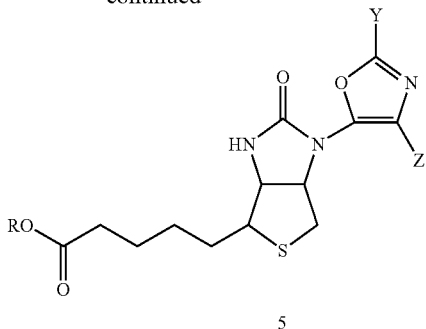

5

Biotin (1) (R=H) may be present in unsubstituted or substituted form. For instance, the R group at the carboxyl terminus may represent H—, Me-, Benzyl, and Me₃SiEt. The singlet oxygen cleavable linkers may be prepared from unsaturated compounds such as anthracenes, vinyls, naphthalens, and aromatic heterocycles such as oxazoles, thiazines and oxazines. These unsaturated compounds may be substituted or unsubstituted. The halide derivatives, e g., bromides, of these singlet oxygen cleavable groups are used in the actual coupling reaction. In practicing this invention, anthracene (2) and oxazoles (4) are the preferred compounds used as the singlet oxygen cleavable linkers where substitution at Y in 2 and 3 represents —OCH₂CH₂OH, —OCH₂CH₂O-Ts, or—OCH₂CH₂SCH₂CO₂-tBu; Y in 4 and 5 represents substituted or unsubstituted alkyl or phenyl such as Ph, PhCO₂Me and —CH₂CH₂CO₂Et; and Z in 4 and 5 represents -Ph.

The ratio of unsaturated compound to biotin generally ranges between about 3 and about 0.5 per mole of biotin, preferably about one mole of unsaturated compound per mole of biotin.

In conducting the coupling reaction, copper metal powder is typically used as catalyst. However, it is envisioned that since the copper 0, 1, and 2 oxidation states equilibrate, other copper compounds such as CuCl₂ and CuI with greater solubility or surface area are contemplated for use in this system. In practicing the invention, elemental copper and copper halides such as copper iodide (using collidine as base) were found to be particularly useful. The amount of copper compound employed generally ranges from between about 8.0 and about 1.0, preferably about 1.0 mole copper compound per mole of biotin.

The coupling reaction may be conducted with a wide variety of bases and solvents. Examples of suitable, non-limiting, examples of bases include KOAc, RbOAc, CsOAc, K₂CO₃, CaCO₃ collidine, and NaH. In practicing this invention, KOAc and K2CO3 are preferred. The amount of base generally ranges between about 50 and about 0.8, preferably about 1 to 1.2 moles of base per mole of biotin.

Non-limiting examples of suitable solvents include DMF, xylene, benzene, THF, and DME. DMF is the preferred solvent for use in this invention.

The temperature of the coupling reaction may range from about 90 to about 180, preferably about 100° C. and about 150° C. The reaction is generally conducted for several hours until the reaction reaches completion as determined by conventional methods including thin layer chromatography.

In another aspect of the invention, singlet oxygen activatable indicator precursors that are conjugates of a fluorescent compound and a quencher have been developed that are not fluorescent but become fluorescent when they are exposed to singlet oxygen. They have the structure F-Q where F is a fluorescent group that has an emission maximum preferably greater than 300 nm and Q is a group that reacts rapidly and specifically with singlet oxygen. Q quenches the fluorescence of F. Upon reaction with singlet oxygen F-Q is converted to the fluorescent indicator F-Q$_o$ which has at least five times as much fluorescence intensity as F-Q:

A special class of F-Q has the structure F-L-Q'. The group Q' is comprised of a quencher Q' and a linker L that joins F to Q'. Q' quenches the fluorescence of F in F-L-Q'. When exposed to singlet oxygen the linker L is cleaved by the singlet oxygen, F and Q' are separated, and the fluorescent indicator, F, becomes fluorescent:

F can be selected from a wide variety of fluorophores such as fluorescein, rhodamine, amino-coumarins, umbelliferones, oxazines, Texas red, acridones, perylenes, indacines such as 4,4-difluoro-4-bora-3a,4a-diaza-s-indacene (BODIPY)(Molecular Probes, Eugene, Oreg.), variants of BODIPY (Molecular Probes, Eugene, Oreg.), (9,10-bisphenylethynylanthracene, squaraine dyes. These fluorophores are for example only. Many other fluorophores which are known in the art could be used with this invention. Typically, fluorophores selected for the present invention are capable of being induced to fluoresce by light at wavelengths of around 400 nm to 600 nm, preferably around 400 nm. Since singlet oxygen is preferably generated by photoexcitation of a photosensitizer the fluorophores will usually be selected to not absorb substantially at the wavelengths chosen to excite the photosensitizer. However F's with longer wavelength absorption will sometimes be practical because quenching by Q inhibits the ability of the fluorescer to act as a photosensitizer. By contrast where Q is able to act as a photosensitizer it must not absorb substantially at the excitation wavelength. Q may quench F by energy transfer from excited F but usually this will not be desirable because an energy accepting quencher would have to absorb at a longer wavelength than F and would be more likely to absorb at the excitation wavelength of the photosensitizer. Instead, Q will usually be selected to quench F by photoelectron transfer which only requires that Q be able to accept or donate an electron to F when F is excited by light. Usually Q will be a good electron donor. However when F is anionic, good electron acceptors can also be used for Q. Thus Q may comprise donors such as aliphatic or aromatic amines, phosphines, hydroquinones, phenolates, polyalkoxyaromatic compounds, hydrazines, hydroxylamines, or other electron donors known in the art. Alternatively Q may be an electron acceptor such as a quinone, β-diketone, polycyano or polynitro aromatic compounds, phthalimide, or other electron acceptors known in the art.

L is a singlet oxygen cleavable linking group such as a hydrazide or substituted phenols, substituted acetylene with a tertiary amine, enol ether, enol thioether, enamine, or thioether.

Typical groups that can serve as linkers and their reactions with singlet oxygen include:

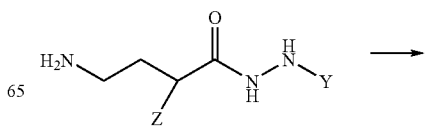

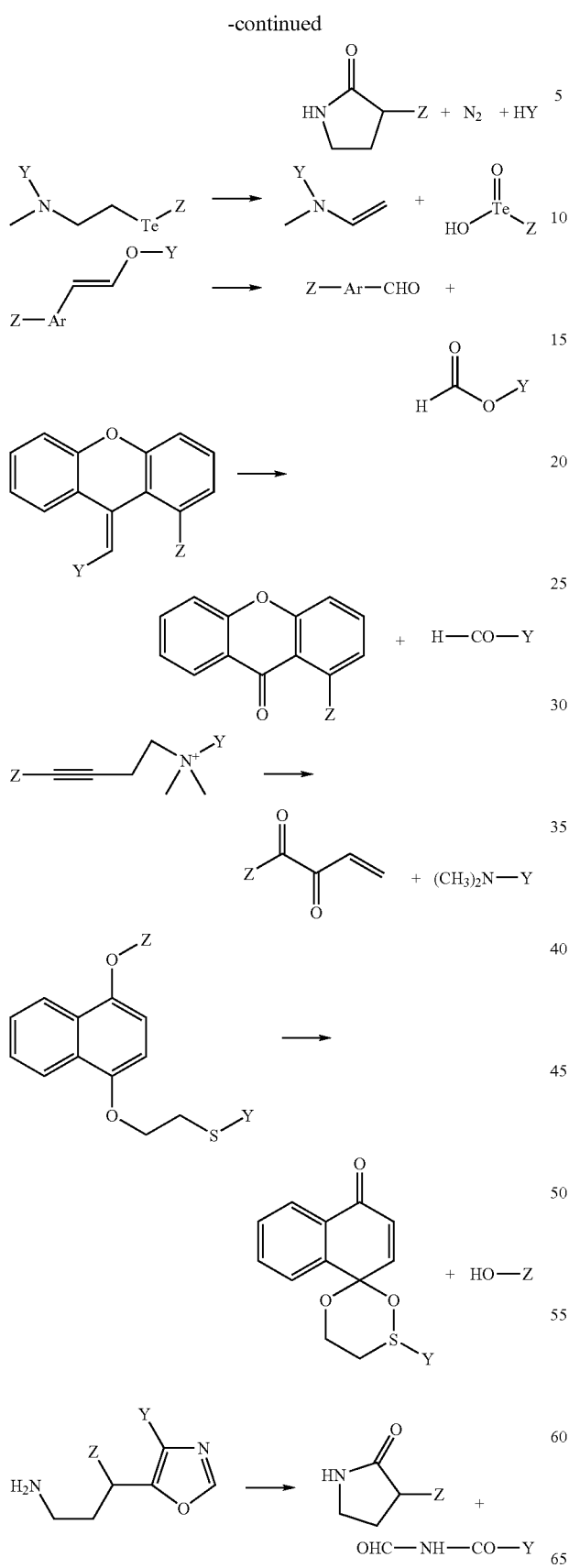

In these structures Z and Y may be either F or Q.

One specific example of an F-L-Q' compound of this type is the following:

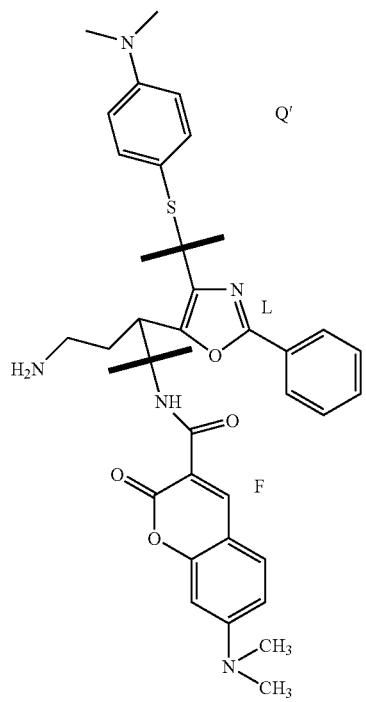

The thick angled lines in the above structure represent the boundaries of F-L and L-Q'.

Another example of F-L-Q' is the following:

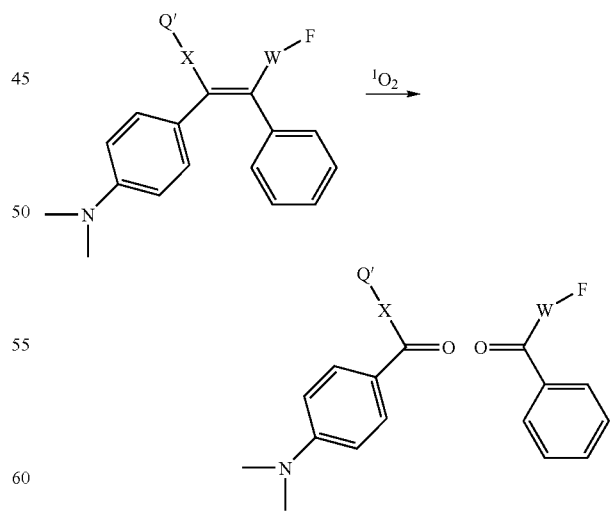

X and W are each selected from the group O, N and S. Both Q' and the aniline act as quenchers. Singlet oxygen cleavage releases Q' from F and converts the dimethylaniline to dimethyl aminobenzoyl which does not quench.

Another example of F-L-Q' is the following:

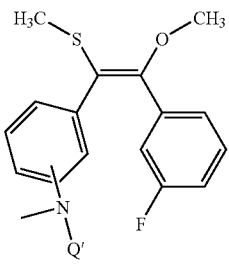

Another example of F-L-Q' and its reaction with singlet oxygen is the following:

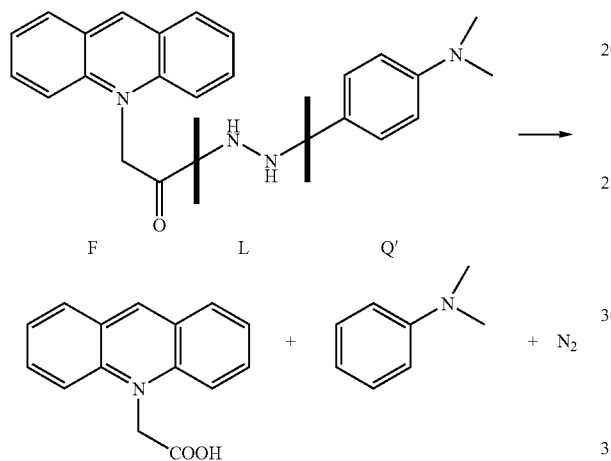

The thick vertical lines in the above structure represent the boundaries of F-L and L-Q'.

An example of F-L-Q' is the following:

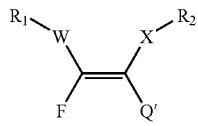

Where $R_1$ and $R_2$ are lower alkyl, higher alkyl, or aryl. Where X and W are defined such that the cleavable linker is a double bond that is an electron rich double bond. Wherein X and W independently are Se, Te, O, N (tertiary amine), S, aromatic, 1-alkyl, hetero-aromatic but with at least one of W, X, F and Q' having a S, O, Se or Te bonded to the olefin or an amine bonded to the olefin directly or through a series of conjugated double bonds, preferably none of the substituents has a saturated atom attached to the olefin to which is bound a hydrogen atom, unless W or X are hetero atoms, in which case F and Q' can be substitiuted with a saturated atom to the olefin.

Obviously, other types of linkers could be designed that would serve for L but all have the feature that they have a singlet oxygen reactive group and that they undergo cleavage subsequent to reaction with singlet oxygen. Further it is desirable that L's be selected that are stable, i.e., they do not react spontaneously with atmospheric oxygen or decompose spontaneously during storage at ambient temperatures. Preferably the linkers used for L will react with singlet oxygen with a bimolecular rate constant of at least $10^6$, preferably at least $10^7$, and desirably at least $10^8$ $M^{-1}Sec^{-1}$.

One example of a complete F-L-Q' compound and its reaction with singlet oxygen is the following:

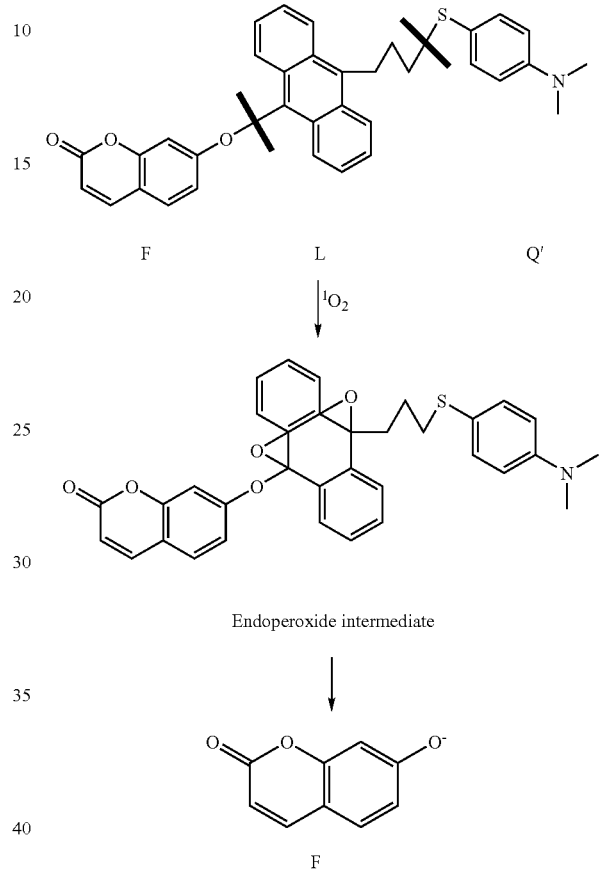

The thick angled lines in the top structure in the above reaction represent the boundaries of F, L and Q'. The sulfur atom acts as a reducing agent to accelerate the decomposition of the endoperoxide intermediate.

Quenchers, Q, that react with singlet oxygen with loss of their quenching properties must likewise be stable and react rapidly with singlet oxygen. Usually they will be electron donors including mono or di-alkyl or aryl hydrazines, alkyl or aryl hydroxylamines, or olefins, particularly olefins that are substituted with N, O, or S. Typical F-Q compounds and the products of their reaction with singlet oxygen, $F-Q_o$, include:

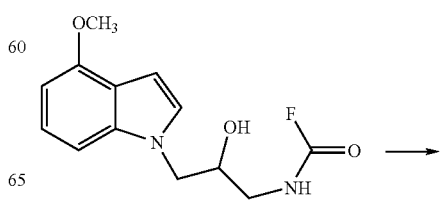

-continued

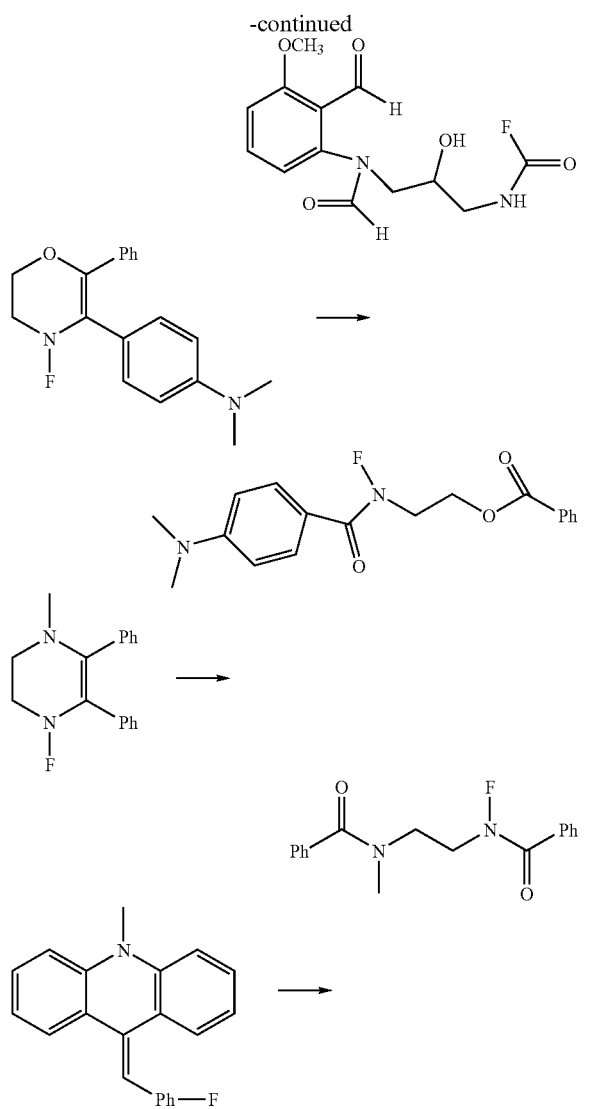

-continued

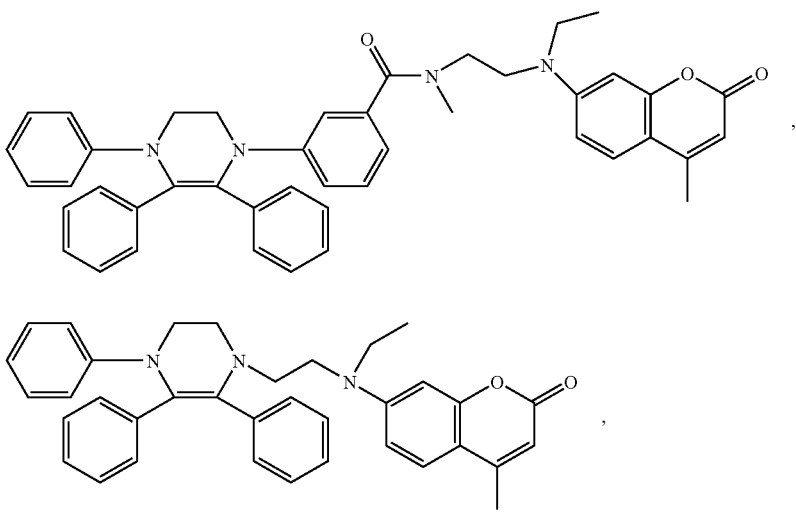

The point of attachment of L and Q to F is arbitrary but some sites may provide greater quenching than other sites. Optimization of the linking site is usually accomplished by trial and error although molecular modeling may sometimes be of value. Generally, relatively short chains linking the F to L or Q are preferred, usually 0 to 300 atoms in length, preferably 0 to 100, more preferably 1 to 20. Structures which have conformations that allow L or Q to approach or contact the pi-electron cloud on the planar surface of F will be preferred.

Some specific examples of F-Q include:

-continued

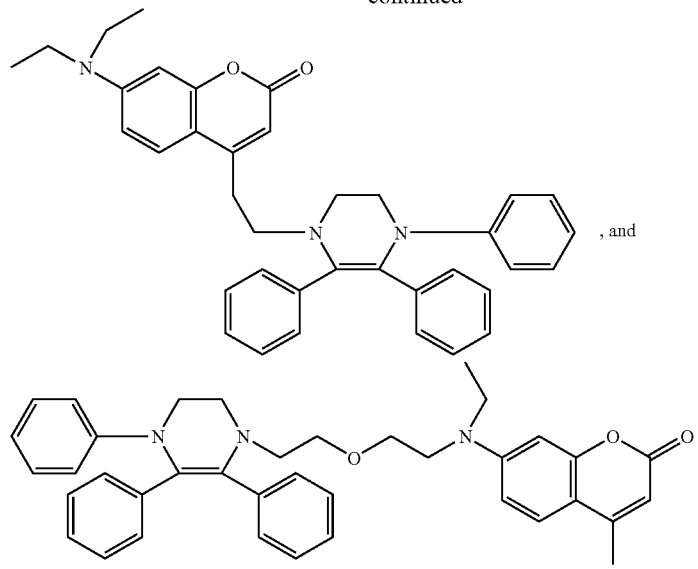

Figure 15:
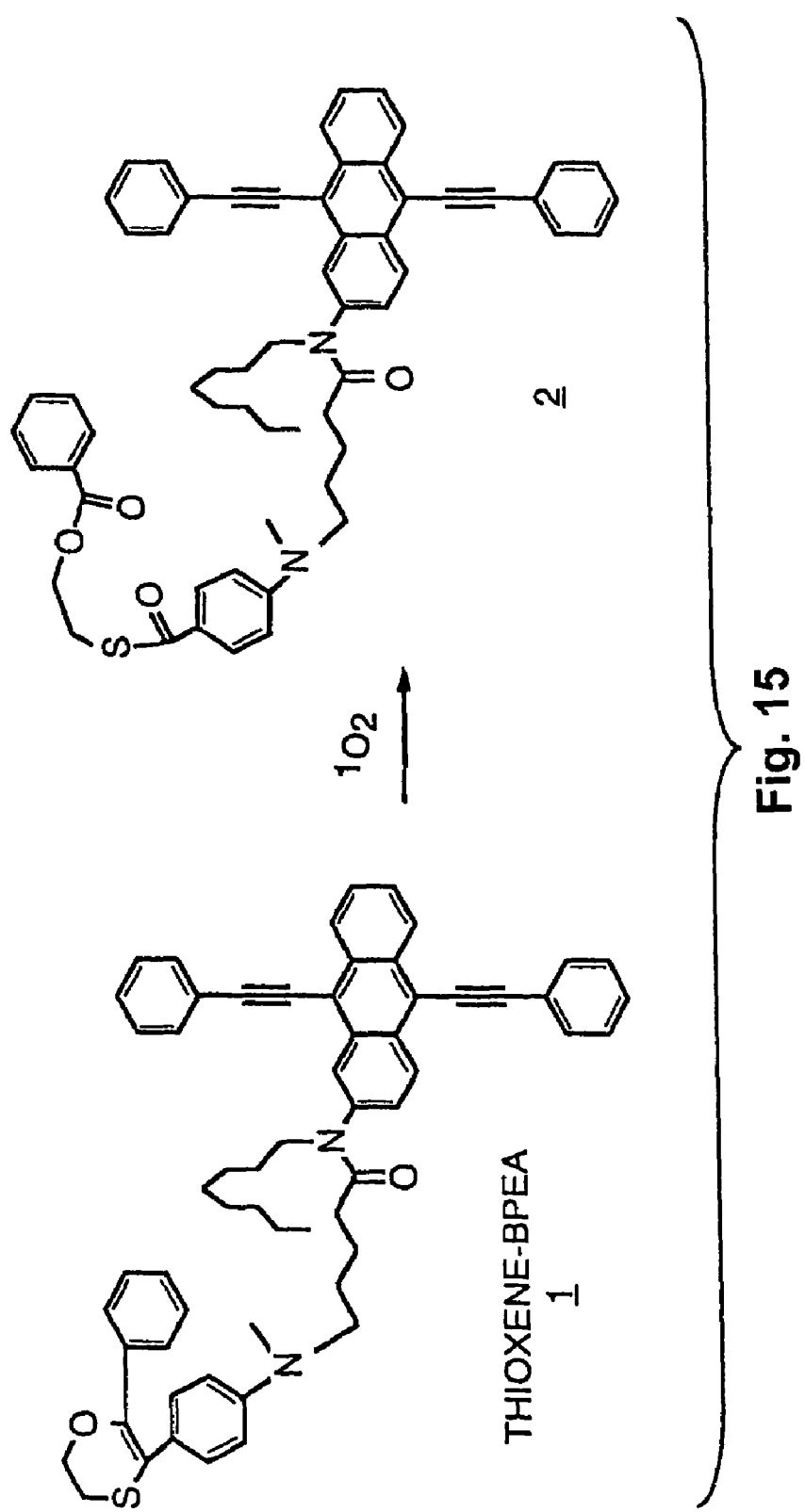
FIG. 15 illustrates the unquenching of thioxene-BPEA by reaction with singlet oxygen (Example 15).

In another embodiment of the invention the singlet-oxygen activatable indicator precursor compound of the F-Q is thioxene-9,10-bisphenylethynylanthracene, whose reaction with singlet oxygen is shown in FIG. 15.

In another embodiment of the invention the singlet-oxygen activatable indicator precursor compound is converted to a compound that can sensitize the emission of a fluorescent acceptor. In this example a dimethylamino coumarin is rendered fluorescent by cleavage of L. Irradiation in the presence of EuEDTA will then sensitize emission from the Eu at 613 nm:

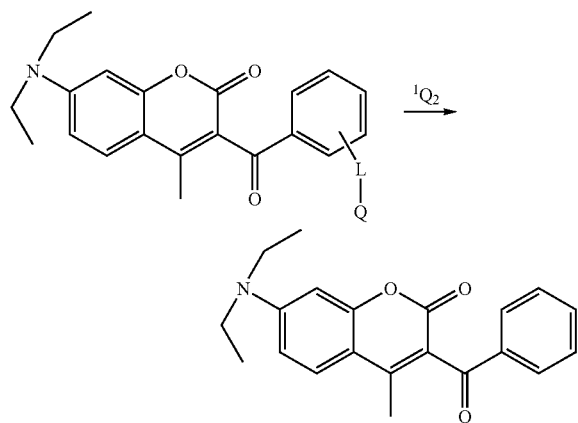

Compounds F-Q, including those of the F-L-Q' class, have been found to be useful for specific binding assays similar to those used for the FOCI method described U.S. Pat. No. 5,616,719, where the F-Q compounds replace the fluorophore precursors disclosed in that patent. In this method these compounds are usually dissolved in latex particles. For this application they must therefore be rendered sufficiently lipophilic that they will dissolve in the polymeric matrix.

F-L-Q' and F-Q can also be used by attaching them to surfaces that are exposed to an aqueous environment. For example, by including an attaching group such as a carboxylic acid to one of the subject compounds, the compound can be bound through amide linkages to the surface of a plastic film where the surface has free amino groups. Upon contacting the surface with a sample suspected of having bacteria, the bacteria will adhere because the surface is positively charged. (Alternatively, the bacteria could bind to antibodies affixed to the surface). The surface is then washed and contacted with a photosensitizer labeled antibody to the suspected bacteria and washed again, thereby causing photosensitizer labeled bacteria to be affixed to a surface with the subject compounds. Upon irradiation of the surface, fluorescent compounds will be produced only where the bacteria are bound, thus providing a permanent photograph.

Alternatively, the compounds of this invention could be attached to the surface of latex or other types of particles instead of incorporating them into the particles, or they could be incorporated into plastic films, cuvettes, microwells, etc., instead of binding them only to the surface.

For homogeneous assays the present invention is predicated on an analyte causing or inhibiting molecules of the photosensitizer and the substrate be closer to each other than their average distance in the bulk solution of the assay medium. The amount of this partitioning will depend upon the amount of analyte present in the sample to be analyzed. The photosensitizer molecules that do not become associated with the substrate produce singlet oxygen that is unable to reach the substrate before undergoing decay in the aqueous medium. However, when the photosensitizer and the substrate come in close proximity with each other in response to the presence of the analyte, the singlet oxygen produced upon irradiation of the photosensitizer can react with oxidant cleavable linker of the substrate to form a detectable product before undergoing decay. Because substrate molecules and/or photosensitizer molecules can be associated with a surface or can be incorporated into the material comprising the surface, the presence of a surface in conjunction with the photosensitizer and substrate compound can increase the efficiency of, or action of, singlet oxygen with the substrate molecule prior to decay. It is therefore preferred to bring one member of the substrate and photosensitizer pair into the proximity of a surface that incorporates the other member as a function of the presence of an analyte. The subject assay provides for a convenient method for detecting and measuring a wide variety of analytes in a simple, efficient, reproducible manner, which can employ simple equipment for measuring the amount of light produced during the reaction.

The amount of photosensitizer that comes in close proximity to the substrate is affected by the presence of analyte by virtue of the photosensitizer and substrate each being associated with an sbp member. This may be accomplished in a number of ways and the term "associated with" is defined thereby. The photosensitizer and substrate may contain functionalities for covalent attachment to sbp members and the sbp members may contain functionalities for attaching to the photosensitizer and/or substrate. The attachment may be accomplished by a direct bond between the two molecules or through a linking group which can be employed between an sbp member and the photosensitizer or substrate. In another embodiment either or both of the photosensitizer and substrate can be bound to surfaces or incorporated in particles, to which are also attached sbp members. In both cases each of the sbp members is capable of binding directly or indirectly to the analyte or an assay component whose concentration is affected by the presence of the analyte. Either or both of the photosensitizer and substrate can be incorporated into particles by virtue of being dissolved in at least one phase of the particles, in which case the solute will be at much higher concentration within the particle than in the bulk assay medium.

Alternatively, either or both of the photosensitizer and substrate may be covalently bound to particles, either by providing linking functional groups on the components to be bound or by incorporating the photosensitizer or substrate into a polymer that comprises the particles. For particles that are oil droplets or liposomes the photosensitizer and substrate can be attached to one or more long hydrocarbon chains, each generally having at least 10 to 30 carbon atoms. If the particles are droplets of a fluorocarbon, the photosensitizer or substrate incorporated into these particles may be fluorinated to enhance solubility and reduce exchange into other particles bound with the other label, and the hydrocarbon chain used for linking will preferably be replaced with a fluorocarbon chain. For silicon fluid particles the photosensitizer and substrate can be bound to a polysiloxane. In order to maximize the number of photosensitizer or substrate molecules per particle, it will usually be desirable to minimize the charge and polarity of the photosensitizer or substrate so that it resides within the non-aqueous portion of the particle. When the particle is a liposome and it is desired to retain the photosensitizer or substrate in the aqueous phase of the liposome, it will be preferred to use photosensitizers or substrates that are highly polar or charged.

No matter how the photosensitizer and the substrate are associated with their respective sbp member, it is critical that neither compound is capable of dissociating from its sbp member and becoming associated with the sbp member associated with the other member of the photosensitizer and substrate pair during the course of the assay. Thus, dissociation of these compounds from their respective sbp members must be slow relative to the time required for the assay.

The substate containing the oxidant cleavable linker may be bound to a sbp member that is capable of binding directly or indirectly to the analyte or to an assay component whose concentration is affected by the presence of the analyte. The term "capable of binding directly or indirectly" means that the designated entity can bind specifically to the analyte or assay component (directly) or can bind specifically to a specific binding pair member or to a complex of two or more sbp members which is capable of binding the other analyte or assay component (indirectly).

The surface generally has an sbp member bound to it. Preferably, the substrate via its oxidant cleavable linker is associated with the surface, preferably within a suspendible particle or bound to the surface of a microtiter plate or filter. This sbp member is generally capable of binding directly or indirectly to the analyte or a receptor for the analyte. When the sbp members associated with the photosensitizer and the substrate are both capable of binding to the analyte, a sandwich assay protocol can be used. When one of the sbp members associated with the photosensitizer or substrate can bind both the analyte and an analyte analog, a competitive assay protocol can be used. The attachment to a surface or incorporation in a particle of the substrate is governed, generally, by the same principles described above for the attachment to, or the incorporation into, a particle of the photo sensitizer.

The photosensitizer is usually caused to cleave the oxidant cleavable linker of the substrate by irradiating the medium containing these reactants. The medium must be irradiated with a short enough wavelength of light that has sufficient energy to convert the photosensitizer to an excited state and thereby render it capable of activating molecular oxygen to singlet oxygen. The excited state for the photosensitizer capable of exciting molecular oxygen is generally a triplet state which is more than about 20, usually at least 23 Kcal/mol more energetic than the photosensitizer ground state. Preferably, the medium is irradiated with light having a wavelength of about 450 to 950 nm, although shorter wavelengths can be used, for example, 230-950 nm, and longer wavelengths of up to 2000 nm can be used by providing sufficiently intense light to provide for biphotonic excitation.

Although it will usually be preferable to excite the photosensitizer by irradiation with light of a wavelength that is efficiently absorbed by the photosensitizer, other means of excitation may be used, for example, by energy transfer from an excited state of an energy donor. When an energy donor is used, wavelengths of light can be used which are inefficiently absorbed by the photosensitizer but are efficiently absorbed by the energy donor. The energy donor may be bound to an assay component that is associated, or becomes associated, with the photosensitizer, for example, bound to a surface or incorporated in the particle having the photosensitizer. When an energy donor is employed its lowest energy singlet and/or triplet state will usually be of higher energy than the lowest energy singlet and/or triplet state, respectively, of the photosensitizer.

The singlet oxygen so formed reacts and cleaves off the singlet-oxygen cleavable linker, forming a product that may be detected by any standard detection assay such as FOCI and LOCI. In practicing this invention, FOCI is the preferred detection assay for use in this invention.

Irradiation of the photosensitizer and the excitation of the photoactive indicator may be carried out simultaneously but will preferably be carried out sequentially so that the light used to excite the photosensitizer does not interfere with the fluorescence measurement. The singlet-oxygen activatable indicator precursor compound must not substantially absorb light at the wavelength used to generate the singlet oxygen and will therefore usually absorb at shorter wavelengths than the photosensitizer. In addition, the singlet-oxygen activatable indicator precursor compound will preferably not absorb significantly at the wavelength required to excite the photoactive indicator and, therefore, will usually absorb at shorter wavelengths than the photoactive indicator.

The method and compositions of the invention may be adapted to most assays involving sbp members such as ligand-receptor; e.g., antigen-antibody reactions; polynucleotide binding assays, and so forth. The assays may be homogeneous or heterogeneous, competitive or noncompetitive. The assay components, substrate with oxidant cleavable linker and photosensitizer, can be associated in a number of ways to a receptor, to a ligand, or, when employed, to a surface. The association may involve covalent or non-covalent bonds. Those skilled in the art will be able to choose appropriate associations depending on the particular assay desired in view of the foregoing and the following illustrative discussion.

The sample may be pretreated if necessary to remove unwanted materials. The reaction for a noncompetitive sandwich type assay can involve an sbp member, (e.g., an antibody, polynucleotide probe, receptor or ligand) complementary to the analyte and associated with a substrate; a photosensitizer associated with an sbp member, (e.g., antibody, polynucleotide probe, receptor or ligand) that is also complementary to the analyte; the sample of interest; and any ancillary reagents required. In a competitive protocol one sbp member can be a derivative of the analyte and the other sbp member can be complementary to the analyte, e.g., an antibody. In either protocol the components may be combined either simultaneously or wholly or partially sequentially. The ability of singlet oxygen produced by an activated photosensitizer to react with the singlet-oxygen cleavable linker to form a detectable product is governed by the binding of an sbp member to the analyte. Hence, the presence or amount of analyte can be determined by measuring the amount of product produced following the irradiation. Both the binding reaction and detection of the extent of the binding can be carried out in a homogeneous solution without separation, wherein, preferably, one or both of the photosensitizer and the substrate are incorporated in particles to which the sbp members are attached.

In a heterogeneous assay approach, one of the sbp members will frequently be bound to a support or another means provided to separate it from the assay medium. The support may be either a non-dispersible surface or a particle. In one embodiment, the support or particle will have associated with it one member of a group consisting of a substrate with a singlet-oxygen cleavable linker and the photosensitizer. Another sbp member will have the other member of the group associated with it wherein the sbp members can independently, either directly or indirectly, bind the analyte or a receptor for the analyte. These components are generally combined either simultaneously or wholly or partially sequentially. The surface or particles are then separated from the liquid phase and either are subjected to conditions for activating the photosensitizer and generating the detectable product. The detectable product can then be measured using a standard sandwich assay such as FOCI or LOCI.

Alternatively, a heterogenous assay of this invention may be carried out by providing means such as a surface to separate a first sbp member from the liquid assay medium and providing a second sbp member that is associated with a photosensitizer and that binds to the first sbp member as a function of the amount of analyte in the medium. The sample suspected of containing the analyte is then combined with the first and second sbp members either simultaneously or wholly or partially sequentially and the first sbp member is separated from the medium. A third sbp member associated with a substrate having a singlet-oxygen cleavable linker is then combined with the separated first sbp member where the third sbp member is capable of binding directly or indirectly to the second sbp member. The combination is then irradiated to activate the photosensitizer and generate the detectable product by cleavage of the singlet oxygen cleavable linker binidng the substrate to the support.

The binding reactions in an assay for the analyte will normally be carried out in an aqueous medium at a moderate pH, generally that which provides optimum assay sensitivity. Preferably, the activation of the photosensitizer will also be carried out in an aqueous medium. However, when a separation step is employed, non-aqueous media such as, e.g., acetonitrile, ethanol, isopropanol, toluene, benzonitrile, etc. and aqueous media with pH values that are very high, i.e., greater than 10.0, or very low, i.e., less than 4.0, preferably with pH values that are very high, can be used. As explained above, the assay can be performed either without separation (homogeneous) or with separation (heterogeneous) of any of the assay components or products.

The aqueous medium may be solely water or may include from 0.01 to 80 volume percent of a cosolvent but will usually include less than 40% of a cosolvent when an sbp member is used that is a protein. The pH for the medium of the binding reaction will usually be in the range of about 4 to 11, more usually in the range of about 5 to 10, and preferably in the range of about 6.5 to 9.5. The pH will usually be a compromise between optimum binding of the binding members and the pH optimum for the production of signal and the stability of other reagents of the assay. Usually, no change in pH will be required for signal production, although if desired, a step involving the addition of an acid or a basic reagent can be inserted between the binding reaction and generation of singlet oxygen and/or signal production. Usually, in homogenous assays the final pH will be in the range of 5-13. For heterogeneous assays non-aqueous solvents may also be used as mentioned above, the main consideration being that the solvent not react efficiently with singlet oxygen.

Various buffers may be used to achieve the desired pH and maintain the pH during an assay. Illustrative buffers include borate, phosphate, carbonate, tris, barbital and the like. The particular buffer employed is not critical to this invention, but in an individual assay one or another buffer may be preferred.

Moderate temperatures are normally employed for carrying out the binding reactions of proteinaceous ligands and receptors in the assay and usually constant temperature, preferably, 25° C. to 40° C., during the period of the measurement. Incubation temperatures for the binding reaction will normally range from about 50 to 45° C., usually from about 15° to 40° C., more usually 25° to 40° C. Where binding of nucleic acids occur in the assay, higher temperatures will frequently be used, usually 20° to 90°, more usually 35° to 75° C. Temperatures during measurements, that is, generation of singlet oxygen and light detection, will generally range from about 20° to 100°, more usually from about 25° to 50° C.

The concentration of analyte which may be assayed will generally vary from about $10^{-4}$ to below $10^{-16}$M, more usually from about $10^{-6}$ to $10^{-14}$M. Considerations, such as whether the assay is qualitative, semiquantitative or quantitative, the particular detection technique the concentration of the analyte of interest, and the maximum desired incubation times will normally determine the concentrations of the various reagents.

In competitive assays, while the concentrations of the various reagents in the assay medium will generally be determined by the concentration range of interest of the analyte, the final concentration of each of the reagents will normally be determined empirically to optimize the sensitivity of the assay over the range. That is, a variation in concentration of the analyte which is of significance should provide an accurately measurable signal difference.

The concentration of the sbp members will depend on the analyte concentration, the desired rate of binding, and the degree that the sbp members bind nonspecifically. Usually, the sbp members will be present in at least the lowest expected analyte concentration, preferably at least the highest analyte concentration expected, and for noncompetitive assays the concentrations may be 10 to $10^6$ times the highest analyte concentration but usually less than $10^{-4}$M, preferably less than $10^{-6}$M, frequently between $10^{-11}$ and $10^{-7}$M. The amount of photosensitizer or singlet-oxygen activatable indicator precursor compound associated with a sbp member will usually be at least one molecule per sbp member and may be as high as $10^5$, usually at least $10$-$10^4$ when the photosensitizer or substrate molecule is incorporated in a particle. The concentration of photosensitizer when it is incorporated in a particle is typically in the range of $1.0 \times 10^{-3}$-$9.0 \times 10^{-2}$ molar.

While the order of addition may be varied widely, there will be certain preferences depending on the nature of the assay. The simplest order of addition is to add all the materials simultaneously. Alternatively, the reagents can be combined wholly or partially sequentially. When the assay is competitive, it will often be desirable to add the analyte analog after combining the sample and an sbp member capable of binding the analyte. Optionally, an incubation step may be involved after the reagents are combined, generally ranging from about 30 seconds to 6 hours, more usually from about 2 minutes to 1 hour before the photosensitizer is caused to generate singlet oxygen and the substrate is cleaved to generate detectable product.

In a particularly preferred order of addition, a first set of sbp members that are complementary to and/or homologous with the analyte are combined with the analyte followed by the addition of specific binding pair members complementary to the first specific binding pair members, each associated with a different member of the group consisting of a photosensitizer and a substrate having an oxidant cleavable linker. The assay mixture, or a separated component of the assay mixture, is irradiated first to produce singlet oxygen and then later to produce detectable product.

In a homogeneous assay after all of the reagents have been combined, they can be incubated, if desired. Then, the combination is irradiated (at the necessary wavelengths of light) and the resulting product is measured by a detection assay. The detectable product is related to the amount of the analyte in the sample tested. The amounts of the reagents of the invention employed in a homogeneous assay depend on the nature of the analyte.

The present invention further encompasses compositions comprising a suspendible particle of 25 to 40000 nanometer average diameter comprising a substrate which is covalently bound to the particle matrix through a singlet-oxygen cleavable linker. The particles will preferably be polymeric or be oil droplets or vesicles such as liposomes. Where the particle is a liposome, the substrate will be associated with the lipid bilayer or dissolved in the aqueous interior of the liposome. The particle will have an sbp member bound to it. Also, encompassed are compositions comprised of two complementary sbp members bound to each other wherein one is associated with a photosensitizer and one is associated with a substrate.

Another aspect of the present invention relates to kits useful for conveniently performing an assay method of the invention for determining the presence or amount of an analyte in a sample suspected of containing the analyte. Vold et el. (U.S. Pat. No. 5,561,049, incorporated herein by reference) provides details of the preparation of kit components similar to those of the current invention. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. The kit comprises (1) a composition wherein the composition comprises a suspendible particle comprising a substrate covalently bound to the particle matrix through a singlet-oxygen cleavable linker, the particle having an sbp member bound to it, and (2) a photosensitizer. The photosensitizer can be attached to an sbp member or it can be associated with a particle, to which an sbp member is bound. The kit can further include other separately packaged reagents for conducting an assay including ancillary reagents, and so forth.

Another embodiment of a kit in accordance with the present invention comprises in packaged combination a substrate having an oxidant cleavable liner associated with a first sbp member and a photosensitizer capable in its excited state of activating oxygen to its singlet state associated with a second sbp member.

Another embodiment of the present invention is a detection method based on a fluorescence microscope with its sensitivity only limited by the nonspecific binding. For example, the imaging or scanning microscope will count the fluorescent spots before and after turning on the laser beam that generates $^1O_2$ and the difference gives us a quantitative detection of the amount of analyte (e.g. nucleic acids, antigen, antibody). For the fluorescence microscope approach, the fluorescence background will be limited by spatial separation of paired beads versus non-paired beads. With 10,000 fluorescent molecules generated in one F-bead by $^1O_2$, a commercial digital camera can be used to replace an expensive CCD camera on most fluorescence imaging systems. A 100 microliter sample volume can be reduced to a 1 mm diameter spot with a membrane pre-loaded with probe beads, in which a sponge paper will be placed under the membrane to absorb solvent. A cartridge with multiple spots with membrane pre-loaded probe beads will allow us to have a panel test done simultaneously to increase the throughput. Other Sensitizer molecules, such as, porphyrins which can generate $^1O_2$ with 488 nm light, can be used to replace the sensitizer molecule currently used on S-beads which require 680 nm light. Then, the assay, for a non-amplified nucleic acid or antigen can be performed on conventional fluorescence microscope which are widely used in hospitals and clinical laboratories.

In another embodiment of the present invention the sensitizer is an enzyme which generates singlet oxygen when substrates are provided for the reaction catalyzed by the enzyme. In one embodiment this enzyme is a haloperoxidase and the substrates include hydrogen peroxide and a halide salt, such as sodium bromide or sodium chloride.

In another embodiment of the present invention the singlet oxygen activatable precursor compounds are used to determine the rate of formation of singlet oxygen in a sample. In one embodiment the sample is suspected of containing macrophages and an assay utilizing the singlet oxygen activatable precursor compounds measures activation of the macrophages. Macrophages are known to generate reactive oxygen species upon activation.

SPECIFIC EXAMPLES

The following assays are provided by way of illustration and not limitation to enable one skilled in the art to appreciate the scope of the present invention and to practice the invention without undue experimentation. It will be appreciated that the choice of analytes, photosensitizers, substrate molecules, surfaces, particles and reaction conditions will be suggested to those skilled in the art in view of the disclosure herein in the examples that follow.

The following examples illustrate preparation of Dig-Linked-Biotin-Oxazole-RNHS ester (DLBOR-$CO_2$NHS ester) (13) (Example 1); Dig-Linked-Biotin-Anthracene-RNHS ester (DLBAR-$CO_2$NHS ester)(16) (Example 2); Dig-Linked-Biotin-Anthracene-R Beads (DLBAR-Beads)(18) for nucleic acid detection amplification (Example 3); Dig-Linked-Biotin-Anthracene-R/Oligo beads (DLBAR/Oligo-beads)(19) for nucleic acid detection amplification (Example 4); measurement of Dig-Linked-Biotin (DLB) release from DLBAR-Y using soluble sensitizer (Example 5); measurement of DLB release from DLBAR-beads using bead pairs (Example 6); measurement of fluorescence depletion (Example 7); LOCI amplification using a single tube single instrument nucleic acid detection amplification format (Example 8); LOCI amplification using lactoperoxidase label (Example 9); LOCI amplification for the detection of HbsAg (Example 10); reversible coupling of oligonucleotides onto a support or surface (Example 11); reversible quenching of coumarin fluorescence (Example 12); synthesis of thioxene-BPEA (Example 13); method for preparing components of FOCI nucleic acid detection system (Example 14); and application of thioxene-BPEA in FOCI nucleic acid detection assay (Example 15).

Parts and percentages recited herein are by weight unless otherwise specified. Temperatures are in degrees centigrade (° C.). Unless indicated otherwise, chemicals were reagent grade and commercially available from sources such as Gibco, (Rockville, Md.), Aldrich Chemical Company (Milwaukee, Wis.) and Sigma Chemical Company (St. Louis, Mo.). All solutions were prepared in water and all reactions were performed under ambient conditions unless otherwise stated.

2-ethoxyethanol was from Aldrich Chemical Co. and was redistilled under vacuum. Sodium hydroxide was 0.1 N. Isopropanol, hydrazine, and N-(2,3-epoxypropyl) phthalimide were from Aldrich Chemical Co. N-heptadecylbenzene was from Pfaltz and Bauer. Tween 20 was Surfact-Amps 20 (Pierce Chemical Company, Rockford, Ill.). Acetylated BSA was from Gibco BRL, Gaithersburg, Md. HBR-1 (Heterophile Blocking Agent) was from Scantibodies Laboratory Inc., Sautee, Calif. Kathon was from Rohm and Haas Company, Philadelphia, Pa.

Unless otherwise indicated, oligonucleotides used in the following examples were prepared by synthesis using an automated synthesizer and were purified by gel electrophoresis or HPLC.

The following abbreviations have the meanings set forth below:

BGG - Bovine gamma globulin
bp - base pairs
BPEA - 9,10-Bis(phenylethynyl)anthracene
BSA - Bovine serum albumin
DMF - dimethylformamide
DMSO - dimethyl sulfoxide
DNA - Deoxyribonucleic acid
dsDNA - Double-stranded DNA
DNTPs - 2'-deoxynucleoside-5'-triphosphates
DOPE - L-α-(dioleoyl)-phosphatidyl ethanolamine
DOPE-MCC - L-α-(dioleoyl)-phosphatidyl β-(4-(N-maleimidomethyl)- cyclohexane-1-carboxyamido)ethanol
DTT - dithiothreitol from Sigma Chemical Company, St. Louis, MO.
EDAC - 1-ethyl-3-(3-dimethylaminopropyl)-carbodiimide hydrochloride.
EDTA - ethylenediaminetetraacetate
F - Fluorescent compound
FOCI - Fluorescent oxygen chaneling assay
FWP - Forward primer
g - gram
HBR - Heterophile Blocking Agent (Scantibodies Laboratory, Inc., Santee, CA)
HPLC - high performance liquid chromatography.
hr - hour
Ig - Immunoglobulin
IHTBB - In house buffer with BSA
L - liter or linker
LC - liquid chromatography
LOCI - Luminescent oxygen channeling immunoassay
LSIMS - Liquid secondary ionization mass spectroscopy
M - molar
MAD - Maelimidated dextran
m - milli
MES - 2-(N-morpholino)ethane sulfonic acid.
n - nano
min - minute
mmol - millimoles
MOPS - 3-(N-morpholino)propanesulfonic acid
NMR - nuclear magnetic resonance spectroscopy
p - pico
PCR - polymerase chain reaction
Pfu/exo(-)polymerase - Pyrococus furiosus DNA/exo
Q - quencher
RNA - Ribonucleic acid
r-RNA - Ribosomal RNA
sbp - Specific binding pair member
sec - second
SIAX - Succinimidyl 6-((iodoacetyl)amino)hexanoate
SPA - Single primer amplification
SPDP - N-succinimidyl 3-(2-pyridylthio)-propionate.
ssDNA - Single-stranded DNA
Sulfo-SMCC - N-sulfosuccinimidyl-4-(N-maleimidomethyl)cyclohexane-1- carboxylate
TSO - Template switching oligonucleotide
TAR - Thioxene/Anthracene/Rubrene t-butyl-phthalocyanine - Bis-triphenylsilyl-tetra-t butyl phthalocyanin
t-RINA - transfer RNA
TCEP - tris-carboxyethyl phosphine
THF - tetrahydrofuran
TLC - Thin-layer chromatography
TMS - trimethylsilane
TMSCl- trimethylsilylchloride
TRIS - Tris(Hydroxymethyl) Aminoethane
Tris HCl - Tris(hydroxymethyl)aminomethane-HCl (a 10X solution) from BioWhittaker, Walkersville, MD.
μ - micro Example 1

Preparation of Dig-Linked-Biotin-Oxazole-R-NHS ester (DLBOR-$CO_2$NHS ester) (13)

This Example describes the preparation of DLBOR-$CO_2$NHS ester as shown in FIG. 1.

A. Materials and Instrumentation:

All reagents were reagent grade and were used without further purification with the exception of THF and toluene which were freshly distilled from sodium before use and diisopropylethylamine which was dried over 3 Å sieves. Silica gel 250 analytical plates were obtained from Analtech. $^1$H-NMR was recorded on a Bruker 250 MHz FT-NMR Spectrometer using deuterated solvents obtained from Aldrich. UV spectra were run on a Hewlett Packard model 8452A Diode Array Spectrophotometer. Manual chemiluminescence measurements were made on a custom built Oriel Box, automated chemiluminescence measurements were made on a TECAN Model 5052. Fluorescence measurements were made on a Hitachi F-4500 Fluorescence Spectrophotometer. Mass spectra were obtained from the UC Berkeley Mass Spectrometry Laboratory. Particle sizing was run on a NICOMP Submicron Particle Sizer, Model 370. Ultracentrifugation was done on a Du Pont Instruments Sorvall RC 5B Refrigerated Superspeed Centrifuge. All reactions were run under an argon atmosphere. All potentially light sensitive reactions were wrapped in foil to exclude light. None of the reactions were optimized.

1. Preparation of N-(hydroxyphenacyl) biotin benzyl ester (7a 2.).

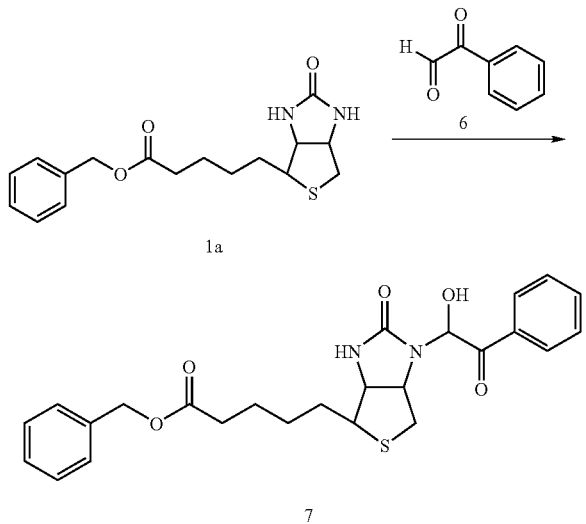

Phenyl glyoxal monohydrate (6) (2.70 g, 0.02 mol) was dissolved in anhydrous toluene (20 ml) and azeotroped with a Dean Stark adapter, until the 1H-NMR showed no hydrate. Biotinyl benzyl ester (1a) (3.4 g 0.01 mol) was then added and the solution was refluxed at 120° C. for 2 h. The solution turns from orange to yellow. The reaction mixture was concentrated and purified by flash chromatography on silica gel using 1-5% MeOH in $CH_2Cl_2$ as the eluent.

Yield 1.2 g of (7) as a faintly yellow solid. Note that this compound is hydrolytically unstable, hence aqueous work up was completely avoided.

1H-NMR(CDCl$_3$, 250 MHz): δ 8.2 (d, 2H), 8.1 (d, 2H), 7.6 (m, 2H), 7.45 (m, 4H), 6.6-6.2 (m, 3H), 5.3-3.9 (m, 5H), 3.4-1.3 (m, 10H).

2. Preparation of N-oxazolyl biotin benzyl ester (8).

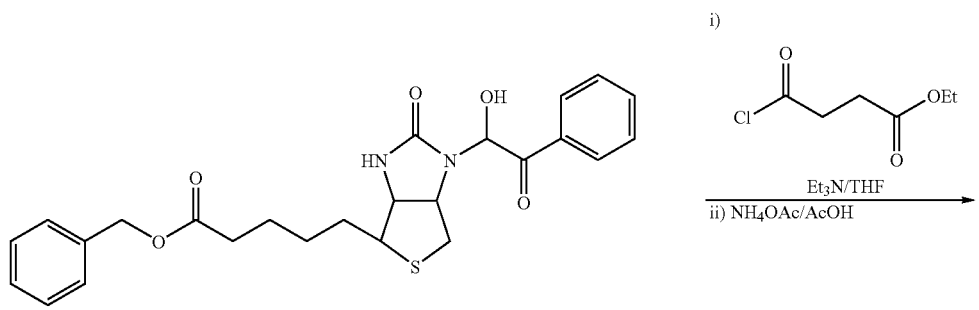

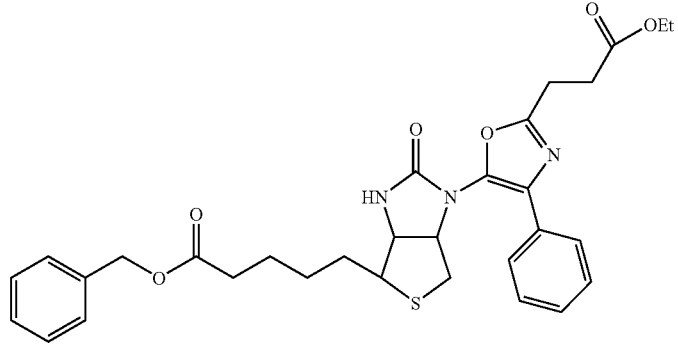

8

A solution of the N-(hydroxyphenacyl) biotin benzyl ester (7) (468 mg, 1.0 mmol) in 5 mL of anhydrous THF was cooled to 0° C. and ethyl succinyl chloride (150 uL, 1.05 mmol) added. The mixture was stirred under argon and triethylamine was added, the reaction was allowed to attain ambient temperature over 4 h. The reaction mixture was concentrated and chloroform (10 ml) was added, and the precipitated Et$_3$N.HCl was filtered off. Purification by preparative thin layer chromatography on silica (2% MeOH in CH$_2$Cl$_2$) gave 490 mg (0.86 mmol) of the desired O-acylated biotin derivative as judged by 1H-NMR.

The O-acyl derivative (400 mg 0.7 mmol) from the last step was treated with acetic acid (3.0 ml) and anhydrous NH$_4$OAc (800 mg). The mixture was heated at 120° C. for 4 h. The reaction mixture was neutralized (pH 7.0) with 10% NaHCO$_3$ solution and extracted with CH$_2$Cl$_2$ (3×20 ml). The organic portions were pooled and dried over anhydrous Na$_2$SO$_4$. The solid was purified by preparative thin layer chromatography (2 plates, 1000 microns, 2% MeOH in CH$_2$Cl$_2$) to yield 23 mg of N-oxazolyl biotin benzyl ester (8) together with 210 mg of biotin benzyl ester.

3. Preparation of N-oxazolyl biotin NHS ester (9).

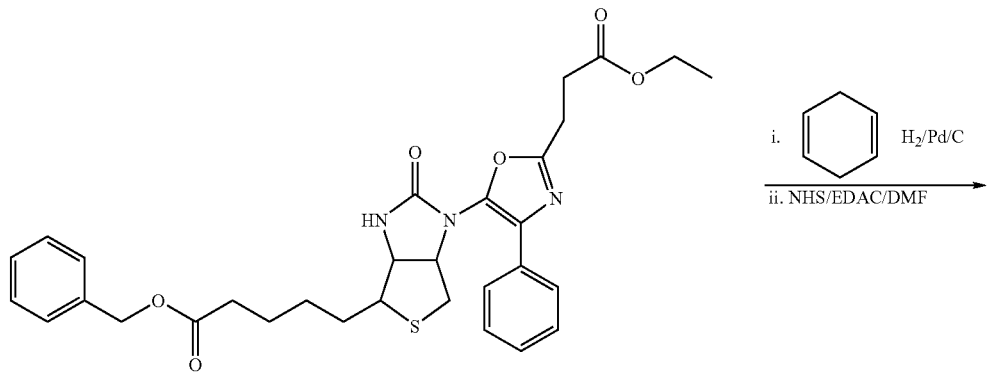

8

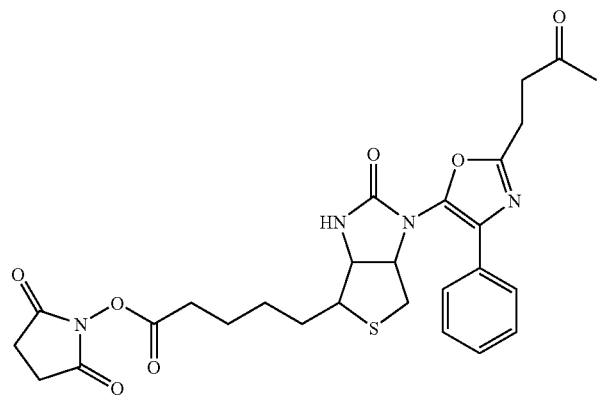

9

The N-oxazolyl biotin benzyl ester (8) (200 mg) was stirred with 20 mg of Pd/C in 2.0 mL cyclohexadiene and 5.0 mL ethanol at reflux under a hydrogen atmosphere at ambient pressure. The reaction was followed by NMR ($^1$H NMR (D$_2$O) δ: >10 (br 1H), 8.0-7.2 (m, 6H), 4.5-4.0 (m, 4H), 3.6-2.5 (m, 7H), 2.2 (m, 2H), 1.55 (m, 2H), 1.3 (m, 2H), 1.15 (m, 5H).

Note that in the absence of cyclohexadiene, the benzyl group was not removed, presumably because of catalyst poisoning by the sulfur. Following filtration and removal of solvent, the residue was redissolved in DMF (5 mL) and treated with a slight excess of NHS and EDAC. After stirring overnight at ambient temperature, the reaction was judged to be complete by testing with benzylamine on TLC (5% MeOH/CH$_2$Cl$_2$). This solution of N-oxazolyl biotin NHS ester (9) was used directly in the next step.

4. Preparation of Boc-Linked-Dig (10)
   a. 3-ketodigoxgenin (10B)

Platinum oxide (489 mg) was suspended in 20 ml of deionized water and reduced to platinum metal in a Parr hydrogenation apparatus at 40 psi of hydrogen at room temperature for two hours. The platinum was then transferred to a solution of 500 mg (1.28 mmol) of digoxigenin 10a (prepared as described in Ferland, J. M. Can. J. Chem. 1974, 652) in 50 ml of dry acetone. The reaction was placed under a steady stream of air and stirred at room temperature for three days. The reaction was worked up by filtering the catalyst off through a pad of Celite and evaporating the solvent. 449 mg (90% yield) of the crude product 10a was obtained, which was of sufficient purity for use in the subsequent step.

b. 3-Aminodigoxigenin (10c)

To 448 mg (1.26 mmol) of 3-ketodigoxigenin 10b dissolved in 5 ml of methanol was added 100 mg (6.74 mmol) of ammonium acetate. The reaction was stirred at room temperature under argon for 30 minutes. Then 85 mg (1.35 mmol) of sodium cyano brohydride was added and stirring was continued for two more hours at room temperature. The 3-aminodigoxigenin 10C was formed rapidly. The reaction was quenched by addition of 4 ml of glacial acetic acid and evaporated to dryness. The crude product was dissolved in 20 ml of n-butanol, then extracted with 25 ml of a solution of 1 g/ml of potassium carbonate in water. The aqueous phase was washed with 3×25 ml of n-butanol. The combined organic phase was dried and evaporated to dryness to yield 365 mg (69%) of the 10c as white solid. The crude product was of sufficient purity for use in the next step. NMR: (CD$_3$OD) 0.79(s, 3H, C18), 0.96(s, 3H, C19), 1.00(s, 3H, C19), 1.1-2.3 (m, CH2's and CH's), 3.4 (m, 1H, C12), 4.95(m, 2H, C21), 5.91(s, 1H, C22). M.S.: (EI) 473 M+ d. Boc-linked dig 10

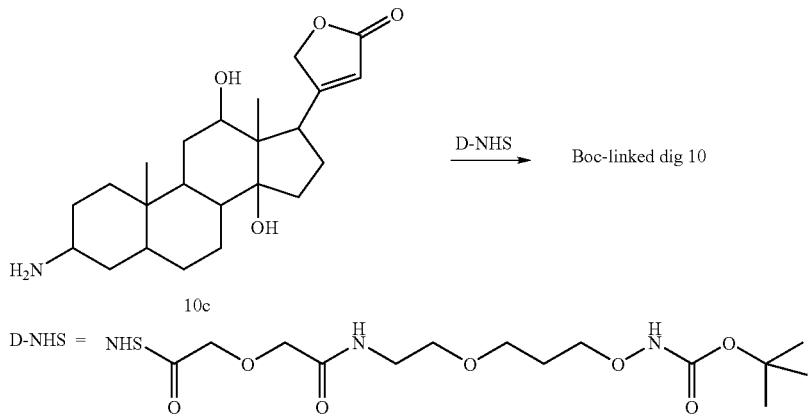

To a solution of N-tboc acid 10c (Aldrich, 721 mg, 2.0 mmol) in THF (25 ml) were added DCC (412 mg, 2.0 mmol) and NHS (287 mg, 2.5 mmol). The mixture was stirred overnight. The reaction was then filtered through glass wool and added to a stirred solution of aminodigoxigenin 10c and triethyl amin (101 mg) in 25 ml of dichloromethane. The reaction was stirred overnight and then was concentrated under vacuum. Dichloromethane (50 ml) was then added and extracted with 3×50 ml of 0.5 N HCl and finally with water (100 ml). The organic phase was then dried and evaporated to ⅓ of the volume and applied to ten 20×20 silicagel GF plates ($CH_3OH:H_2O$, 1:9), to give 1.2 g of the pure product.

5. Preparation of Digoxigenin-Linked-Biotin-Oxazole-R-$CO_2$Et (11).

Boc-Linked-Dig (10) (30 mg, 0.04 mmol) was deprotected by stirring in 1.0 ml (1:5) TFA-$CH_2Cl_2$ for 15 min at ambient temperature. The reaction mixture was concentrated and the volatiles removed by dissolving the residue in $CH_2Cl_2$ and concentrating a second time. The residue was redissolved in 2 mL $CH_2Cl_2$ and neutralized with TEA in 1 ml DMF. The NHS-Biotin-Oxazole-R—$CO_2$Et filtrate (9) was rinsed with 0.5 mL THF directly into the DMF diluted amino-Linked-Dig solution. The solution was bubbled with argon and stirred for 2 h at ambient temperature. TLC ($SiO_2$: 10% MeOH/$CH_2Cl_2$) confirmed that the reaction had gone to completion. The crude reaction mixture was applied directly to a pre-equilibrated (5% MeOH/$CH_2Cl_2$) preparative silica gel plate and

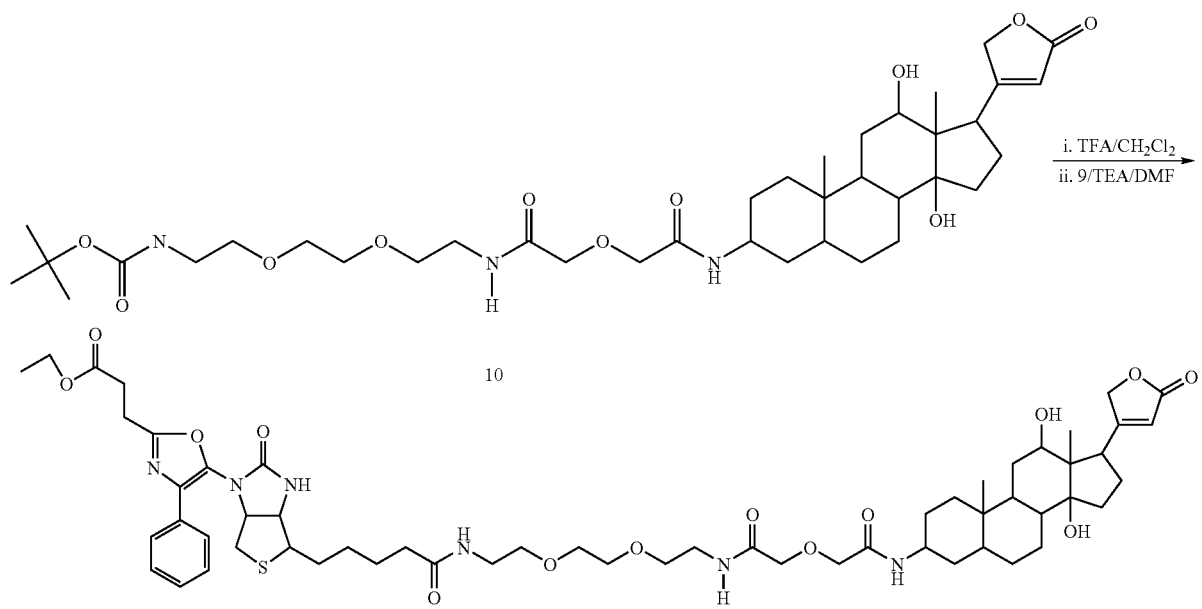

eluted with 15% MeOH/CH$_2$Cl$_2$. The pure product fractions were combined affording 16 mg DLBOR-CO$_2$Et (11). TLC (SiO$_2$: 0.1% HOAc, 15% MeOH/CH$_2$Cl$_2$, single spot R$_f$ 0.3). 1H-NMR (250 MHz, D$_2$O) δ: 7.9-7.1 (m, 5H), 5.7 (s, 1H), 5.65 (s, 1H), 4.9 (s, 2H), 4.6 (7H+H$_2$O), 4.25 (m, 2H), 4.1 (m, 2H), 3.95 (m, 2H), 3.65 (m 2H), 3.6-3.25 (m, 10H), 3.25-2.85 (m, 7H), 2.85 (m, 2H), 2.25 (M, 1H), 2.0 (m, 2H), 1.75 (m, 2H), 1.6-0.9 (m, 26H), 0.75 (s, 3H), 0.60 (s, 3H).

6. Preparation of Dig-Linked-Biotin-Oxazole-R acid (DLBOR-CO$_2$H) (12).

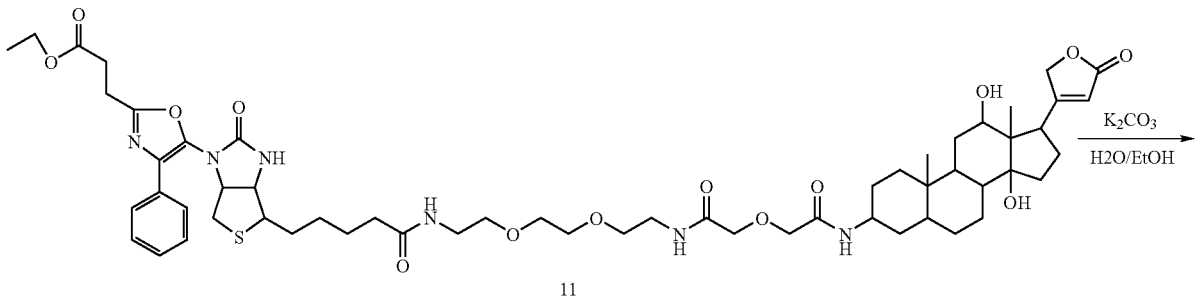

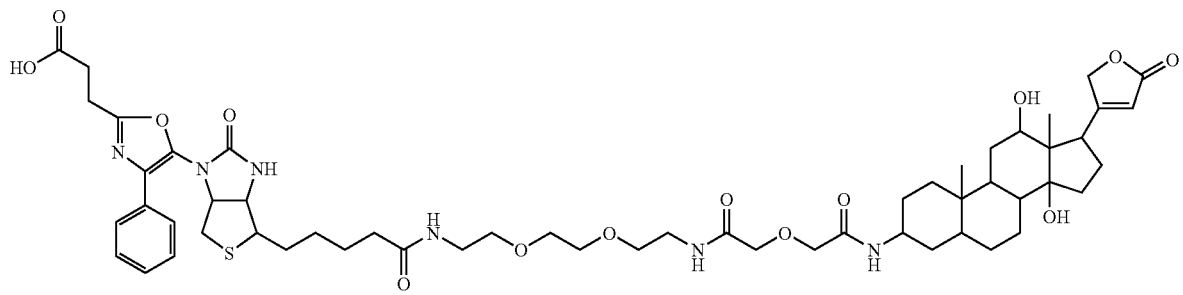

To 10.0 mg DLBOR-CO$_2$Et (11) (9.0 umol), dissolved in 100 uL EtOH, was added 1.0 mL of 25 mM K$_2$CO$_3$ in 5% H$_2$O/EtOH. The solution was stirred under argon overnight at ambient temperature. The reaction was followed by TLC (SiO$_2$: 5% MeOH/CH$_2$Cl$_2$), after 18 h the pH of the reaction was adjusted to 3-4 with 0.1 N HCl. TLC (C18: 95% CH$_3$CN/H$_2$O, major spot R$_f$ 0.5, and SiO$_2$: 0.1% HOAc, 15% MeOH/CH$_2$Cl$_2$, major spot R$_f$ 0.65, and a minor spot R$_f$ 0.90 (the minor spot appeared to be digoxin-linked biotin), NMR confirmed the complete hydrolysis of the ethyl ester. Dig-Linked-Biotin (DLB) release by $^1$O$_2$ was confirmed by the soluble sensitizer method (see Example 5). The solvent was removed under vacuum and a 2.0 mg (1.7 umol) portion of the crude DLBOR acid (12) was redissolved in 0.50 mL DMF for use in the next step.

7. Preparation of Dig-Linked-Biotin-Oxazole-R-NHS ester (DLBOR-CO$_2$NHS ester) (13).

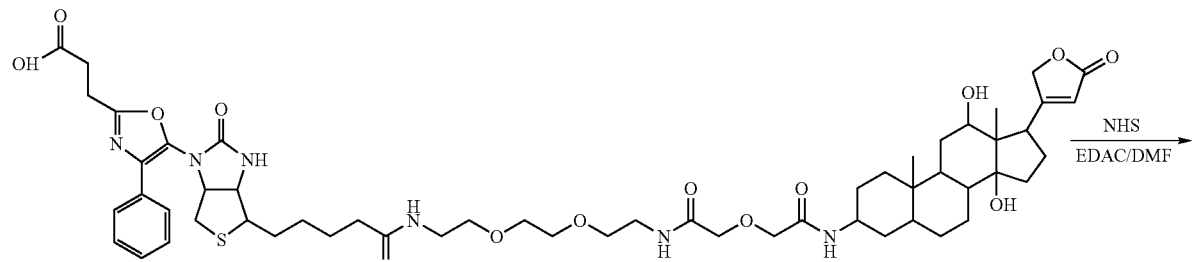

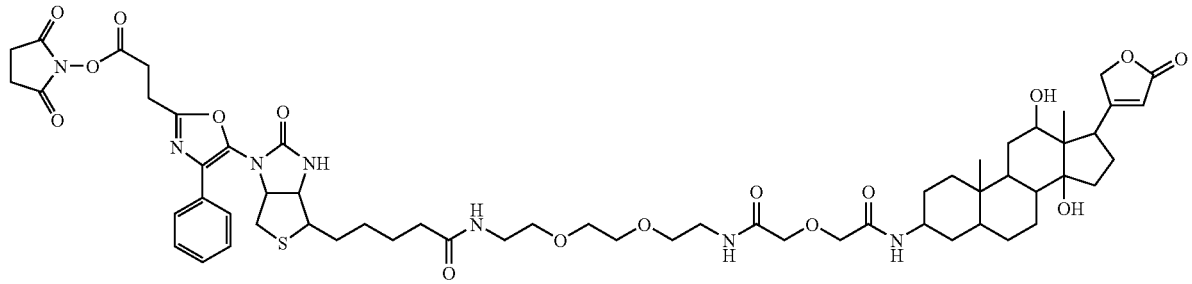

13

To 2.0 mg (1.7 umol) DLBOR-CO₂H (12) in 0.5 mL DMF was added 10 uL of NHS (0.23 mg, 2.0 mmol)/DMF and EDAC. The solution was stirred under argon overnight at ambient temperature. The solvent was removed under vacuum and the residue was redissolved in 100 uL of degassed DMF. This DMF solution of DLBOR—CO₂NHS (13) was attached directly to beads in the same manner as described for DLBAR-CO₂NHS (see FIG. 3 and Example 2).

Example 2

Preparation of Dig-Linked-Biotin-Anthracene-R-NHS ester (DLBAR-CO₂NHS ester) (16).

Figure 2:
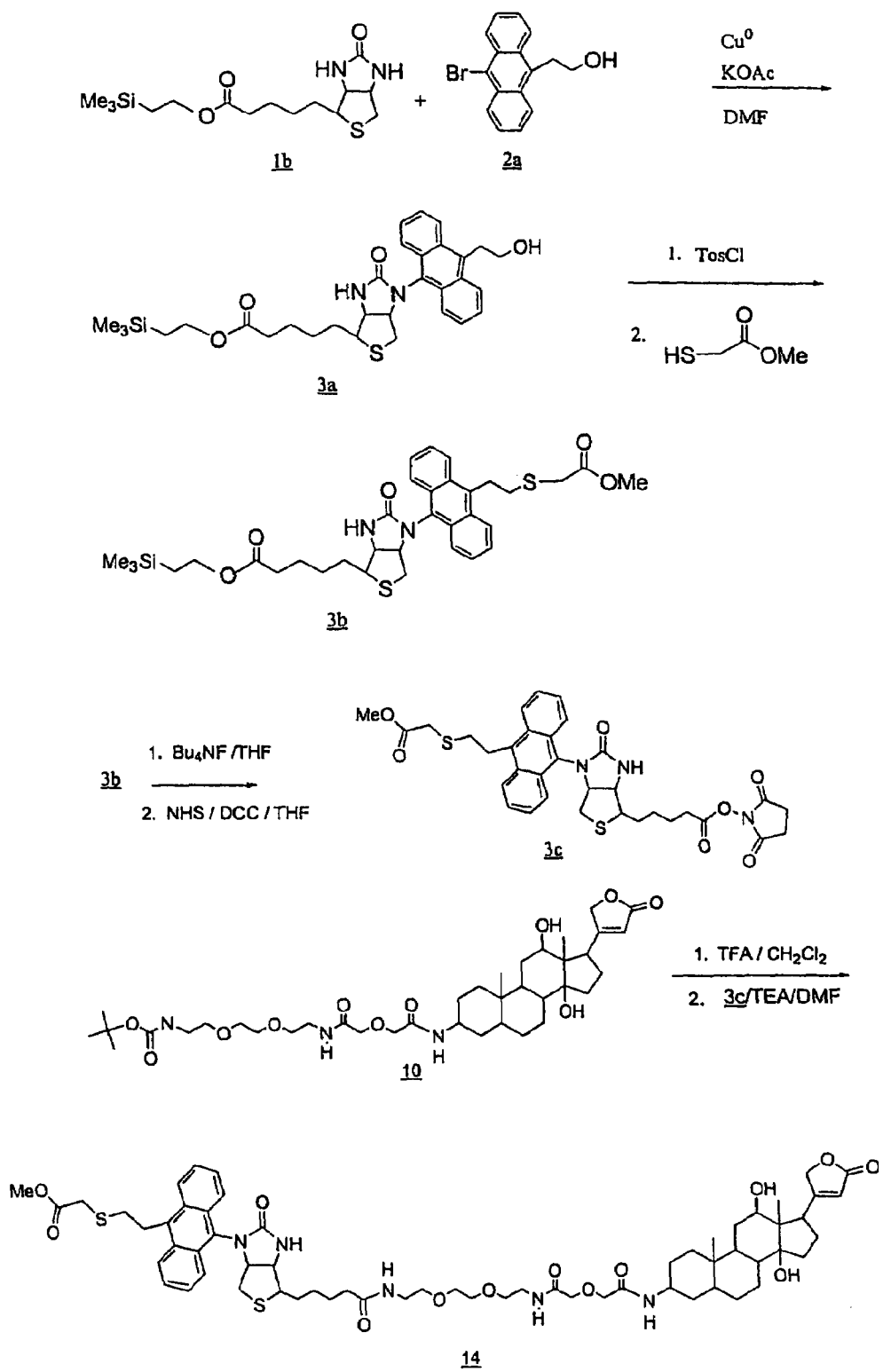
FIG. 2 illustrates the preparation of $DLBAR-CO_2$methyl ester.
Figure 3:
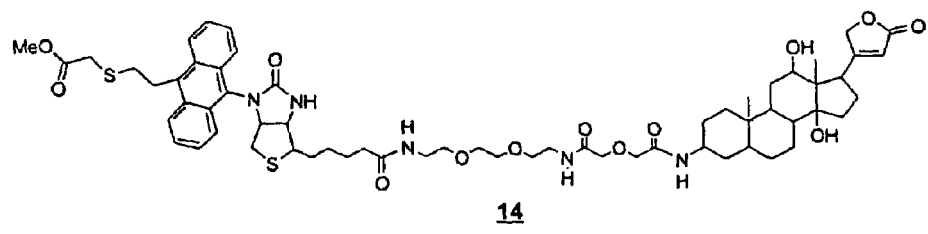
FIG. 3 illustrates the preparation of DLBAR-oligo beads from $DLBAR-CO_2Me$.
Figure 3:
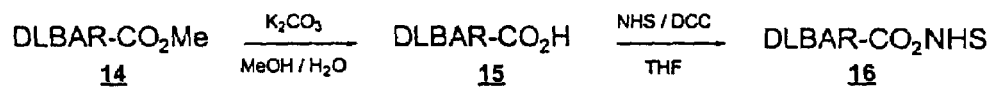
Figure 3:
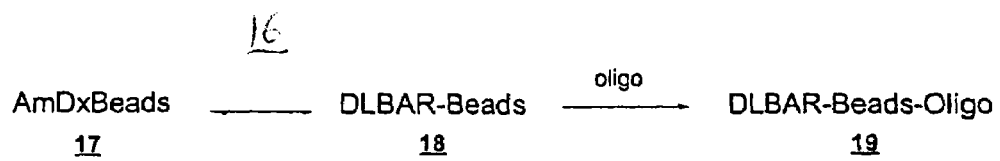

This Example describes the preparation of DLBAR-CO₂NHS ester as shown in FIGS. 2 and 3.

1. Preparation of Trimethylsilylethylbiotin-hydroxyethylanthracene (3a).

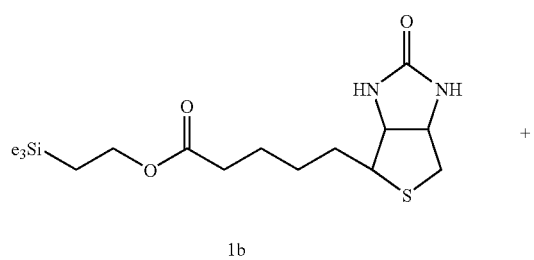

1b

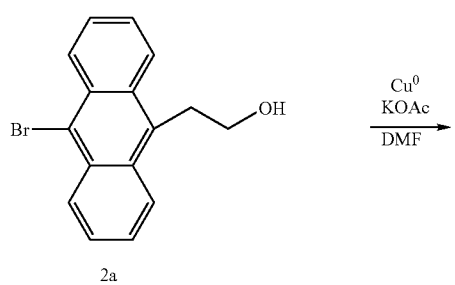

2a

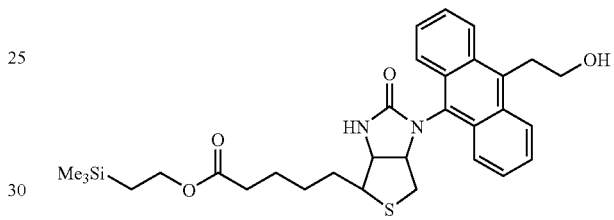

3a

Biotin was protected with trimethylsilylethanol using DCC in DMF at ambient temperature. Following removal of the urea by filtration, volatiles were removed by rotary evaporation at 60°, <1 mmHg. The crude product was further purified by Chromatotron chromatography, affording 2.0 g of trimethylsilylbiotin (1b). The purity was estimated to be >99% by TLC (4% MeOH/CH₂Cl₂). The structure was verified by NMR (see ¹H NMR (CDCl₃) δ: 5.8 (s, 1H), 5.4 (s, 1H), 4.5 (m, 1H), 4.3 (m, 1H), 4.1 (t, 2H), 3.1 (m, 1H), 2.9 (m, 1H), 2.7 (m, 1H), 2.3 (t, 2H), 1.65 (m, 4H), 1.4 (m, 2H), 0.95 (t, 2H), 0.05 (s, 9H).

The silyl protected biotin (1b) (1.21 g, 3.54 mmol) was combined with 9-bromo-10-hydroxyethylanthracene (2a) (1.066 g, 3.54 mmol), copper powder (225 mg, 3.54 mmol), and potassium acetate (0.42 g, 4.25 mmol) in 10 ml DMF. The mixture was bubbled with argon for 5 min, and stirred overnight at 130°. The crude product was concentrated twice from 35 ml 5% MeOH/CH₂Cl₂, and purified by Chromatotron chromatography (1-5% MeOH/CH₂Cl₂, then 66% EtOAc/hexane) affording 124 mg pure silyl protected biotin anthracene alcohol (3a). (TLC: SiO₂; 4% MeOH/CH₂Cl₂, NMR: ¹H NMR (CDCl₃) δ: 8.6 (dd, 1H), 8.35 (m, 2H), 8.05 (dd, 1H), 7.6 (m, 4H), 6.05 (s, 1H), 5.05 (d, 1H), 4.65 (t, 1H), 4.2 (t, 2H), 3.85 (m, 4H), 3.3 (m, 1H), 2.6 (s, 2H), 2.3 (t, 2H), 1.9 (m, 2H), 1.7 (m, 2H), 1.6 (m, 2H), 1.2 (s, 1H), 1.0 (t, 2H), 0.1 (s, 9H))

2. Preparation of Trimethylsilylethylbiotin-anthracenyl-ethylthioacetic acid methyl ester (3b).

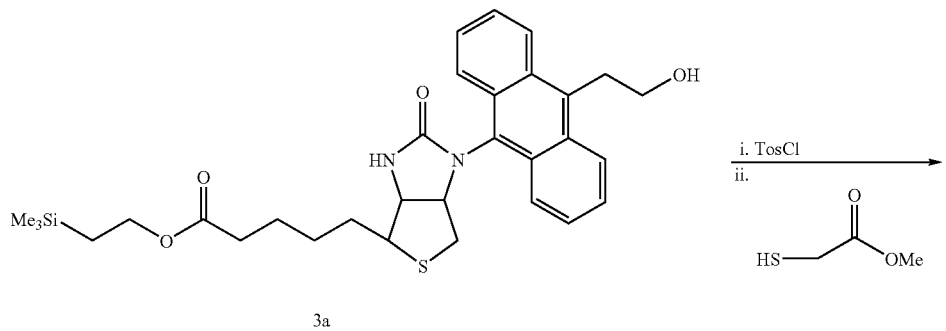

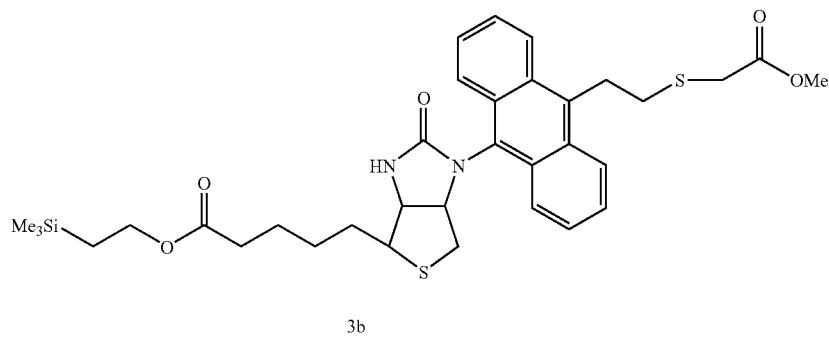

A portion (108 mg, 0.191 mmol) of the protected biotin-anthracene alcohol (3a) was dissolved in 1.0 mL dry $CH_2Cl_2$, under argon. Dry pyridine (0.10 mL) was added, and the solution was cooled with an ice bath. Tosyl chloride (57 mg, 1.5 eq) was added portion wise. The reaction was stirred and allowed to warm to ambient temperature overnight. The crude reaction was partitioned between 5 mL EtOAc and 5 mL saturated aqueous $NaHCO_3$. The organic phase was extracted twice with equal volumes of water. The combined aqueous phase was back extracted once with 5 mL EtOAc, and the combined organic phase was extracted with an equal volume of saturated sodium chloride, dried with $Na_2SO_4$, filtered, concentrated, and redissolved in $CH_2Cl_2$. Chromatotron Chromatography (0-3% $MeOH/CH_2Cl_2$), followed by concentration, afforded 120 mg product. TLC: $SiO_2$; 4% $MeOH/CH_2Cl_2$, and NMR ($^1$H NMR ($CDCl_3$) δ: 8.5 (m, 1H), 8.25 (m, 1H), 8.1 (m, 1H), 7.95 (m, 1H), 7.7 (m, 2H)7.55 (m, 4H), 7.3 (m, 2H), 5.8 (br, 1H), 5.05 (m, 1H), 4.6 (m, 1H), 4.35 (m, 2H), 4.2 (m, 2H), 4.05 (m, 2H), 3.3 (m, 1H), 2.6 (s, 2H), 2.4 (s, 3H), 2.3 (m, 2H), 1.9 (m, 2H), 1.9-1.4 (m, 4H), 1.0 (t, 2H), 0.05 (s, 9H)) confirmed that the product was pure silyl protected biotin anthracenyl-ethyltosylate. The tosylate (120 mg, 0.173 mmol) was redissolved in 2.0 mL dry DMF. To this solution was added 1.0 mL diisopropylethylamine and 0.3 mL methyl thioglycolate. The reaction was bubbled with argon, and stirred overnight at 55°. Volatiles were removed under reduced pressure, and the residue was purified by Chromatotron Chromatography (2 mm $SiO_2$ rotor, 1-2% $MeOH/CH_2Cl_2$). Pure fractions (TLC: $SiO_2$, 4% $MeOH/CH_2Cl_2$) were combined and concentrated to afford 75 mg of pale yellow film. The structure of this product was identified to be title compound (3b) by NMR ($^1$H NMR ($CDCl_3$) δ: 8.5 (m, 1H), 8.3 (m, 2H), 8.0 (m, 1H), 7.6 (m, 4H), 5.9 (br, 1H), 5.05 (m, 1H), 4.6 (m, 1H), 4.15 (t, 2H), 3.95 (m, 2H), 3.7 (s, 3H), 3.4 (s, 2H), 3.3 (m, 1H), 3.05 (m, 2H), 2.6 (s, 2H), 2.25 (m, 2H0, 1.85 (m, 2H), 1.8-1.3 (m, 4H, +$H_2O$), 1.0 (t, 2H), 0.05 (s, 9H)).

3. Preparation of NHS-biotin-anthracenyl-ethylthioacetic acid methyl ester (3c).

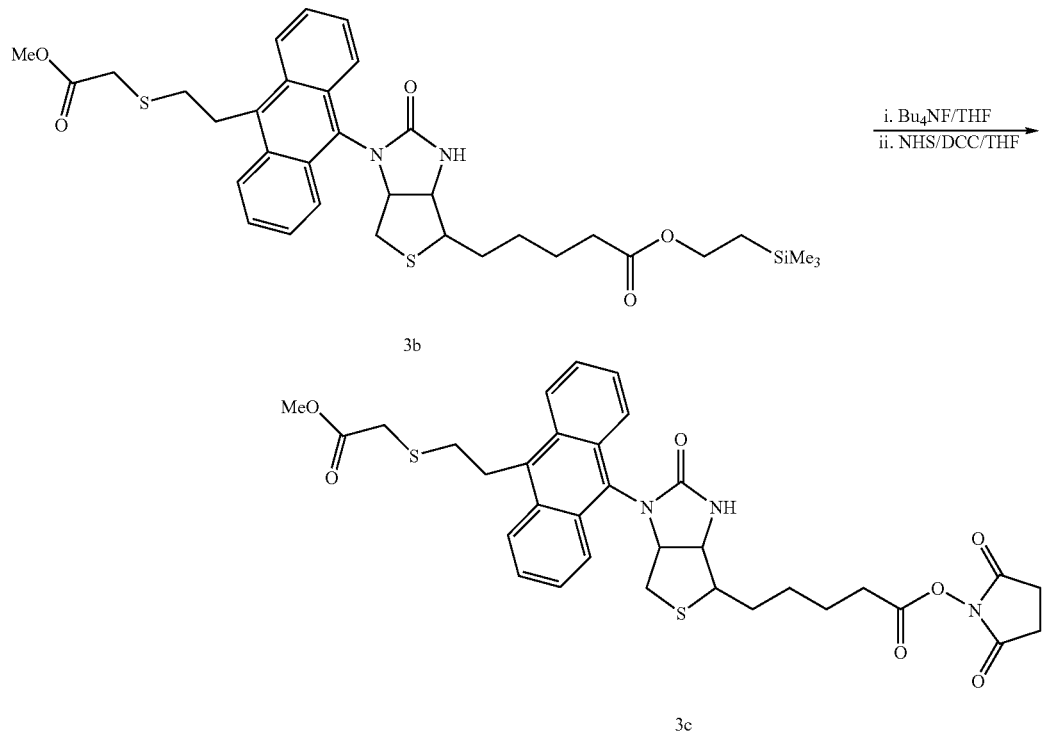

Tetrabutyl ammonium fluoride (0.50 mL 1 M in THF) was added to a solution of trimethylsilylethylbiotin-anthracenyl-ethylthioacetic acid methyl ester (3b) (72 mg, 0.11 mmol) in 1.0 mL THF. The solution was stirred under argon for 2 h at ambient temperature. TLC (SiO$_2$: 10% MeOH/CH$_2$Cl$_2$) confirmed that the reaction had gone to completion. Solvent was removed by rotary evaporation, and the residue was partitioned between 2 mL EtOAc and 2 mL of an aqueous phase consisting of three volumes saturated NH$_4$Cl adjusted to pH 2.5 with 0.1 M HCl diluted with one volume of water. After separation, the aqueous phase was back extracted with 2 mL EtOAc. The combined organic phases were dried with anhydrous Na$_2$SO$_4$, and concentrated affording 58 mg deprotected product. The purity and structure were confirmed by TLC and NMR ($^1$H NMR (CDCl$_3$) δ: 8.5 (m, 1H), 8.3 (m, 2H), 8.0 (m, 2H), 7.55 (m, 4H), 5.05 (m, 1H), 4.7 (m, 1H), 4.15 (m, 1H), 3.95 (m, 2H), 3.7 (s, 3H), 3.5 (s, 2H), 3.3 (m, 1H), 3.0 (m, 2H), 2.6 (s, 2H), 2.5-2.2 (m, 2H), 1.9 (m, 2H), 1.8-1.3 (m, 2H, +H$_2$O), 1.25 (m, 2H)). A portion of this product (52.5 mg, 0.095 mmol) was combined with DCC (25 mg, 0.12 mmol) and NHS (14 mg, 0.12 mmol) and stirred under argon overnight at ambient temperature. The reaction was judged to be complete by TLC (SiO$_2$: 10% MeOH/CH$_2$Cl$_2$, testing a 20 uL aliquot as the morpholide derivative). Following removal of the urea by filtration, the crude filtrate (3c) was used directly in the next step.

4. Preparation of <u>D</u>ig-<u>L</u>inked-<u>B</u>iotin-<u>A</u>nthracene-<u>R</u> methyl ester (DLBAR methyl ester) (14).

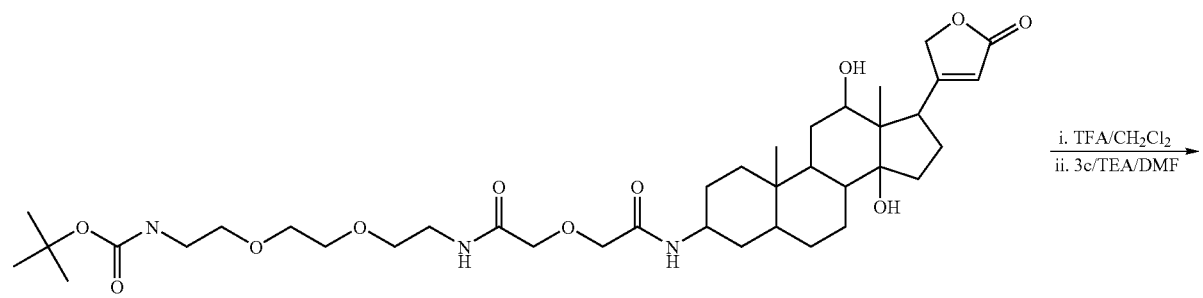

-continued

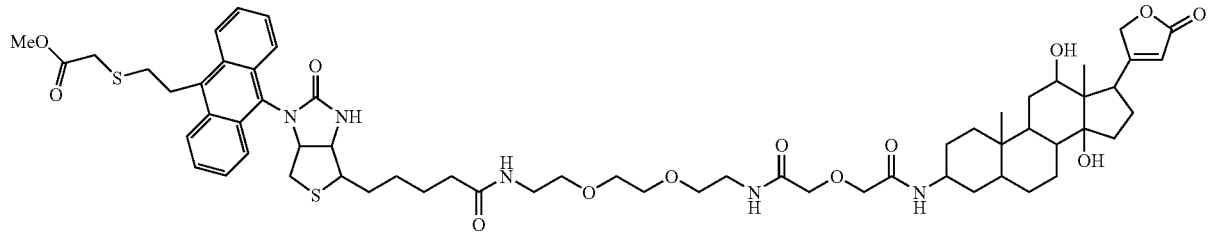

14

Figure 7:
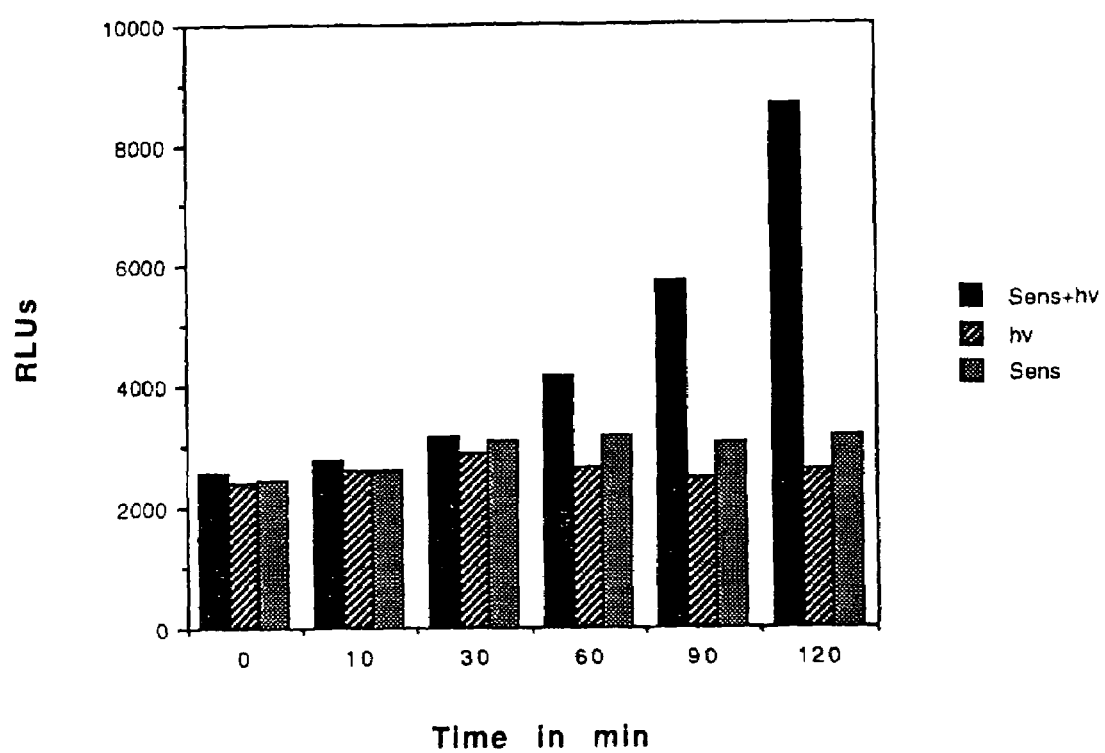
FIG. 7 illustrates detection of the cleavage product of $DLBAR-CO_2Me$ with a LOCI sandwich assay that employed a chemiluminescer anti-dig acceptor beads and streptavidin sensitizer beads (Example 5).

Boc-Linked-Dig (10) (118 mg, 0.16 mmol) was deprotected by stirring in 1.0 mL (1:1) TFA-CH$_2$Cl$_2$ for 15 min at ambient temperature. Volatiles were removed by rotary evaporation and chased three times with 2 mL CH$_2$Cl$_2$. The residue was redissolved in 2 mL CH$_2$Cl$_2$ (the pH was adjusted to 7-8 with TEA for short-term storage), and diluted with 0.10 mL TEA in 1 mL DMF (the pH of the diluted solution was 9-10 by moist paper). The NHS-Biotin-Anthracene filtrate (3c) was rinsed with 0.5 mL THF directly into the DMF diluted amino-Linked-Dig solution. The solution was bubbled with argon and stirred for 2 h at ambient temperature. TLC (SiO$_2$: 10% MeOH/CH$_2$Cl$_2$) confirmed that the reaction had gone to completion. The crude reaction mixture was applied directly to a pre-equilibrated (5% MeOH/CH$_2$Cl$_2$) 2 mm SiO$_2$ Chromatotron rotor and eluted with 5-15% MeOH/CH$_2$Cl$_2$. The pure product fractions were combined affording 56 mg DLBAR-CO$_2$Me (14). TLC (RP-C18: 95% ACN/H$_2$O, single spot R$_f$ 0.7; and SiO$_2$: 0.5% HOAc, 15% MeOH/CH$_2$Cl$_2$, single spot R$_f$ 0.6), NMR ($^1$H NMR (CDCl$_3$) δ: 8.5 (d, 1H), 8.35 (d, 1H), 8.30 (d, 1H), 8.0 (m, 1H), 7.6 (m, 4H), 5.9 (s, 1H), 5.1 (d, 1H), 4.85 (s, 1H), 4.70 (t, 2H), 4.0 (m, 6H), 3.7-3.2 (m, 19H), 3.15 (t, 2H), 2.6 (s, 2H), 2.6-2.4 (m, 5H+H$_2$O), 2.3 (t, 2H), 2.0-1.0 (m, 27H), 0.85 (d, 3H), 0.75 (s, 3H)) and MS were used to confirm the purity and structure of the product. Dig-Linked-Biotin (DLB) release by $^1$O$_2$ was confirmed by the soluble sensitizer method (see Example 5 and FIG. 7).

5. Preparation of Dig-Linked-Biotin-Anthracene-R acid (DLBAR-CO$_2$H) (15).

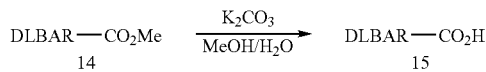

To 9.0 mg DLBAR-CO$_2$Me (14) (7.7 umol), dissolved in 100 uL MeOH, was added 1.0 mL of 25 mM K$_2$CO$_3$ in 5% H$_2$O/MeOH. The solution was stirred under argon overnight at ambient temperature. The reaction was followed by TLC (SiO$_2$: 5% MeOH/CH$_2$Cl$_2$), after 43 h the pH of the reaction was adjusted from ~10 to ~3 with 60 uL 1 N HCl. TLC (C18: 95% ACN/H$_2$O, major spot R$_f$ 0.4 minor spot R$_f$ 0.3, and SiO$_2$: 0.5% HOAc, 15% MeOH/CH$_2$Cl$_2$, major spot R$_f$ 0.75 minor spot R$_f$ 0.80 (the minor spots are thought to be dig-amine isomers that should not effect the performance of the product) and NMR confirmed the complete hydrolysis of the methyl ester. Dig-Linked-Biotin (DLB) release by $^1$O$_2$ was confirmed by the soluble sensitizer method (see Example 5). The solvent was removed under vacuum and a 2.0 mg (1.7 mmol) portion of the crude DLBAR acid (15) was redissolved in 0.50 mL THF for use in the next step.

6. Preparation of Dig-Linked-Biotin-Anthracene-R-NHS ester (DLBAR-CO$_2$NHS ester) (16).

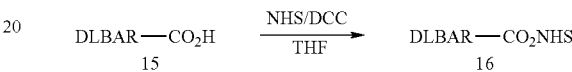

To 2.0 mg (1.7 mmol) DLBAR-CO$_2$H (15) in 0.5 mL THF was added NHS (0.23 mg, 2.0 umol) in 10 uL THF and DCC (0.41 mg, 2.0 mmol) in 10 uL THF. The solution was stirred under argon overnight at ambient temperature. The solvent was removed under vacuum and the residue was redissolved in 100 uL of degassed DMF. This DMF solution of DLBAR-CO$_2$NHS (16) was used directly in the next step.

Example 3

Preparation of Dig-Linked-Biotin-Anthracene-R Beads (DLBAR-Beads) (18) for Nucleic Acid Detection Amplification.

This Example describes preparation of hydroxypropylaminodextran-coated latex beads (AmDxBeads) (17) and coupling with DLBAR-CO$_2$NHS (16) (prepared in Example 2) to generate DLBAR-Beads (18) as shown below. See FIGS. 3 and 4.

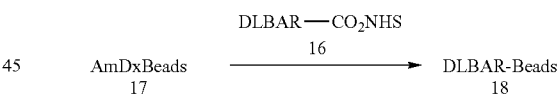

1. Preparation of Hydroxypropylaminodextran

Hydroxypropylaminodextran was prepared by dissolving Dextran T-500 (Pharmacia, Uppsala, Sweden) (100 g) in 500 mL of H$_2$O in a 3-neck round-bottom flask equipped with mechanical stirrer and dropping funnel. To the above solution was added 45 g sodium hydroxide, 50 mg EDTA, 50 mg NaBH$_4$, 50 mg hydroquinone and 200 g N-(2,3-epoxypropyl) phthalimide. The mixture was heated and stirred in a 90° C. water bath for 2 hr. A small aliquot was precipitated three times from methanol and analyzed by NMR. Appearance of a peak at 7.3-7.6 δ indicated incorporation of phthalimide. The main reaction mixture was precipitated by addition to 3.5 L of methanol and the solid was collected. The phthalimide protecting group was removed by dissolving the product above in 500 mL of 0.1 M acetate buffer, adding 50 mL of 35% hydrazine and adjusting the pH to 3.5. The mixture was heated at 80° C. for 1 hr, the pH was readjusted to 3.2, and the mixture was heated for an additional one-half hour. An aliquot was precipitated three times in methanol. NMR showed that the phthalimide group was no longer present. The reaction mixture was neutralized to pH 8 and stored at room temperature.

The product was purified by tangential flow filtration using a 50,000 molecular weight cut-off filter, washing with about 0.8 L water, 0.5 L of 0.1M HCl, 0.5 L of 0.01 M NaOH, and finally 3 L of water. The product solution was concentrated by filtration to 700 mL and then was lyophilized. Determination of reactive amines using trinitrobenzenesulfonate indicated about 1 amine per 16 glucose residues. Preparation of a second lot at twice the scale gave almost identical results.

2. Preparation of Hydroxypropylaminodextran-coated Beads (AmDxBeads)(17)

A solution of hydroxypropylaminodextran (synthesized as described above) was prepared at 100 mg/mL in 50 mM MES (pH 6). The pH was re-adjusted to 6 with 1M HCl. Three hundred (300) mg Seradyn carboxylated latex beads (prepared by copolymerization of styrene and acrylic acid (carboxyl parking area 49.5 angstroms or 0.0934 milliequivalents/gm; prepared by Seradyn Inc., Indianapolis, Ind.) in 2.727 mL water was added dropwise to 3.0 mL of the hydroxypropylaminodextran solution while vortexing. Three hundred fifty eight (358) µL of EDAC solution (80 mg/mL) and MES (1.364 mL) in water was added to the coating mixture while vortexing. The mixture was incubated overnight at room temperature in the dark. The mixture was diluted with 7.5 mL water and centrifuged. The supernatant was discarded and the bead pellet was suspended in 12 mL of aqueous 1M NaCl by sonication. The beads were washed 3 times with 1M NaCl (12 mL per wash) by repeated centrifugation and suspension by sonication. The final pellet was suspended in 12 mL water.

3. Preparation of DLBAR-Beads (18)

Figure 8:
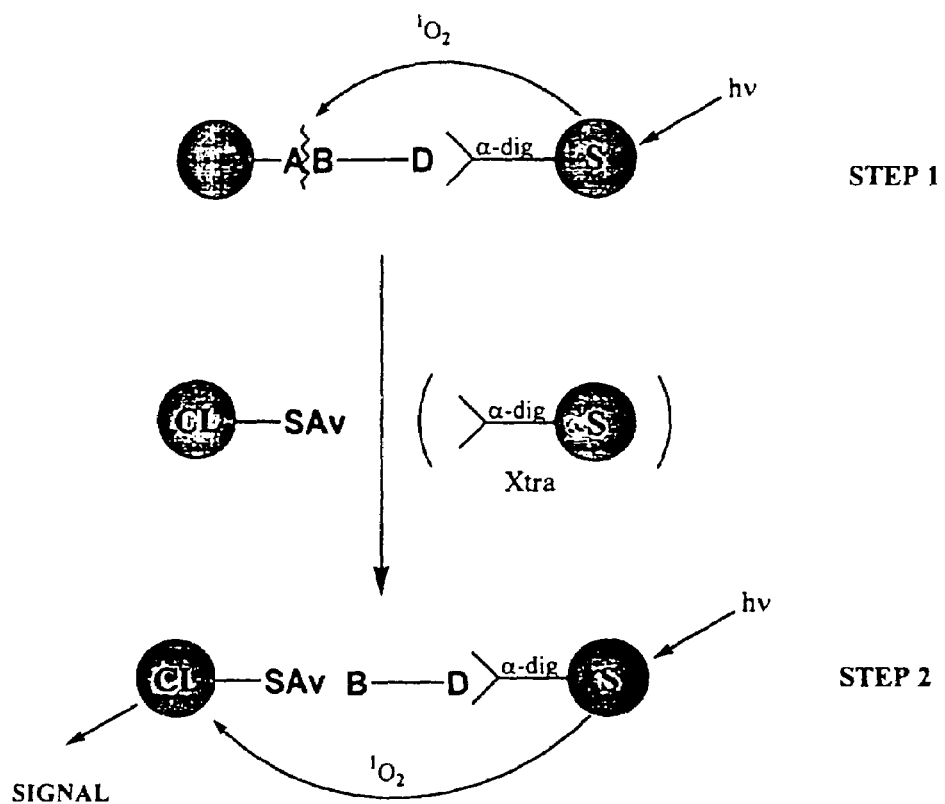
FIG. 8 illustrates oxidative cleavage and release of the DLB product from DLBAR beads (step 1) and the detection of the DLB product via LOCI sandwich assay (Example 6).
Figure 9:
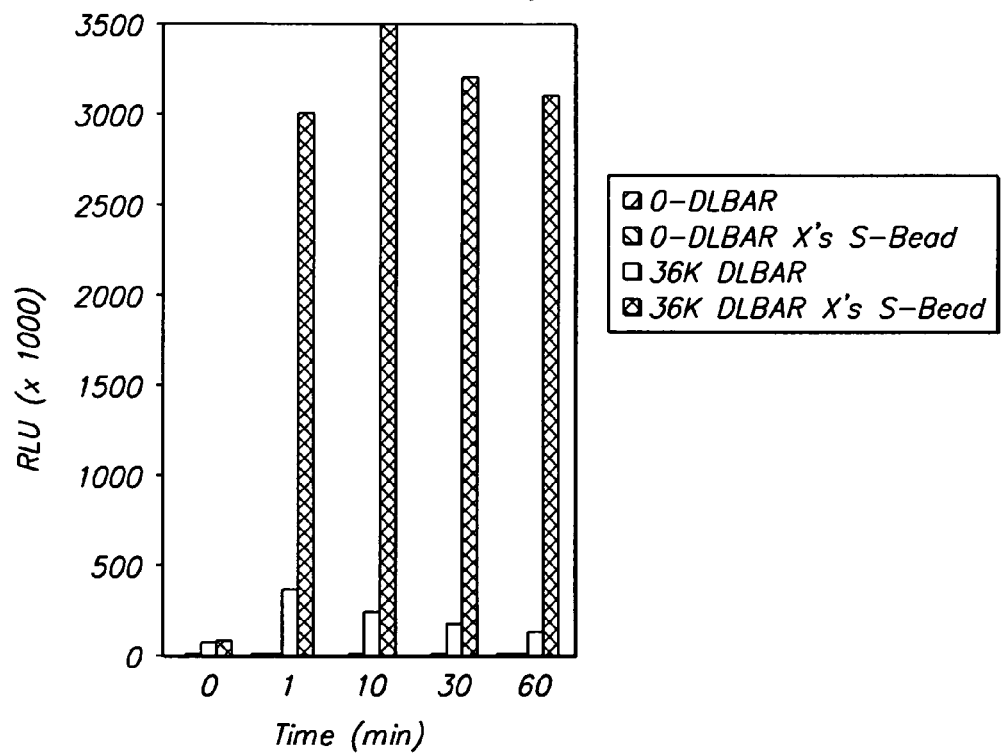
FIG. 9 illustrates DLB release from a bead pair LOCI sandwich assay (Example 6).
Figure 10A:
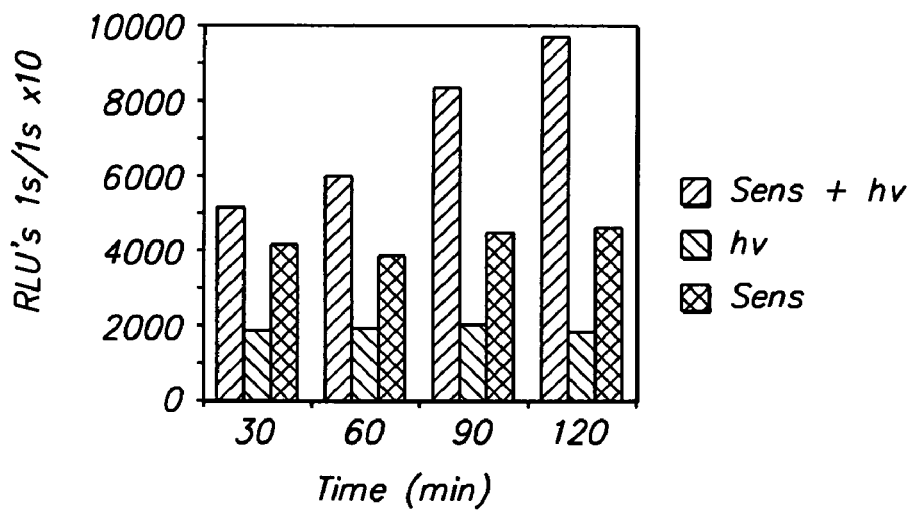
FIG. 10 illustrates detection of DLB product derived from oxidative deprotection of (a) $DLBAR-CO_2$-beads and (b) DLBAR-oligo-beads using a water soluble sensitizer. A LOCI sandwich assay using streptavidin sensitizer beads and chemiluminescer anti-dig beads (Example 5).

The appropriate amount of the DLBAR-CO$_2$NHS (16)/ DMF solution (prepared in Example 2, part 6 above) was added to six tubes, each containing 20 mg AmDxBeads (17) /1.00 mL 200 mM pH 7.55 phosphate buffer. The tubes were labeled A-F and contained, respectively: 0, 1000, 5000, 10000, 50000, and 100000 loadings of DLBAR molecules/ bead. The contents of each tube were mixed using a Vortex mixer, and the tubes were placed on a shaker table. After 72 h at ambient temperature, the contents of each tube was diluted with 2.00 mL of the buffer, mixed, and centrifuged at 16K rpm for $\geq$1 h. The clear colorless supernatants were decanted and saved for UV analysis. The beads were re-suspended in 3.00 mL buffer and the procedure was repeated two more times. The final set of beads was re-suspended in 2.00 mL of the buffer. The amount of free DLBAR in each decantate was measured by UV at 378 nm vs. a standard. The actual loadings of DLBAR/Bead were calculated by difference, and the results are displayed graphically in FIG. 6. The actual loadings calculated in this manner were 0, 750, 3250, 5400, 19500, and 36000 DLBAR molecules/bead, respectively. Bead sizes were measured by NICOMP and ranged between 234-244 nm (0.11-0.18 CVs), with no obvious correlation to the loading. The 36K load beads were used to test the release of Dig-Linked-Biotin from the beads by 102. This was confirmed by the soluble sensitizer method (see FIG. 10a and Example 5) and in a bead-pair LOCI assay (see Example 6 and FIGS. 8-10). The 0, 5.4K, and 19.5K beads were used in the preparation of DLBAR/Oligo-Beads.

Example 4

Preparation of Dig-Linked-Biotin-Anthracene-R/Oligo Beads (DLBAR/Oligo-Beads) (19) for Nucleic Acid Detection Amplification.

Figure 4:
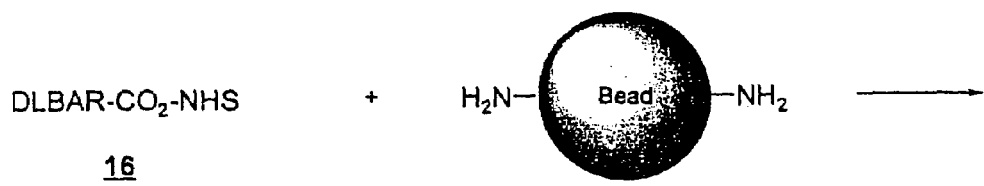
FIG. 4 illustrates DLBAR-oligo bead preparation and preparation for nucleic acid detection amplification.
Figure 4:
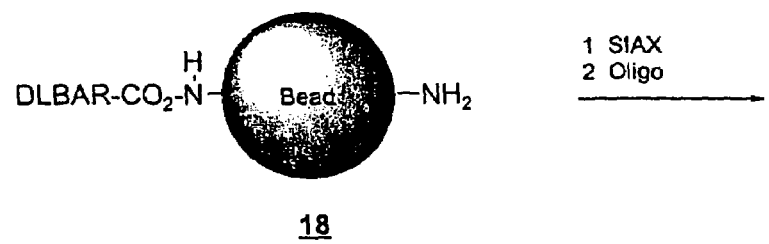
Figure 4:
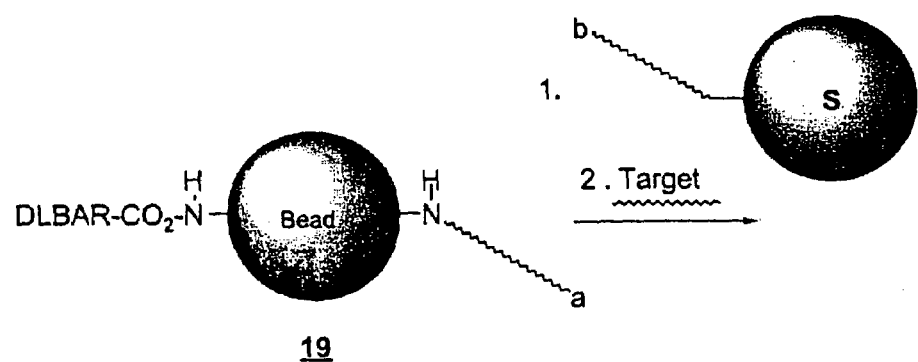
Figure 4:
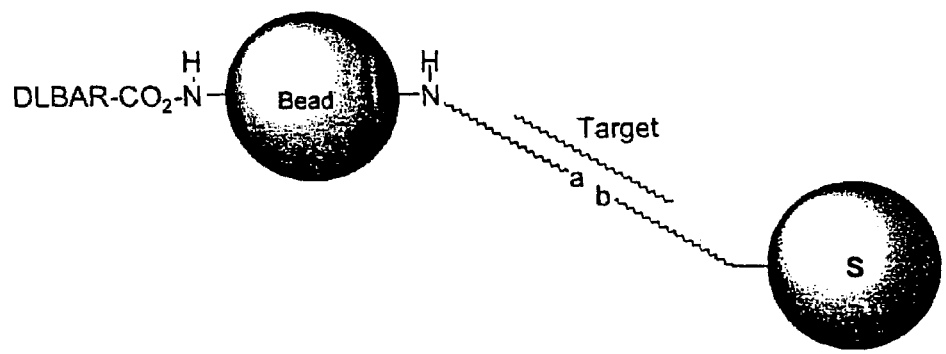

This Example describes the preparation of DLBAR beads conjugated with an oligonucleotide as illustrated in FIGS. 3 and 4.

$$\text{DLBAR-Beads} \xrightarrow{\text{oligo}} \text{DLBAR-Beads-Oligo}$$
$$\qquad\quad 18 \qquad\qquad\qquad\qquad 19$$

A typical method of attachment of oligonucleotides to DLBAR-beads is as follows:

Two hundred ninety five (295) mg of DLBAR-beads (prepared as described above) were suspended in 29.5 mL 50 mM MOPS pH 7.0. A 10% (w/v) SIAX solution was prepared in DMSO and 351 µL was added to the bead suspension while vortexing. The mixture as incubated at room temperature for an additional 90 minutes in the dark and then a second 351 µL aliquot of SIAX solution was added and the mixture was incubated for an additional 60 minutes. The suspension was centrifuged and the supernatant was discarded. The bead pellet was suspended in 14.75 mL water by sonication and the centrifugation repeated. The pellet was suspended in 7.375 mL water and stored at 4° C.

Any remaining amines were succinylated by adding 3.688 mL of 0.4 M borate, pH 9.45, followed by three aliquots of 165.8 uL succinic anhydride (100 mg/mL in DMSO). The tube was maintained at 37° C. for 45 minutes after each aliquot. Water (6 mL) was added and the beads were recovered by centrifugation. The beads were washed by centrifugation with 12 mL portions of 0.05 M MOPS (pH 7), 0.5 M NaCl, and water, then resuspended in 14.75 mL water and stored refrigerated.

In preparation for oligonucleotide coupling, a 150 uL (3 mg) portion of the beads was diluted to 1 mL with water, centrifuged, the supernatant was discarded and 1.34 mL coupling buffer was added to the pellet. Coupling buffer consists of the following mixture: 900 µL 0.2 M borate, 2 mM EDTA pH 9 and 333 µL of 0.4 M borate pH 9.45 and 1000 µL of 2 M sodium sulfate. The mixture was degassed and saturated with argon and then 9 µL of 10% Tween 20 detergent was added.

5'(AGTA)$_6$ (SEQ ID NO:3) oligonucleotide modified at the 3' end with —PO$_2$$^{-OCH}$$_2$CH$_2$CH$_2$SSCH$_2$CH$_2$CH$_2$OH was dissolved in water and the concentration was determined by optical density at 260 nm. Using the extinction coefficient supplied by the vendor, the concentration was found to be 476 nmoles/mL. Approximately 9.2 nmoles of oligonucleotide per mg of beads was used for the coupling procedure.

Oligonucleotide solution (89.7 µL) was placed in a centrifuge tube and 6.4 µL of 2.5 M sodium acetate pH 5.3 was added. TCEP (17.6 µL of 20 mM TCEP) in water was added to the oligonucleotide solution and the mixture was incubated for one hr at room temperature in the dark. Four volumes of 200 proof ethanol was added to the mixture to precipitate the reduced oligonucleotide. Precipitation was facilitated by placing the mixture in a minus 20° C.-freezer for 2 hours. The precipitate was collected by centrifugation and then dissolved in 30.1 µL of 5 mM sodium hydrogen phosphate, 2 mM EDTA pH 6 that had been degassed and saturated with argon. Brief sonication was necessary to hasten dissolution. Total volume was about 42 uL.

An aliquot of oligonucleotide solution (29 uL) was then added to the bead pellet under coupling buffer and the mixture was sonicated to suspend the beads. The suspension was incubated at 37° C. under argon for about 16 hours. Residual iodo groups of the iodoaminodextran coat were capped by reaction with mercaptoacetic acid. The bead suspension was centrifuged and the supernatant was reserved. The pellet was suspended by sonication in 9.9 uL of 10 mM mercaptoacetic acid in 0.4 M borate pH 9.45 and the mixture was incubated at 37° C. for 1 hr. The beads were diluted to 1 mL with water, recovered by centrifugation and were suspended in 1 mL blocking buffer (0.1 M sodium chloride, 0.17 M glycine, 10 mg/mL BSA, 0.1% Tween 20, 1 mM EDTA pH 9.2, sterile filtered and 50 µL/mL Calf Thymus DNA (Sigma, Cat. No. D8661 (10 mg/mL) was added). The mixture was incubated for 3 hr at 37° C. Following centrifugation the beads were washed twice by centrifugation with 1 mL of LOCI buffer (0.1 M Tris base, 0.3 M NaCl, 25 mM EDTA, 1 mg/mL Dextran T-500, 1 mg/mL BSA, 1:320 dilution of HBR-1 heterophile blocking reagent, 0.05% Kathon, and 0.01 M gentamycin, pH 8.2) per wash. The pellet was then washed once in 1 mL of IHBB (50 mM KCl, 10 mM TRIS, 4 mM magnesium chloride, and 0.02% acetylated BSA, pH 8.2). The final pellet was suspended in 0.3 mL IHBB.

Any loosely bound material was removed from the beads by adding nine volumes of LOCI buffer supplemented with 10 mM 1,3-Bis[tris(hydroxymethyl) methylamino]propane and with pH adjusted to 9.2. The beads were incubated in this mixture for 5 days at 55° C., then cooled. The mixture was centrifuged, the supernatant was discarded and the DLBAR/oligo-beads were washed twice by centrifugation with 1 mL aliquots of IHBB and was stored at 4° C. protected from light.

For comparison purposes, an alternative procedure for preparing DLBAR/oligo-beads was carried out where Bromoacetyl-NHS was used instead of SIAX (normally used for oligo attachment). In a side-by-side comparison, the 0, 5.4K and 19.5K DLBAR loaded beads (5 mg each tube) were used to prepare the two sets (SIAX vs. BrAc-NHS) of three loadings of DLBAR beads. A Fluorescence Depletion Assay (Example 7) on the oligo 19.5K (20K) DLBAR loaded BrAc-NHS derived beads (used in subsequent assays because of improved oligo loading) revealed an oligo loading of at least 20K oligo/per bead. These beads are referred to as (20K/20K) DLBAR/Oligo-Beads. The release of Dig-Linked-Biotin from these beads by $^1O_2$ was confirmed by the soluble sensitizer method (see Example 5 and FIG. 10b) and in a bead-pair LOCI assay (see Example 6 and FIG. 11). A portion (100 ug) of these beads was incubated with a large excess of target oligo and purified by repeated centrifugation/decantation. A Fluorescence Depletion Assay revealed that 15K target had bound to the beads.

Example 5

Measurement of Dig-Linked-Biotin (DLB) Release from DLBAR-Y Using a Soluble Sensitizer Method In this Example, oxidative cleavage of DLB from DLBAR-$CO_2$Me, DLBAR-beads and DLBAR Oligo-beads were measured in a signal amplification system that employed a water soluble sensitizer (Step 1) to generate the detectable bifunctional DLB product and a LOCI sandwich assay (Step 2) which utilized chemiluminescer anti-dig acceptor beads and streptavidin sensitizer beads to detect the product produced in Step 1. Preparation of DLBAR-$CO_2$Me (Example 2, part 4), DLBAR-beads (Example 3), and DLBAR Oligo-beads (Example 4) is described above. Preparation of the chemiluminescer anti-dig acceptor beads and streptavidin sensitizer beads are described below.

a. Chemiluminescer Anti-Dig Acceptor Beads

1. Preparation of Chemiluminescer Acceptor Beads

A 10% solution of carboxylated latex beads (120 mL) was heated to 93° C. in a three-neck round bottom flask, and then was mixed with 166 mL ethoxyethanol, 336 mL ethylene glycol, and 12 mL of 0.1 M NaOH. A mechanical stirrer and a thermometer were added and the mixture was brought to 95° C. with stirring and then was stirred for an additional 40 min. In a separate flanks, 2.45 g of C-28 thioxene, 191.8 mg of 2-chloro-9-10-bis(phenylethynyl) anthracene, and 323.9 mg of rubrene were mixed in 264 mL of ethoxyethanol and the mixture was heated to 95° C. with stirring until dissolved. The dye solution was poured into the bead solution and was stirred for 20 min. at 95° C. and then was allowed to cool slowly to about 47° C. and filtered through a 43 micron polyester filter. The beads were washed by tangential flow filtration using a Microgon apparatus with a 0.05 micron filter. After priming of the system with wash solvent (1:2 v/v ethoxyethanol:ethylene glycol), the dyed bead mixture was added. The mixture was concentrated to about 20 mg/mL and then was washed with 6 L of wash solvent and 4.8 L of 10% v/v ethanol in water adjusted to pH 10 with NaOH. The beads were concentrated to about 50 mg/mL during the wash, and then were finally stored at 4° C. protected from light. Final concentration was determined by weight after evaporating an aliquot to dryness.

2. Preparation of Double-Coated Chemiluminescer Acceptor Beads

A solution of 4 g of hydroxypropylaminodextran (prepared as described in Example 3) in 200 mL of 50 mM MES, pH 6±0.1 was subjected to Microgon filtration. To the filtered solution (150 mL) was added dropwise with stirring 150 mL of a 20 mg/ML suspension of chemiluminescer acceptor beads from above in 10% ethanol/water. Stirring was continued for 30 minutes with stirring to the above reaction mixture. The reaction mixture was protected from light and stirred overnight at room temperature.

A solution of dextran aldehyde (prepared as described in U.S. Pat. No. 5,929,049 which is incorporated by reference in its entirety) (10 g/200 mL 50 mM MES, pH 6±0.1) was subjected to Microgon filtration using a module of 0.2 micron rated pore size. To the filtered solution (100 mL) was added dropwise a previously sonicated 25 mL aliquot of a 20 mg/mL suspension of the chemiluminescer acceptor beads in 10 mM MES, 0.5 NaCl, pH 6. A total of 4 aliquots were added to the dextran aldehyde solution. Stirring was continued for 30 minutes. Then, a solution of 400 mg sodium borohydride in 10 mL water was added dropwise to the stirring bead mixture. The reaction mixture was protected from light and shaken at 37° C. for 40 to 60 hours. The beads were purified by Microgon washing.

2. Conjugation of Anti-Dig mAb to Double-Coated Chemiluminescer Acceptor Beads

Anti-digoxin monoclonal antibody (Catalog No. 2H6, Syva Inc., a subsidiary of Dade Behring Inc., Cupertino, Calif., USA) was then attached to the chemiluminescer beads. The bead reaction mixture was prepared in 1.5 ml microfuge tubes as follows. Reagents were added in the order and amounts as follows: 55 µl water, 50 µl 1 M MES (pH 6.0), 5 µl 10% Tween, 100 µl beads (100 mg/mL in aq. 10% ethanol solvent), 280 µl anti-digoxin mAb (100 ug/mL concentration in water) and 10 µl NaBH₃CN (0.6 mg/mL in water). Samples were vortexed after each addition. Thereafter, the beads were incubated in a rotary shaker at 37° C. and 100 oscillations/min. for 48 hr. After the incubation was completed, 20 µl 1.0 M CMO (water used as solvent) was added. The incubation was continued further at 4° C. overnight. The bead solution was then layered on a 7 ml bed of 7% sucrose in 1M Tris buffer (pH 8.0) containing 0.1% gentamycin. The anti-dig beads were then purified from unreacted beads by centrifugation at 12K and 10° C. for 30 min. The supernatants were removed from the pelleted beads with Pasteur pipettes. The pelleted beads were resuspended in 5 ml 100 mM Tris buffer pH 8.0, recentrifuged and the bead pellet was collected. An additional resuspension/centrifugation step was carried out. The purified bead pellet was resuspended (10 mg/mL) in 100 mM Tris buffer pH 8.0 and was stored at 4° C.

b. Preparation of Streptavidin-Coated Sensitizer Beads

1. Preparation of Silicon tetra-t-butyl phthalocyanine:

Sodium metal, freshly cut (5.0 g, 208 mmol), was added to 300 mL of anhydrous methanol in a two-liter, 3-necked flask equipped with a magnetic stirrer, reflux condenser, a drying tube and a gas bubbler. After the sodium was completely reacted, 4-t-butyl-1,2-dicyanobenzene (38.64 g, 210 mmol, from TCI Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr while the stream of ammonia gas continued during the course of the reaction, as solid started to precipitate. The resulting suspension was evaporated to dryness (house vacuum) and the residue was suspended in water (400 mL) and filtered. The solid was dried (60° C., house vacuum, P₂O₅). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical company) was added with a syringe to the stirred solution over a period of 10 minutes. After the addition was completed, the reaction mixture was heated to 180-185° C. in an oil bath for 1 hr. The reaction was allowed to cool to room temperature and concentrated HCl was carefully added to acidify the reaction mixture (pH 5-6). The dark brown reaction mixture was cooled and filtered. The solid was washed with 100 mL of water and dried (house vacuum, 60° C., P₂O₅). The solid material was placed in a 1-L, round bottom flask and concentrated sulfuric acid (500 mL) was added with stirring. The mixture was stirred for 4 hr at 60° C. and was then carefully diluted with crushed Ice (2000 g). The resulting mixture was filtered and the solid was washed with 100 mL of water and dried. The dark blue solid was transferred to a 1-L, round bottom flask, concentrated ammonia (500 mL) was added, and the mixture was heated and stirred under reflux for 2 hr, was cooled to room temperature and was filtered. The solid was washed with 50 mL of water and dried under vacuum (house vacuum, 60° C., P₂O₅) to give 12 g of product silicon tetra-t-butyl phthalocyanine as a dark blue solid. 3-picoline (12 g, from Aldrich Chemical Co.), tri-n-butyl amine (anhydrous, 40 mL) and tri-n-hexyl chlorosilane (11.5 g) were added to 12 g of the above product in a one-liter, three-necked flask, equipped with a magnetic stirrer and a reflux condenser. The mixture was heated under reflux for 1.5 hr. and then cooled to room temperature. The picoline was distilled off under high vacuum (oil pump at about 1 mm Hg) to dryness. The residue was dissolved in CH₂Cl₂ and purified using a silica gel column (hexane) to give 10 g of pure product di-(tri-n-hexylsilyl)-silicon tetra-t-butyl phthalocyanine as a dark blue solid. (LSIMS: [M−H]⁺ 1364.2, absorption spectra: methanol: 674 nm (ε180,000): toluene 678 nm, ¹H NMR (250 MHz, CDCl₃): δ: −2.4(m, 12H), −1.3(m, 12H), 0.2-0.9 (m, 54H), 1.8(s, 36H), 8.3(d, 4H) and 9.6 (m, 8H) was consistent with the above expected product.

2. Preparation of Silicon tetra-t-butyl phthalocyanine Sensitizer Beads

The sensitizer beads were prepared placing 600 mL of Seradyn carboxylate modified beads in a three-necked, round-bottom flask equipped with a mechanical stirrer, a glass stopper with a thermometer attached to it in one neck, and a funnel in the opposite neck. The flask had been immersed in an oil bath maintained at 94±1° C. The beads were added to the flask through the funnel in the neck and the bead container was rinsed with 830 mL of ethoxyethanol, 1700 mL of ethylene glycol and 60 mL of 0.1N NaOH and the rinse was added to the flask through the funnel. The funnel was replaced with a 24-40 rubber septum. The beads were stirred at 765 rpm at a temperature of 94±1° C. for 40 min.

Silicon tetra-t-butyl phthalocyanine (10.0 g) (prepared as described in Part 1 above) was dissolved in 300 mL of benzyl alcohol at 60±5° C. and 85 mL was added to the above round bottom flask through the septum by means of a syringe heated to 120±10° C. at a rate of 3 mL per min. The remaining 85 mL of the phthalocyanine solution was then added as described above. The syringe and flask originally containing the phthalocyanine was rinsed with 40 mL of benzyl alcohol and the rinse was transferred to the round-bottom flask. After 15 min 900 mL of deionized water and 75 mL of 0.1N NaOH was added dropwise over 40 min. The temperature of the oil bath was allowed to drop slowly to 40±10° C. and stirring was then discontinued. The beads were then filtered through a 43 micron polyester filter and subjected to a Microgon tangential flow filtration apparatus (Microgon Inc., Laguna Hills, Ca) using ethanol:water, 100:0 to 10:90, and then filtered through a 43 micron polyester filter.

3. Preparation of hydrazine-Coated phthalocyanine Sensitizer Beads

A 2.5 L suspension of phthalocyanine dyed sensitizer beads (6 mg/mL) in TAPS buffer (50 mM, pH 8.30) was prepared. Sensitizer beads (33 mg/mL) (455 mL) were added to 2.05 L of TAPS buffer contained in a three-necked 3.0 L round bottomed flask. The pH of the suspension was adjusted to 8.3 by addition of 0.1 N HCl or 0.1 N NaOH. The suspension was stirred at 350-400 rpm and 75 mL of TAPS containing 0.6 mL of hydrazine was added. STUT (6.0 g) (O-(N-succinimidyl)-N,N,N',N'-tetramethyluronium tetrafluoroborate, (Fluka) was added slowly to the above mixture in four equal aliquots dissolved in 8 mL of DMSO at 15 minute intervals. The pH of the mixture was adjusted to 8.30 after each addition of an aliquot. The mixture was stirred at room temperature for an additional 2 hr after addition of the last aliquot. The beads were purified by Microgon® tangential flow separation using a MiniKros lab system filter (Catalog No. Syls 12101N) molecular weight cut-off filter, washing with LOCI buffer. The washed beads were stored in aqueous 10% ethanol solution.

A filtered dextran aldehyde solution (275 mL, 40 mg/mL, 11.0 g) was transferred to a 3-necked, round bottom flask and a 20 mg/mL (275 mL) suspension of the beads prepared above in water was added dropwise to the stirring dextran aldehyde solution. The pH of the reaction mixture was adjusted to 5.0 if necessary. The reaction mixture was stirred for an additional 30 minutes and then was transferred to a 1.0 L glass bottle and was shaken for 17 hr. at 50° C. The beads were washed by Microgon® tangential flow separation using a Mini Kros Lab System filter (Syls 12101N), washing with LOCI buffer. The washed beads were stored in aqueous 10% ethanol solution.

4. Attachment of Streptavidin to hydrazine-Coated Sensitizer Beads

A solution of streptavidin (Boehringer Mannhein, Indianapolis, Ind.) at 10-12 mg/mL (75-62.5 mL) in a sodium acetate (Aldrich Chemical Co., St. Louis, Mo., USA) buffer (pH 5.0, 0.2 M) was prepared and the beads prepared above were added slowly with stirring to the solution at 19.0 mg/mL (79 mL). The reaction mixture was stirred for 30-60 minutes. A solution of sodium cyanoborohydride (15 mg/mL) in water was added to the above reaction mixture and the pH was adjusted to 5.0. The reaction container was covered with aluminum foil and shaken at 100-150 rpm at 37° C. for 48-60 hrs. To this reaction medium was added 2.0 mL of a 1.0 M solution of CMO at pH 5.0 prepared by adding 10 N sodium hydroxide to 2.19 g of CMO hemihydrochloride dropwise. The reaction medium was incubated at 37° C. for 4-8 hr and the particles were washed by Microgon.

C. Detection of DLB Cleavage Products Via Amplified Homogeneous LOCI Assay

As an example of a typical procedure, DLBAR-$CO_2$Me (0.10 mg) was dissolved in 1 mL DMF. This solution was added to 7.0 mL LOCI buffer and mixed by Vortex giving a 10 uM solution. A portion of this solution (2.00 mL) was added to each of three glass tubes labeled: A, B, and C. Water soluble sensitizer (100 uL, 1 uM AlPc$(SO_3)_4$ ("aluminum phthalocyanine tetra sulfonate") in LOCI buffer was added to tubes A and C and the mixture was vortexed. 100 uL of LOCI buffer was added to tube B. Following removal of 50 uL aliquots ($T_0$) from each of the three tubes, tubes A and B were simultaneously illuminated using a Dolan-Jenner lamp with a 610 nm cutoff filter. Aliquots were removed from each of the three tubes at: 10, 30, 60, 90, and 120 min. Chemiluminescer anti-dig beads (100 uL, 100 mg/mL LOCI buffer) and Sensitizer-Streptavidin beads (100 uL, 100 mg/mL LOCI buffer) were added to each of the tubes. The contents of each tube were diluted with 1.00 mL LOCI buffer, and the tubes were Vortexed and then incubated at 37° for 30-60 min. LOCI readings (1 sec illumination 680 nm/1 sec read) furnished the data that is shown graphically in FIG. 7. All of the graphs referred to in the synthesis section were roughly comparable.

For DLBAR-beads, the same procedure was followed except 1.0 mg (100 uL of 10 mg/mL) DLBAR-beads were used (see FIG. 10).

Figure 10B:
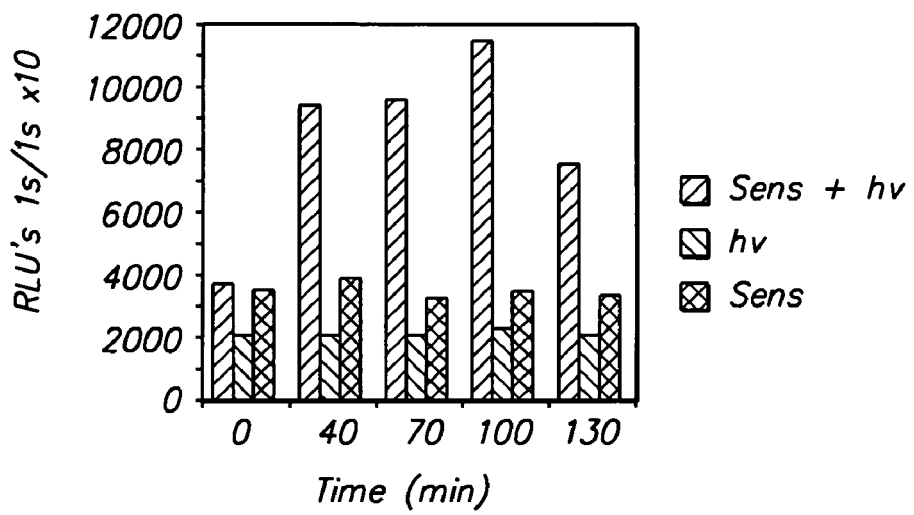
Figure 11:
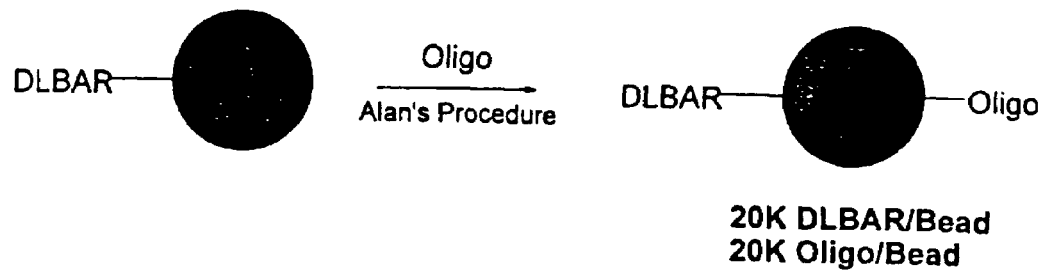
FIG. 11 illustrates (a) preparation of DLBAR/oligo beads and (b) DLB release from DLBAR oligo beads using methylene blue as sensitizer.
Figure 11:
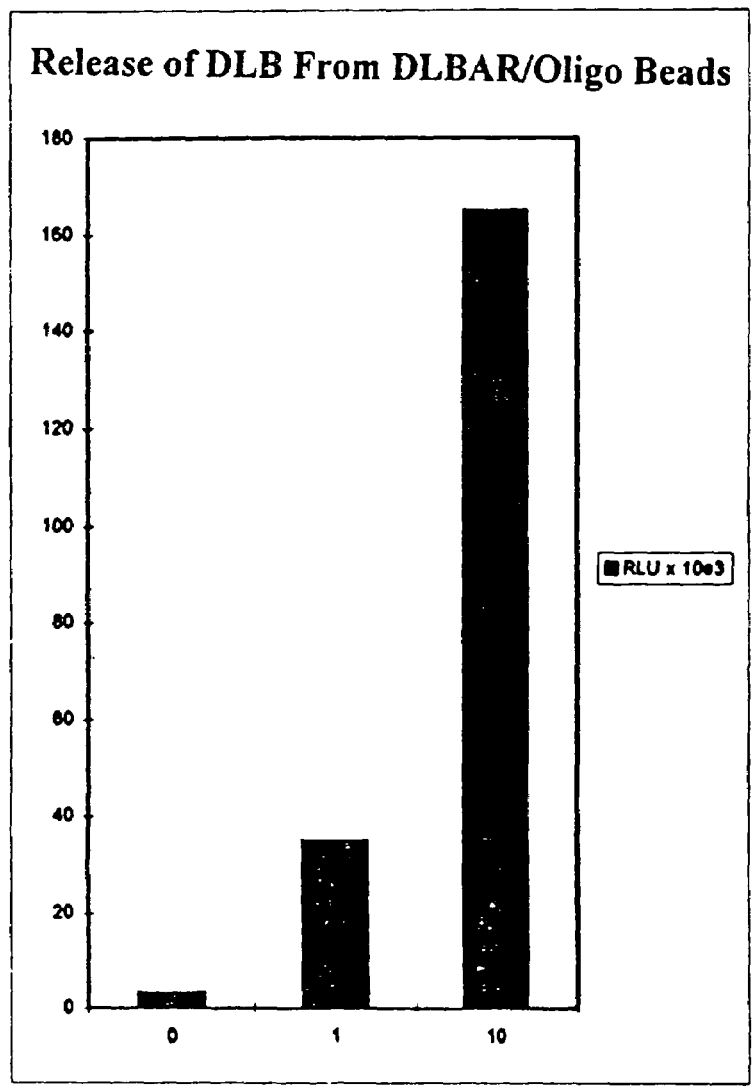

For DLBAR/Oligo-beads, the same procedure was followed as for DLBAR-beads except methylene blue was used as the soluble sensitizer (to enhance charge interactions with the oligo) (see FIG. 10*b*).

Example 6

Measurement of Dig-Linked-Biotin (DLB) Release From DLBAR-beads Using a Bead Pair LOCI Assay.

In this Example, product DLB from the oxidative cleavage of DLBAR-beads was measured by a LOCI sandwich detection assay that employed sensitizer beads (step 1) to generate the detectable bifunctional DLB product. Then a LOCI sandwich assay (step 2) which utilized chemiluminescer anti-dig acceptor beads and streptavidin senstizer beads was used to detect the product produced in Step 1. Preparation of DLBAR beads (Example 3), chemiluminescer anti-dig acceptor beads (Example 5) and streptavidin sensitizer beads (Example 5). This Example is a repeat of Example 5, however, the sensitizer beads conjugated to anti-dig mAb were used in both steps 1 and 2. See FIGS. 8 and 9 for an illustration of the procedure and results.

a. Preparation of Single Coated Anti-Dig Sensitizer Beads

1. Preparation of Hydroxypropylaminodextran-Coated Sensitizer Beads

A solution of hydroxypropylaminodextran (synthesized as described above) was prepared at 100 mg/mL in 50 mM MES (pH 6). The pH was re-adjusted to 6 with 1M HCl. Three hundred (300) mg phthalocyanine sensitizer beads (synthesized as described above) in 2.727 mL water was added dropwise to 3.0 mL of the hydroxypropylaminodextran solution while vortexing. Three hundred fifty eight (358) μL of EDAC solution (80 mg/mL) and MES (1.364 mL) in water was added to the coating mixture while vortexing. The mixture was incubated overnight at room temperature in the dark. The mixture was diluted with 7.5 mL water and centrifuged. The supernatant was discarded and the bead pellet was suspended in 12 mL of aqueous 1M NaCl by sonication. The beads were washed 3 times with 1M NaCl (12 mL per wash) by repeated centrifugation and suspension by sonication. The final pellet was suspended in 12 mL water.

2. Attachment of Anti-Dig mAb to hydroxypropylaminodextran-Coated Sensitizer Beads Anti-digoxin monoclonal antibody (catalog No. 2H6, Syva Co., Cupertino, Calif.) was then attached to the above sensitizer beads. The bead reaction mixture was prepared in 1.5 ml microfuge tubes as follows. Reagents were added in the order and amounts as follows: 55 μl water, 50 μl 1 M MES (pH 6.0), 5 μl 10% Tween, 100 μl beads (100 mg/ml in aqueous 10% ethanol), 280 μl anti-digoxin antibody (100 ug/mL in water) and 10 μl NaBH$_3$CN (0.6 mg/mL in water). Samples were vortexed after each addition. Thereafter, the beads were incubated in a rotary shaker at 37° C. and 100 oscillations/min. for 48 hr. After the incubation was completed, 20 μl 1.0 M carboxymethoxylamine (CMO) in water was added. The incubation was continued further at 4° C. overnight. The bead solution was then layered on a 7 ml bed of 7% sucrose in 1M Tris buffer (pH 8.0) containing 0.1% gentamycin. The anti-dig beads were then purified from unreacted beads by centrifugation in a Sorvall centrifuge (Dupont Corp., Newtown, Conn., USA) at 12K and 10° C. for 30 min. The centrifuge tubes used were Oak Ride centrifuge tubes by Nalge Co., Rochester, N.Y., USA. The supernatants were removed from the pelleted beads with Pasteur pipettes. The pelleted beads were resuspended in 5 ml 100 mM Tris buffer pH 8.0, recentrifuged and the bead pellet was collected. An additional resuspension/centrifugation step was carried out. The purified bead pellet was resuspended (10 mg/mL) in 100 mM Tris buffer pH 8.0 and was stored at 4° C.

b. Procedure

As an example of a typical procedure, (step 1) DLBAR-beads (prepared as described above) (0.5 mg, 50 uL of 10 mg/mL, 0 and 36K loadings) were washed by diluting with 2.0 mL LOCI buffer, then centrifuging at 16K rpm, decanting, and resuspending in 2.50 mL LOCI buffer. Aliquots (0.50 mL of each loading) were transferred to pairs of polypropylene LOCI tubes. Aliquots (0.1 mg, 20 uL of 5 mg/mL 100 mM pH 8.0 Tris buffer) of a freshly washed suspension of single coated anti-dig sensitizer beads were added to each of the tubes (Vortex). Note that this "reverse" set of anti-dig sensitizer beads was prepared specifically because of the nature of this experiment. Standard LOCI conditions use streptavidin sensitizer beads because antibody may be damaged when connected directly to the $^1O_2$ source.

The tubes were incubated at 37° for 1 h, and the contents of each tube was diluted with 1.00 mL of IHBB (in house buffer). A 100 uL $T_o$ sample was removed from each tube, and 100 uL aliquots were removed following illumination for 1, 10, 30, and 60 min using a Dolan-Jenner lamp with a 610 nm cut off filter.

In step 2, a 10 ug portion of the sensitizer beads was added to one set of the tubes and 10 ug (10 uL of 1 ug/uL LOCI buffer) of chemiluminescer Streptavidin beads were added to each of the tubes. Note that this second addition of anti-dig sensitizer was to replace antibody beads that may have been damaged by 102 in the first LOCI event (see FIG. 9).

The tubes were vortexed, incubated at 37° for 40 min, cooled, and diluted with 1.00 mL of LOCI buffer. After vortexing and equilibrating the tubes at 37° for 30 min, the LOCI signal was read. The data is displayed graphically in FIG. 9. By comparing to a calibration curve, the signal could be translated into DLB release per bead. In this case about 500 DLB were released per bead. The detection threshold is limited by LOCI reader (~$3.5 \times 10^6$) and is limited by the number of capture beads per tube.

Example 7

Fluorescence Depletion Analysis.

In this Experiment, a fluorescence labeled oligonucleotide target was incubated with DLBAR oligo-bead and the amount that was bound was determined by fluorescence difference. DLBAR-AGTA-beads (as representative DLBAR-oligo beads) were prepared as described in Example 4 using AGTA as oligomer. Labeled targets fluorescene-TATC ("F-TATC") and fluorescene-TACT ("F-TACT") were purchased from Oligo, etc., Wilsonville, Oreg., USA.

a. Materials Used

F-TATC: 13.4 uL (2 ug/tube) (Control).

F-TACT: 13.4 uL (2 ug/tube).

DLBAR-beads: 5 uL/1 ug of diluted suspension of 20K DLBAR loaded (Control).

Amt./tube: 0.50, 1.00, 2.00, 4.00, 8.00 ug beads. Four sets of tubes (duplicates for each of the two fluorescent probes).

DLBAR/Oligo-beads: 5 uL/1 ug of diluted suspension of 20K DLBAR loaded.

Amt./tube: 0.50, 1.00, 2.00, 4.00, 8.00 ug beads. Four sets of tubes (duplicates for each of the two fluorescent probes).

No beads control F-TACT and F-TATC (duplicates).

Buffer blank (duplicates).

b. Procedure

The appropriate ingredients were added to each of the 46 tubes, vortexed, and incubated at 55° for 1 h. The contents of each tube was diluted with 900 uL of LOCI buffer, vortexed, and centrifuged. A 750 uL aliquot from each tube was diluted with 500 μL LOCI buffer, vortexed, and the fluorescence was read. There was no depletion with the DLBAR-beads, and no depletion with F-TATC. The oligo substitution was calculated at half height of the depletion curve (bound F-TACT vs. ug beads). The result was that the loading of oligo (5'-AGTA-bead) was at least 20,000/bead. These beads were designated: (20K/20K) DLBAR/Oligo-Beads.

Example 8

Figure 5:
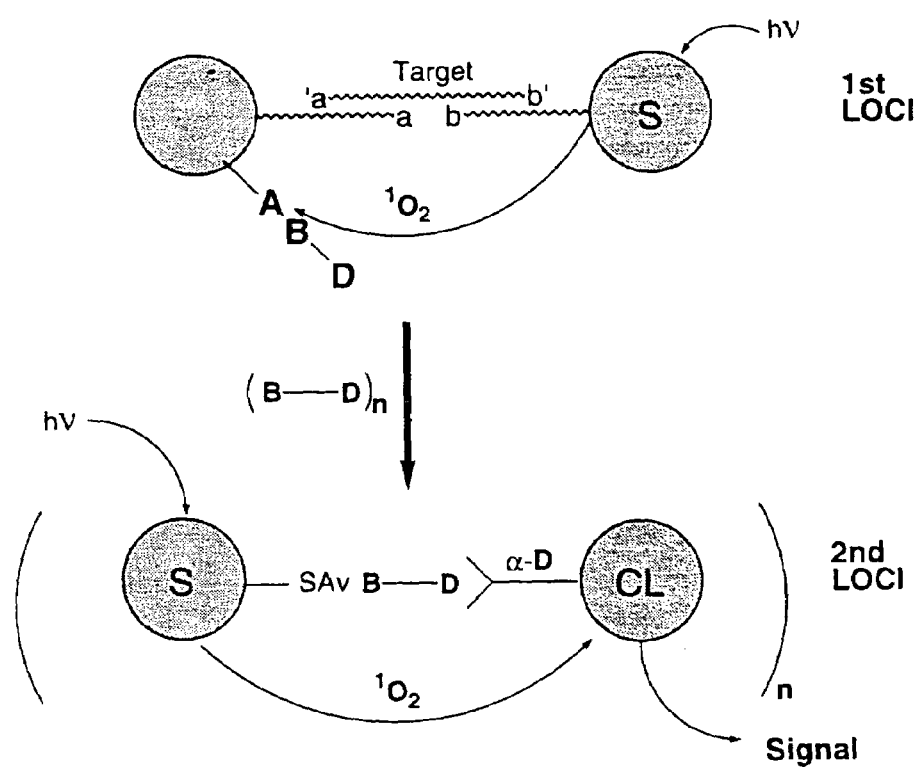
FIG. 5 illustrates a process for signal amplification involving (step 1) target bridging and formation of a detectable product $(B-D)_n$ and (step 2) detection of $(B-D)_n$ by a LOCI sandwich assay.
Figure 12:
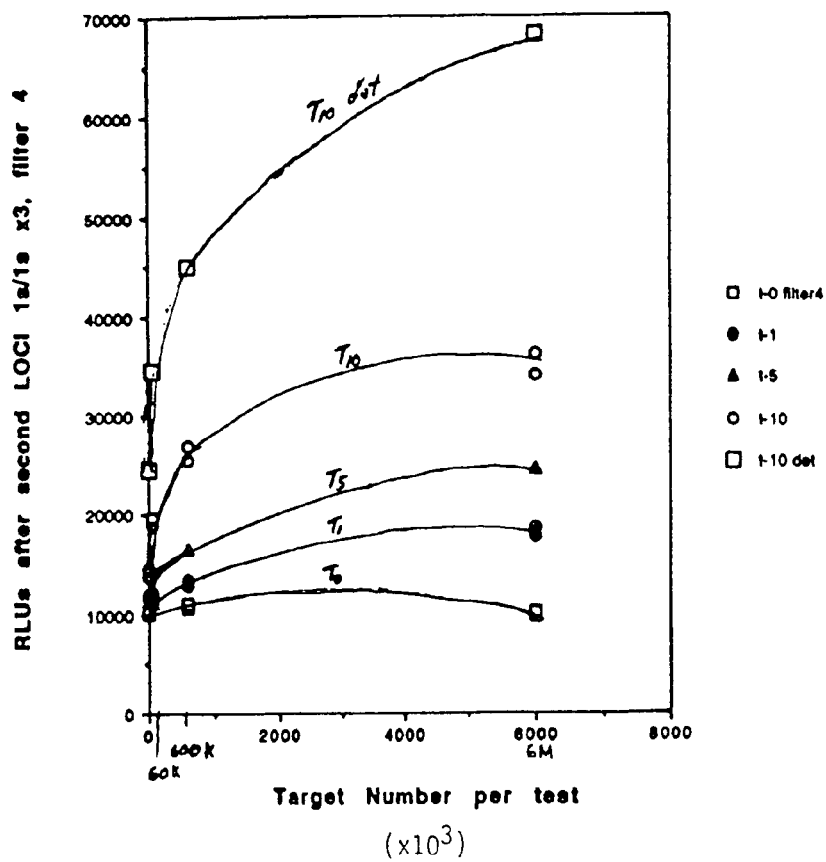
FIG. 12 illustrates (a) amplified LOCI detection of an $(TACT)_6$-XX-(dT)24 target polynucleotide and (b) illustrates formation of a product DLB following target molecule bridging (step 1) and detection by a LOCI sandwich assay (step 2) (Example 8).
Figure 12:
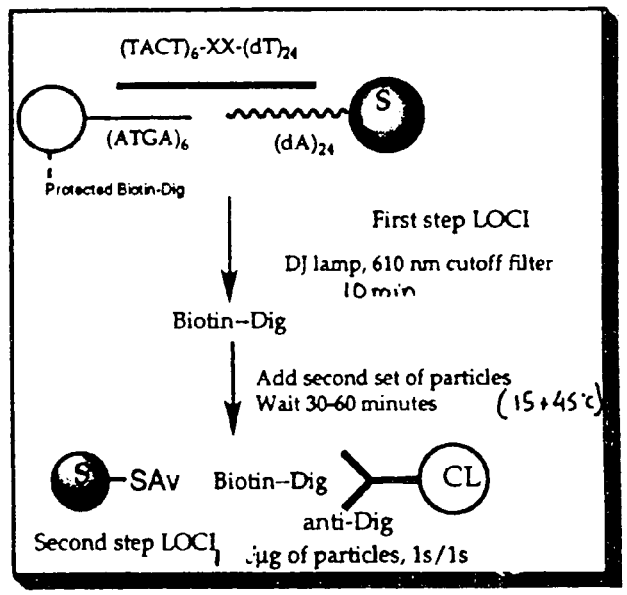

Amplified LOCI Assay Using a Single Tube Single Instrument Nucleic Acid Detection Amplification Format In this Example, detection of a target polynucleotide was accomplished by (step 1) generating a DLB product produced by the oxidative cleavage of DLBAR oligo beads in the presence of a sensitizer and (step 2) detecting the product using a sandwich detection assay, e.g., LOCI assay. The assay was carried out for a target single stranded oligonucleotide, $(TACT)_6$-$(GAT)_4$-$(dT)_{24}$ (SEQ ID NO:2). For step 1, DLBAR-$(AGTA)_6$(SEQ ID NO: 3)-bead, prepared as described in Example 4 except that $(AGTA)_6$ (SEQ ID NO:3) was used in the precursor form of 5'-$(AGTA)_6$—$PO_2$—$(CH_2)_2$ $CH_2SS(CH_2)_2CH_2OH$. $(dA)_{24}$-sensitizer (SEQ ID NO: 1) beads (also prepared as described in Example 4) were used. For step 2, target detection was achieved by measuring DLB product by bead pair LOCI assay which employs chemiluminescer anti-dig acceptor beads (prepared as described in Example 6) and streptavidin sensitizer beads (described in Example 5). The procedure and experimental results are shown in FIG. 5 and FIG. 12, respectively.

A typical procedure for LOCI amplification using a single tube single instrument nucleic acid detection amplification format is as follows: For step 1, washed DLBAR/Oligo$_a$-beads (1 ug in 10 uL IHBB (Note that IHBB=40 m$\underline{M}$ tris pH8, 4 m$\underline{M}$ MgCl$_2$, 70 m$\underline{M}$ KCl, 200 ug/mL Ac-BSA) and Sensitizer/Oligo$_b$-beads (1 ug in 10 uL IHBB) were combined, mixed, and incubated with target oligo (measured in molecules or attomoles, in 10 μL IHBB) in a 1 cc polypropylene LOCI tube. After incubation for 2 h at 55° C., the tubes were irradiated (LOCI strip tube 680 nm laser, or a Dolan-Jenner lamp with a 610 nm cutoff filter) for 0-30 min (usually <5 min). In step 2, a second set of sensitizer and acceptor beads (1 ug each in 50 uL total volume of LOCI buffer) was added, the mixture was incubated for 30-60 min, irradiated, and read (1 s/1 s for 3 cycles).

In step 1, the target polynucleotide, DLBAR-oligo beads, and sensitizer oligo beads were combined. The target molecules bound to the sensitizer particles and acceptor particles, bridging and drawing the sensitizer and acceptor particles into close proximity. Irradiation of the particle suspension at 680 nm produced singlet oxygen from the sensitizer contained in the sensitizer particles. This singlet oxygen reacted primarily with substrate that was attached to the acceptor particles, causing digoxigenin-biotin conjugate (DLB) to be released as product.

A step 2 LOCI sandwich assay was used for the detection of the released biotindigoxigenin conjugate. The assay was carried out by adding chemiluminescent beads conjugated with anti-digoxigenin mAb and sensitizer particles conjugated with streptavidin. The anti-dig mAb and steptavidin functionalities bound to the digoxin and biotin functionalities of DLB, bridging and drawing the sensitizer and acceptor beads into close proximity. After binding, the suspension was irradiated again and the chemiluminescence was measured. Whereas about $5 \times 10^5$ molecules of the target could be detected when the chemiluminescence was monitored from the first irradiation, as few as 60,000 molecules were detectable by measuring the chemiluminescence from the biotin-digoxigenin bound particle pairs.

Example 9

Enhanced Loci Homogeneous Immunoassay for the Detection of Oligonucleotides

This example essentially repeats Example 8, however, the oxidative cleavage of DLBAR was achieved with lactoperoxidase (Sigma, 108 units/mg of protein) which is conjugated to polynucleotide $(dA)_{24}$(SEQ ID NO:1). This conjugate was prepared and purified according to the procedure of Miller (EP 0185547 A2 and EP 0185547 B1) purified.

In step 1, DLBAR-$(AGTA)_6$(SEQ ID NO:3)-beads (10 ug in 100 uL of IHBB2X buffer (IHBB 2X=40 mM tris pH8, 8 mM MgCl2, 140 mM KCl, 400 ug/mL Ac-BSA) and the polynucleotide labeled lactoperoxidase (10 uL of 1.6 nmol/ml solution in 40 mM tris buffer pH 8) are mixed in each of two 1 CC polypropylene LOCI tube. To one of the tubes is added a solution of synthetic target polynucleotide $(TACT)_6$-$(GAT)_4$-$(dT)_{24}$ (SEQ ID NO:2) (10.0 uL of 0.16 nM in 40 mM tris buffer pH 8). Both the tubes are then incubated for 2 h at 55° C. To each of the tubes is then added a solution of hydrogen peroxide in tris buffer (100 ul of 1.0 uM) and 100 uL of 1.0 mM solution of sodium bromide in DI water. Aliquots of 20 uL are removed from each of the tubes at time 0, 10, 30, 60, 120, 180 and 360 minute intervals and added to a tube containing 2 uL of sensitizer Streptavidin beads (1 ug/uL in LOCI buffer) and 2 uL chemiluminescer anti-dig (1 ug/uL in LOCI buffer). In step 2, to each tube is then added LOCI buffer (1.0 mL), incubated at 37° C. for 4 hours, irradiated and read. The expected LOCI signals at the aforementioned time intervials are as follows:

|  | Time (min.) | | | | | | |
| --- | --- | --- | --- | --- | --- | --- | --- |
|  | 0 | 10 | 30 | 60 | 120 | 180 | 360 |
| Tube (control) RLU | 6000 | 6700 | 7100 | 7600 | 7700 | 8400 | 10400 |
| Tube (sample) RLU | 6500 | 7000 | 8000 | 9500 | 12200 | 14450 | 16100 |

Example 10

Enhanced LOCI Homogeneous Immunoassay for the Detection of Antigen HbsAg

In this Example, enhanced detection of minute quantities of HbsAg target was accomplished by (step 1) generating a DLB product produced by the oxidative cleavage of an amino-modified DLBAR (20) in the presence of a sensitizer and (step 2) detecting the product using a sandwich detection assay, e.g., LOCI assay. The assay was carried out for HbsAg as a target molecule.

Preparation of Amino-Modified DLBAR (20)

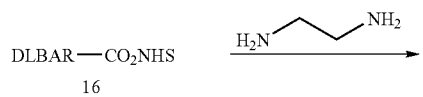

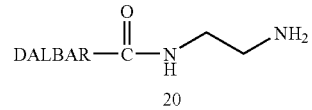

20

A solution of DLBAR-$CO_2$NHS (16) (2 mg, 1.7 mmol) in THF (0.5 ml) as described before, was added to a solution of 1,2 diamino ethane (2 mg, 34 mmol) in THF (1 ml). The reaction mixture was stirred for 4 hrs at room temperature. TLC (silicagel, MeOH:$CH_2Cl_2$, 5:95) indicated that all the NHS ester was consumed. The solvent was evaporated to dryness under vacuum and the residue was then dissolved in methanol (0.2 ml) and purified on a PTLC plate (MeOH: $CH_2Cl_2$, 10:90) to give 1.9 mg of the pure product as pale yellow solid.

Detection Procedure

For step 1, an amino-modified DLBAR (20) is attached to a N-oxysuccinimide surface and HbsAg monoclonal antibodies are conjugated to the DLBAR beads. Sample solution containing target HbsAg was then added, followed by lactoperoxidase labeled with HbsAg monoclonal antibodies. After incubation, hydrogen peroxide and sodium bromide was added to the solution and the resulting solution was incubated. The target molecule bound to the DLBAR bead and conjugated mAb, bridging and drawing the DLBAR bead and lactoperoxidase into close proximity. Hydrogen peroxide/sodium bromide produced an oxidant that reacted primarily with the DLBAR substrate attached to the beads, causing DLB to be released as product.

For step 2, target detection was achieved by measuring DLB product by bead pair LOCI assay which employs chemiluminescer anti-dig acceptor beads (prepared as described in Example 6) and streptavidin sensitizer beads (described in Example 5).

A typical procedure for the enhanced detection of minute quantities of HbsAg is described using a LOCI detection assay is as follows: Eight different samples of hydrazine modified Dig-biotin-anthracene and DMSO are prepared. The concentration of each sample is 0.0 ng/ml, 1.0 ng/ml, 10.0 ng/ml, 100.0 ng/ml, 500.0 ng/ml, 800.0 ng/ml, 1.0 ug/ml and 2.0 ug/ml of the amino modified DLBAR 20 respectively. To eight wells of a Costar' Amine Binding Plates and Strips (Costar Inc., catalog # 2506, having N-oxysuccinimide surface) are added 100 ul of the above samples respectively. The wells are incubated for 2 hours at room temperature and were decanted and rinsed 3 times with PBS and 0.1% Tween-20 buffer. The wells are then blocked with 200 ul solution of ethanolamine (0.5 mg/ml in PBS buffer pH 9.0) for one hour and then are rinsed 3 times with PBS buffer. 200 ul aliquots of HbsAg monoclonal solution (1 mg/mL mab in 100 mM acetate buffer, pH 6.0)(Dade Behring Inc., Malburg, Germany, Catalog No. 85-67/107) are added to the wells and incubated overnight at 4° C. The wells are then decanted and rinsed 3 times with the acetate buffer. The other pairs of HBsAg monoclonal antibody (Dade Behring, Inc., Malburg, Germany, Catalog No. 85-70/32) are labeled with lactoperoxidase and purified using the procedure of Pene and Arends (Pene, J. et al, *Biochem. Int'l*, Vol. 13, p. 233 (1986) and Arends, J. et al, *J. Immunol. Meth.*, Vol. 25, p. 171,). The mAb conjugate is stored in HbsAg LOCI buffer (0.1 M Tris base, 0.3 M Na Cl, 25 mM EDTA, 0.1% BSA (RIA grade), 1% Dextran T 500, 7.5 ppm Proclin 300, 0.01% (w/v) Gentamicin and 0.1% Zwittergent 3-14. PH 8.2).

An aliquot (26 ul) of a positive HBsAg sample (Dade Behring, Inc., Malburg, Germany Catalog No. 437905) is diluted to 100 ul with HBsAg LOCI buffer and then is added to the eight wells and incubated for 30 minutes at 4° C. The wells are decanted and rinsed once with the HBsAg buffer. The lactoperoxidase-HBsAg antibody conjugate solution (100 ul, 0.1 mg/ml) is then added to the wells and incubated for one hour at 4° C. The wells are decanted and washed 3 times with the LOCI buffer. To each wells is then added a solution of hydrogen peroxide in tris buffer (100 ul of 1.0 uM) and 100 ul of sodium bromide (1.0 mM in DI water). The wells are incubated for 30 minutes. Aliquots of 50 ul are removed from each well and added to a tube containing 2 ul of sensitizer Streptavidin beads (1.0 ug/ul in LOCI buffer) and 2 ul chemiluminescer anti-dig beads (1.0 ug/ul in LOCI buffer). To each tube is then added one ml of LOCI buffer and incubated at 37° C. for 4 hours. The expected LOCI signals at the aforementioned time intervals are as follows:

| Compound 12 (ng/ml) | 0 | 1 | 10 | 100 | 500 | 800 | 1000 | 2000 |
|---|---|---|---|---|---|---|---|---|
| RLU | 4000 | 4200 | 4500 | 5000 | 5400 | 5500 | 5700 | 5800 |

Example 11

Reversible Coupling of Oligonucleotides

This Example describes the attachment of oligonucleotides to a surface via a cleavable linker and release of the oligonucleotide from the surface.

(a) Preparation of a Sensitizer Bead Conjugated to a Sulfhydrylated Oligonucleotide The sulfhydrylated oligonucleotides used in this Example were purchased from Oligos, Etc. (Wilsonville, Oreg., USA). The oligos included mixed disulfides attached to the 3' end by conventional phosphoramidite chemistry. The structure of the oligo modified 3' end is as follows: Oligo-OPO$_2$—O(CH$_2$)$_3$ SS(CH$_2$)$_3$OH.

3' modified oligos (dA)$_{24}$ (SEQ ID NO: 1) covalently coupled on the sensitizer beads (prepared as described in Example 1) were labeled with gamma $^{32}$P ATP using the following procedure. The kinase reaction consisted of 2.5 ul of 10× kinase buffer (Stratagene, San Diego, Calif.), 2 uL of T4 polynucleotide kinase (Stratagene), 10 uL of $^{32}$P ATP (6000 Ci/mmol, from NEN), 5 uL of oligo beads (10 pmoles oligos on the beads) and 5.5 uL of deionized water. The reaction was carried out for 70 munutes at 37° C. The beads were then washed four times in 500 uL of IHBB buffer containing 10 mM Tris HCl pH 8.2, 50 mM KCl, 4 mM EDTA and 0.2 mg/mL acetylated BSA (Gibco BRL). The washing was carried out by centrifugation of the labeled beads in the above buffer for 45 minutes. The beads were resuspended in the buffer with brief sonication. The final wash was performed after storing the labeled beads overnight at 4° C. and centrifugation the next day. The final bead pellet was resuspended in a total of 100 uL of IHBB buffer and stored at 4° C. Two separate oligo bead preparations were labeled using the above protocol (dA$_{24}$) (SEQ ID NO:1) and (dA$_{40}$) (SEQ ID NO:7) stored at 4° C. Two separate oligo bead preps were labeled using the above protocols for dA$_{24}$ (SEQ ID NO: 1) and dA$_{40}$ (SEQ ID NO: 7).

(B) Singlet Oxygen Cleavage of Thioether Linkage

To determine the effect of 680 nm light on the sensitizer beads, 0.5 ug of oligo beads spiked with labeled beads was respended in a total of 50 uL of IHBB buffer containing 5 ug/mL calf thymus DNA (Sigma). The reactions were covered with 25 uL of mineral oil (Aldrich) and treated under various conditions. A control tube was included which was kept in the dark. After subjecting the tubes to different conditions like thermal stress or exposure to 690 nM laser light for different time intervals, polyacylamide Gel electrophoresis radioradiography was used to monitor the effect of heat as well as light on the oligo labeled sensitizer beads. Aliquots (5 uL) of beads subjected to various conditions (thermal stress or 680 nm laser) were removed and mixed with 5 uL of formamide loading buffer (80% (v/v) formamide, 50 mM Tris-borate (pH 8.3, 1 mM EDTA, 0.1% (w/v) xylene cyanol, and 0.1% (w/v) bromphenol blue). Typically 20% PAGE gels were prepared form 40% (w/v) ready-to-use solution of acrylamide (38%) and bisacrylamide (2%) from Amersco, 8 M urea (Gibco BRL) and 1×TBE buffer made from 10×TBE solution (BioWhittaker). For DNA molecular weight size markers, Msp I digent of pBR322 (New England Biolabs) was labeled with gamma $^{32}$P ATP was used. All manuipulations of the beads including running the PAGE gel were done in the dark. Electrophoresis was carried out until the tracking dyes had migrated a suitable distance (Maniatis et al. 1982). Gels were exposed for 24 hours onto Kodak X-Omat® AR X-ray film with Cronex Lighting Plus intensifying screen (DuPont) at −70° C. The release of intact full length oligo from the beads show up as 40 or 24 base bands on the gels.

Example 12

Reversible Quenching of Coumarin Fluorescence

Figure 13A:
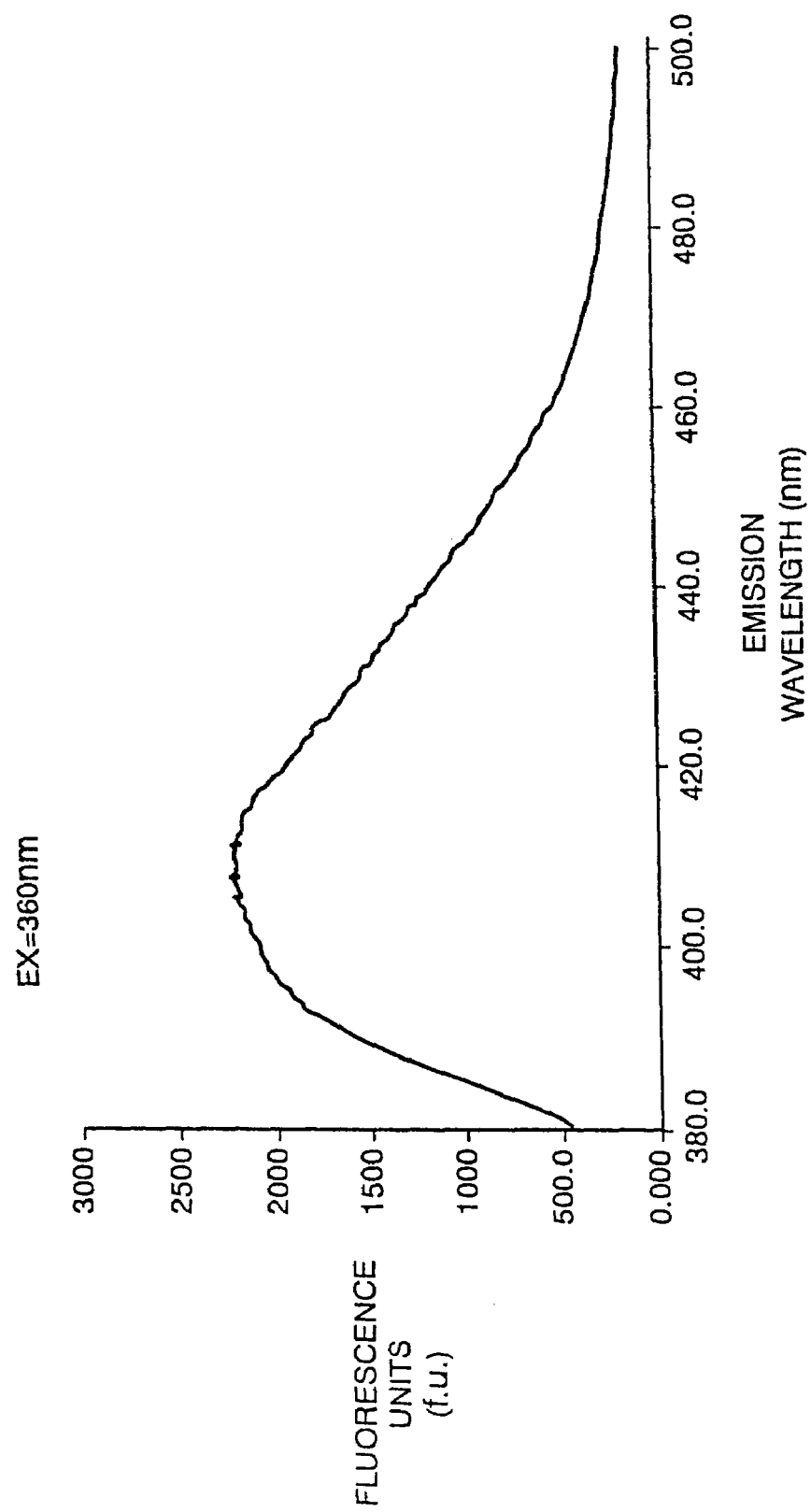
FIG. 13 illustrates (a) fluorescence spectra for coumarin-1; (b) fluorescence spectra for coumarin-1 measured at excitation wavelength of 360 nm; and (c) represents a fluorescence profile following generation of singlet oxygen by activating the sensitizer by irradiation (Example 12).

Coumarin-1 (Kodak Chemicals Inc.) was brought to 0.1 uM in toluene. The coumarin solution was then excited with light at 360 nm and fluorescence was measure in the range of 380 nm to 500 nm as shown in FIG. 13A. Peak fluorescence was seen at about 410 nm.

Bis-phenyl pyrazine was prepared by heating at 130° C. for 12 hrs a suspension of benzoin (Aldrich, 1.25 g) and 1,2 dianilinoethane (Aldrich, 2.13 g) in xylene (20 ml). The mixture was cooled to room temperature and was purified by column chromatography (silicagel, hexane:ethyl acetate, 95:5) to give 2.2 grams of pure bis-phenyl pyrazine as pale yellow solid. NMR: (CDCl$_3$) 7.2-6.8 (20H, m) and 3.6 (4H, s).

Figure 13B:
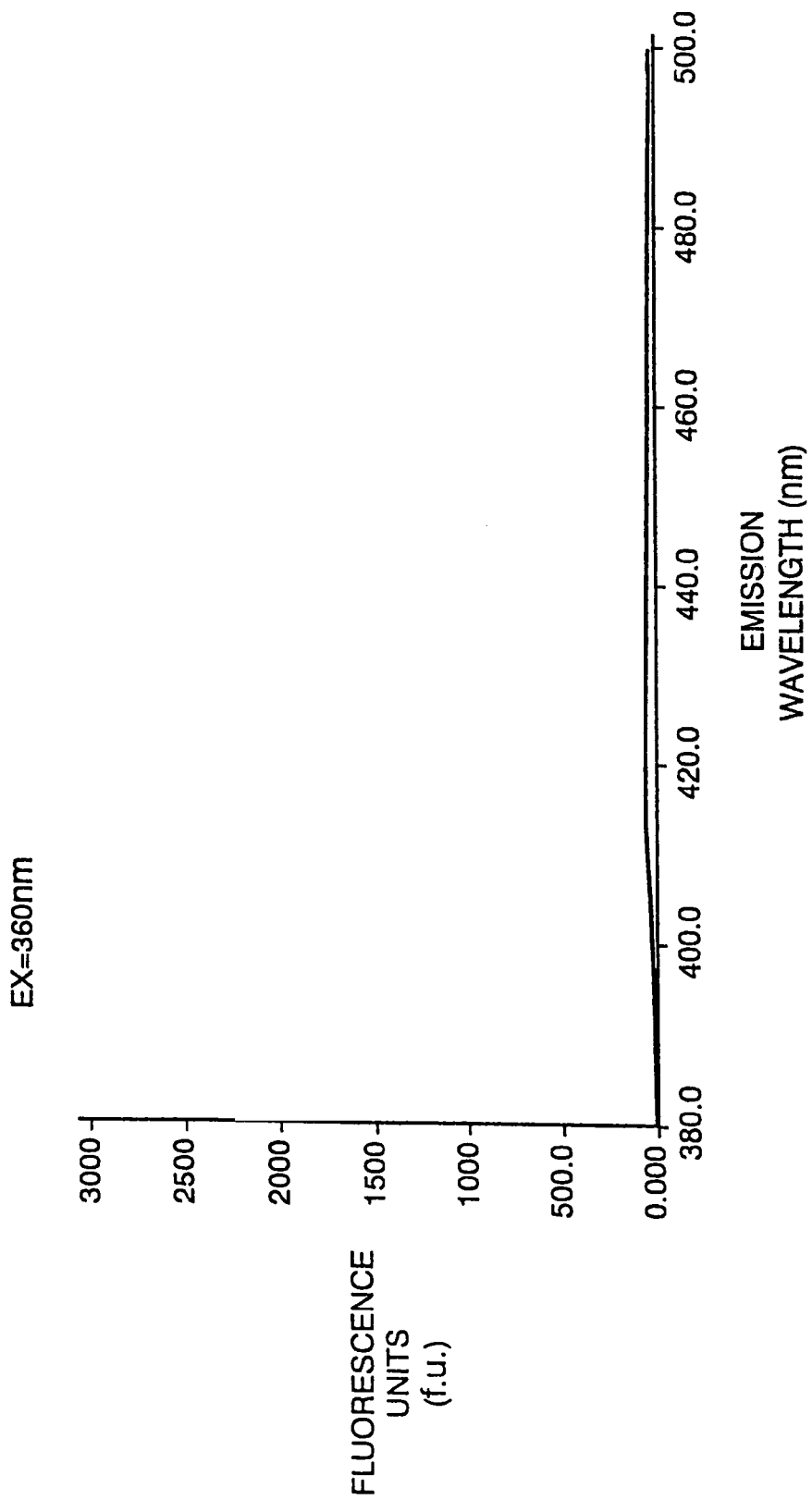

Bis N-phenyl pyrazine was added to 2 ug/ml of the coumarin solution. The coumarin solution was then excited with light at 360 nm and fluorescence was measure in the range of 380 nm to 500 nm as shown in FIG. 13B. The very low fluorescence indicates that the fluorescence of coumarin was effectively quenched by bis N-phenyl pyrazine.

A solution of coumarin 1 (Aldrich, 0.1 uM in toluene, 0.5 ml), bis diphenyl pyrazine (2 ug/ml in toluene, 50 uL) and the photosensitizer silicon phthalocyanine (1.0 uM in toluene, 1 uL) were mixed in a cuvette. The mixture was irradiated with a Dolan Jenner lamp using a 610 nm cutoff filter. The aliquots were taken at different time and the fluorescence of the samples were measured at excitation wavelength of 360 nm.

Figure 13C:
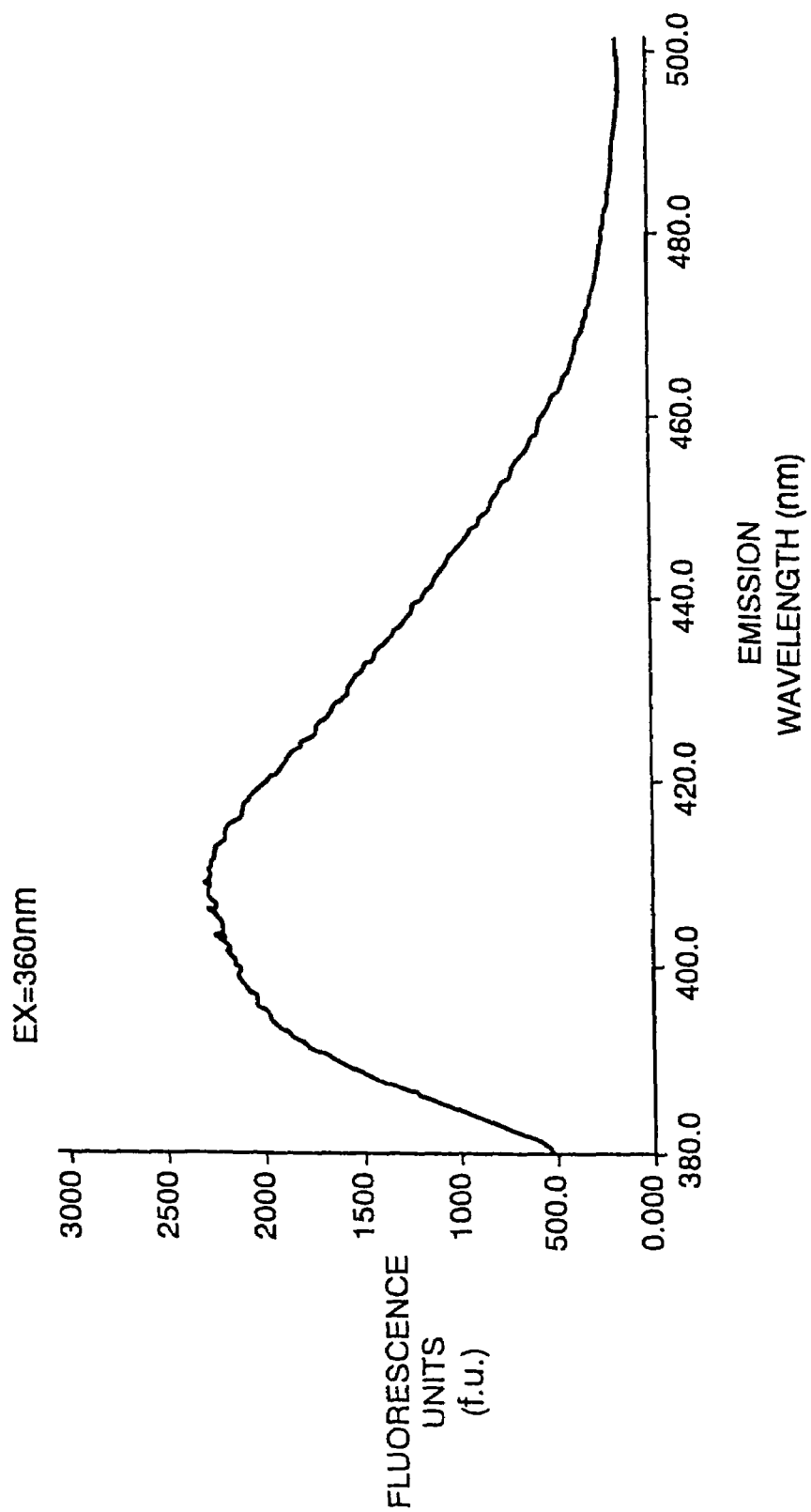
Figure 14:
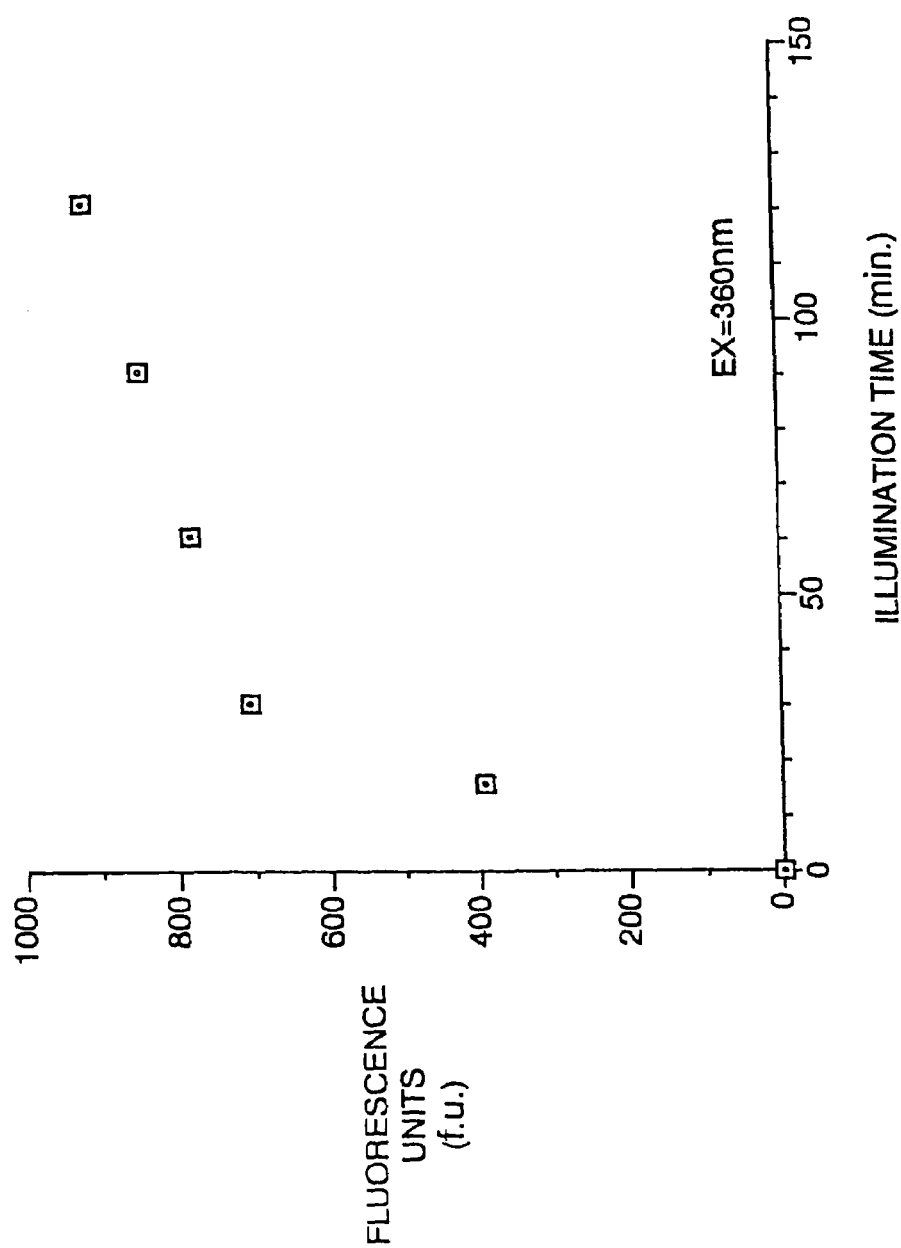
FIG. 14 illustrates the increasing fluorescence at 412 nm of reaction mixtures after increasing irradiation times of the senstizer (Example 12).

As shown in FIG. 13C, after generation of singlet oxygen by activating the sensitizer by irradiation, a fluorescence profile was generated that was very similar to the profile of the unquenched coumarin. FIG. 14 and the following table illustrate the increasing fluorescence at 412 nm of the above reaction mixture after increasing times of irradiation of the sensitizer.

| Time (minutes) | FU (at 412 nm)* |
|---|---|
| 0 | 0 |
| 15 | 400 |
| 30 | 700 |
| 60 | 800 |
| 90 | 850 |
| 120 | 870 |

*background fluorescence was subtracted from measurements

Example 13

Synthesis of Thioxene-BPEA(21):

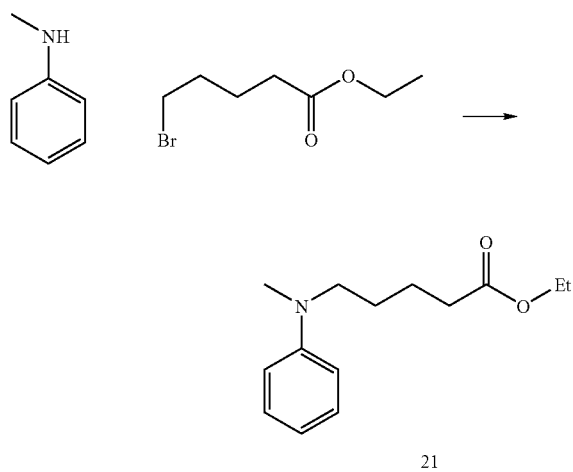

To a 250 ml, 3-necked round bottom flask equipped with a water condenser, a mechanical stirrer, and a thermometer was added 62 g of N-methyl aniline (0.58 mole) and 62 g of ethyl 5-bromovalerate (0.3 mole). The reaction mixture was heated to 100° C. for 16 hours. The brown reaction mixture was cooled to room temperature and poured into 100 ml of ethyl acetate. The ethyl acetate solution was washed with 20% sodium hydroxide (3×100 ml). The aqueous layer was extracted with 50 ml of ethyl acetate. The combined ethyl acetate solution was dried over sodium sulfate (50 g). The ethyl acetate was filtered through a glass funnel equipped with a cotton plug and the filtrate was concentrated under reduced pressure (30 mm Hg, 40° C. rotavap). The brown residue was distilled under vacuum (130-137° C. 0.5 mm Hg) to yield 60 g of compound 21 (86%) as a colorless liquid. $^1$H NMR (CDCl$_3$, 250 MHz): δ 1.3 (t, 3H), 1.65 (m, 4H), 2.3 (t, 2H), 2.8 (s, 3H), 3.3 (t, 2H), 4.2 (q, 2H), 6.65 (Q, 2H), 7.2 (m, 3H).

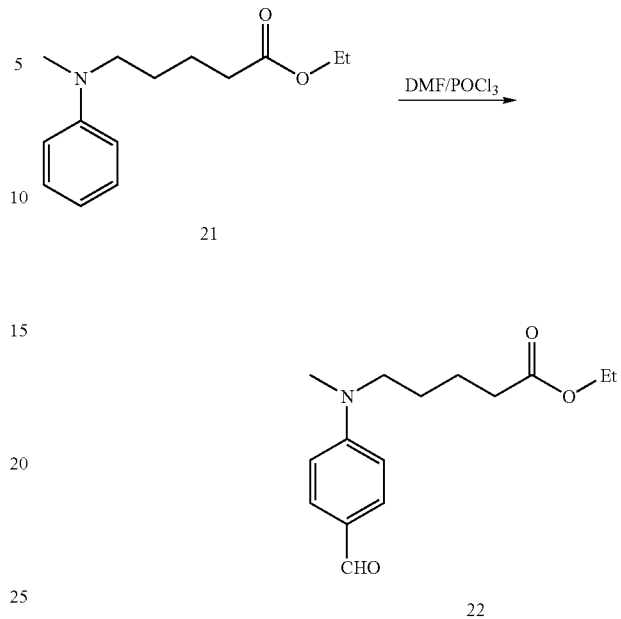

A 3-necked, round bottom flask equipped with a condenser, a 25-ml dropping funnel, and a stir bar was placed in an ice bath on a magnetic stirrer. DMF (8.8 g) was added and stirred until the temperature dropped to 4° C. POCl$_3$ (5.06 g) was added dropwise from the dropping funnel over a period of 10 minutes. After the addition was completed, the reaction was stirred at 4° C. for 10 minutes. Compound 21 (3.76 g) was added rapidly in less than 1 minute and the reaction was heated at 100° C. for 1 hour. The reaction mixture was poured into ice and neutralized with 20% sodium hydroxide. The mixture was extracted with ethyl acetate (3×50 ml). The combined ethyl acetate solution was dried over sodium sulfate (50 g). The organic phase was filtered through a glass funnel equipped with a cotton plug and the filtrate was concentrated under reduced pressure (30 mm Hg, 40° C. rotavap). The residue was chromatographed on a silica gel column (CH$_2$Cl$_2$ to CH$_2$Cl$_2$:EtOAc 9:2) to give pure compound 22 as a yellow liquid.

$^1$H NMR (CDCl$_3$, 250 MHz): δ 1.2(t, 2H), 1.6 (m, 4H), 2.3 (t, 2H), 2.9 (s, 3H), 3.3 (t, 2H), 4.1 (q, 2H), 6.6 (q, 2H), 7.6 (q, 2H), 9.7 (s, 1H).

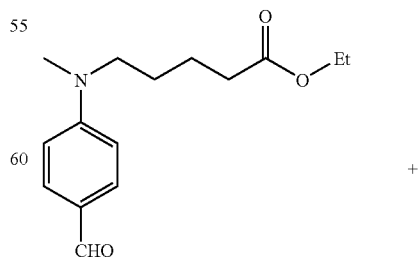

+

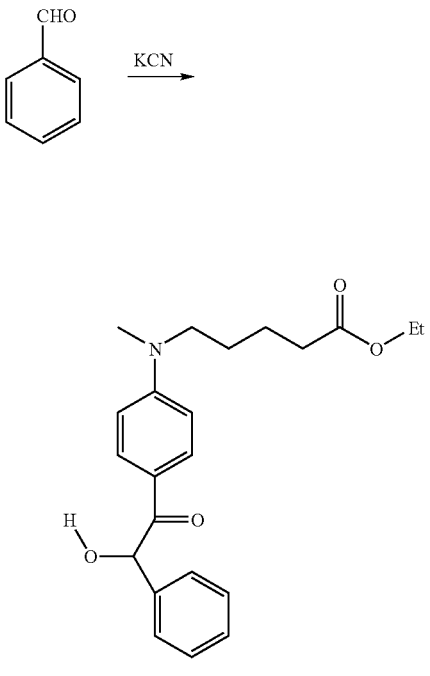

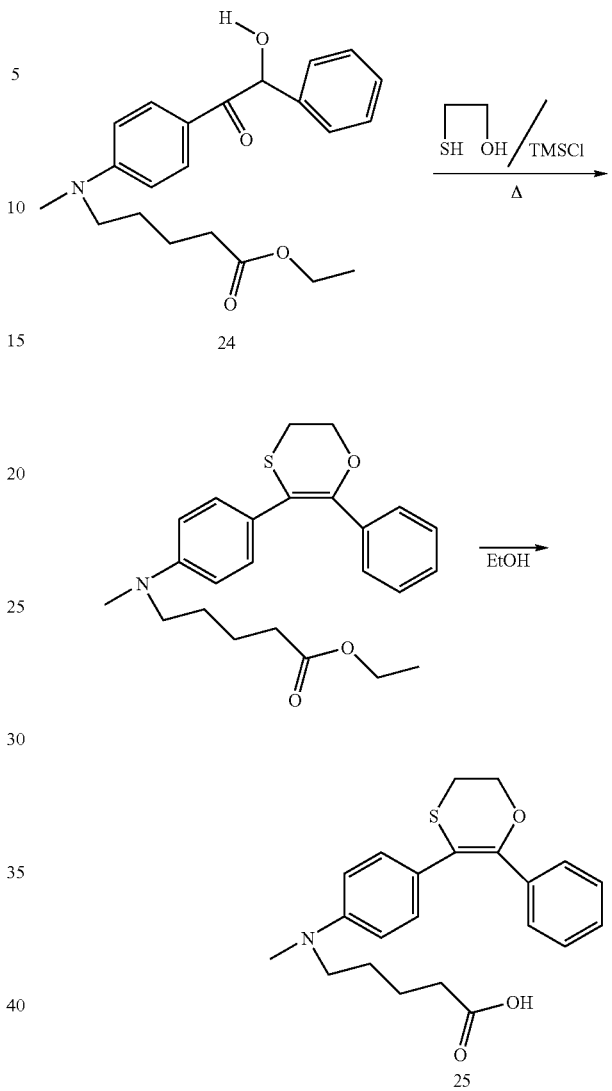

To a 250 ml, 3 necked round bottom flask equipped with a water condenser, a mechanical stirrer and a thermometer was added 5.0 g of 22 (20 mmol) and 2 g of potassium cyanide in 60% ethanol under argon. The reaction mixture was placed in an oil bath and refluxed. To the refluxing reaction mixture 2.15 g of benzaldehyde (20 mmol) in 20 ml of ethanol was added during 90 minutes. The reaction mixture was refluxed for 15 minutes more and extracted with ethyl acetate (3×50 ml). The combined ethyl acetate solution was dried over sodium sulfate (50 g). The organic phase was filtered through a glass funnel equipped with a cotton plug, and the filtrate was concentrated under reduced pressure (30 mm Hg, 40° C. rotavap). The crude residue was dissolved in 25 ml of dry ethanol, and 0.5 ml of trimethylsilyl chloride was added. The reaction mixture was stirred overnight at room temperature and then poured into a mixture of 150 ml of saturated aqueous sodium bicarbonate and 50 ml of methylene chloride. The organic layer was separated and washed with 100 ml of saturated sodium bicarbonate solution. The combined aqueous layer was extracted with 75 ml of $CH_2Cl_2$. The combined organic solution was dried over sodium sulfate (50 g), filtered through a glass funnel equipped with a cotton plug, and the filtrate was concentrated under reduced pressure (30 mm Hg, 40° C. rotavap). The product was purified on preparative TLC (hexane:ethyl acetate 5:1) to yield 2.2 g of the substituted benzoin 23.

$^1$H NMR (CDCl$_3$, 250 MHz): δ 1.3 (t, 3H), 1.6 (m, 4H), 2.4 (t, 2H), 2.9 (s, 3H), 3.3 (t, 2H), 4.1 (q, 2H), 4.8 (q, 1H), 5.8 (q, 1H), 6.5 (q, 2H), 7.3 (m, 5H), 7.8 (q, 2H).

A solution of the benzoin 24 (1.50 g, 4 mmol) in toluene (40 ml) was treated with 2-mercapto ethanol (3.17 g, 40 mmol) and TMSCl (1.3 g, 12 mmol) was refluxed for 18 hours. The mixture was then cooled down to room temperature and added to ether (200 ml). The ether phase was extracted with 10% $Na_2CO_3$ solution (2×100 ml) and water (100 ml) and dried ($Na_2SO_4$). The ether phase was concentrated to a yellow oil that was purified on a silica gel column (hexane: $CH_2Cl_2$ 90:10) to give 280 mg of the thioxene as a pale yellow oil.

The thioxene (80 mg, 0.2 mmol) was dissolved in EtOH (3 ml) and NaOH (1 ml of 0.1 M) was added. The mixture was heated at 80° C. overnight. The mixture was neutralized by addition of $NaH_2PO_4$ (2.0 g) and extracted with 2×100 ml of $CH_2Cl_2$. The combined organic layer was dried ($Na_2SO_4$). The organic layer was concentrated under vacuum and the remaining oil was purified by PTLC (silca gel, $CH_2Cl_2$: MeOH 95:5) to give approximately 60 mg of the acid 25.

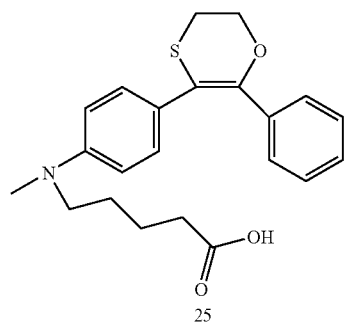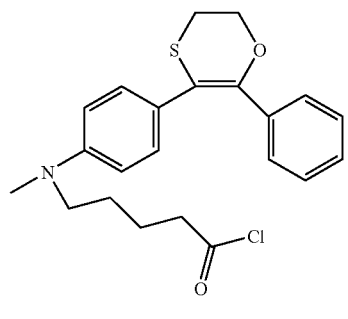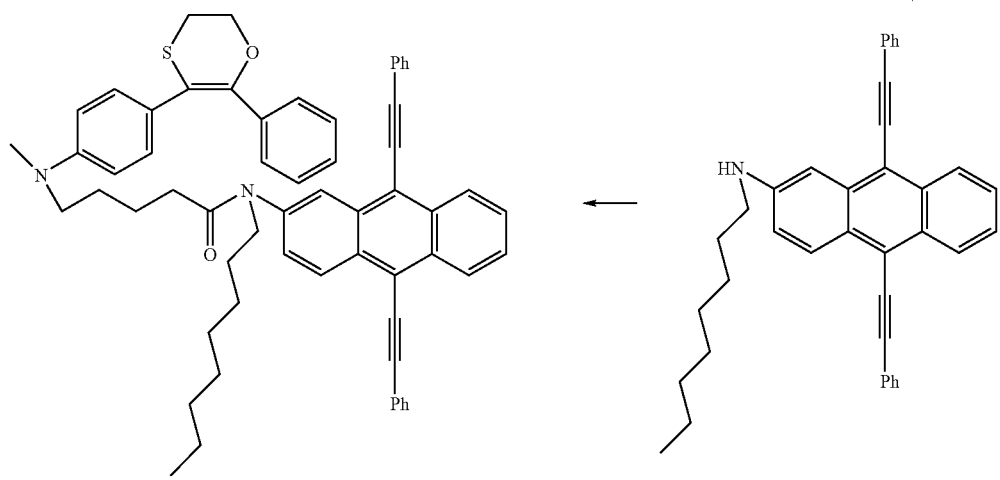

The acid 25 (120 mg 0.5 mmol) in 5.0 ml of THF was cooled in an ice bath for 30 minute and 5.0 ml of oxalyl chloride was added to the cooled solution. The reaction mixture was stirred at 4° C. for 3 hours. Excess oxalyl chloride was removed on the rotavap under reduced pressure.

Preparation of 2-amino octyl 9,10 bis-(phenyl ethynyl) anthracene (26)

To a solution of 2-amino 9,10 bis-phenyl ethynyl anthracene (Aldrich, 1.0 mmol) in anhydrous DMF (2 ml) was added octyl bromide (Aldrich, 1.1 mmol) and triethyl amine (1.3 mmol). The mixture was heated to 140° C. overnight. The reaction was cooled to room temperature and evaporated to dryness. The residue was dissolved in THF and purified on a PTLC (silica gel, ethyl acetate:hexane, 50:50) to give the product (compound 26) as an orange solid in 50% yield.

This compound in 25 ml of dry THF was add ed to the residue product of the reaction of compound 25 with oxalyl chloride, followed by 2 drops of triethyl amine. The heterogenous reaction mixture was stirred at room temperature for 24 hours. The reaction mixture was worked up by addition of the above mixture to brine (50 mL). The mixture was then extracted with ethyl acetate (3×50 mL). The combined organic phase was dried ($Na_2SO_4$) and evaporated to dryness to give a dark brown oil. The product, thioxene linked BPEA, compound 27, was purified on preparative TLC ($CH_2Cl_2$: hexane 9:1) to yield 150 mg of yellow glassy solid. $^1H$ NMR ($CDCl_3$, 250 MHz):δ 1.6 (m, 6H), 2.5 (t, 2H), 2.9 (s, 3H), 3.3 (q, q, 2H), 3.45 (t, 2H), 4.5 (q, q 2H), 6.55 (q, 2H), 7.0 (q, 2H), 7.2 (m, 5H), and 7.7 (m, 15H). Mass Spectrum (CI: m/e, relative intensity) $M^+758$ (100). Absorption Spectra (Toluene): 330 nm ($\epsilon$: 13,000), 448 nm, 476 nm ($\epsilon$: 32,000).

Example 14

Method for Preparing Components of FOCI Nucleic Acid Detection System

All reagents were reagent grade and were used without further purification. Aqueous solutions used for nucleic acid detection were 0.2 micron filtered. UV spectra were run on a Hewlett Packard model 8452A Diode Array Spectrophotometer. Fluorescence measurements were made on a Hitachi F-4500 Fluorescence Spectrophotometer. Particle sizing was run on a NICOMP Submicron Particle Sizer, Model 370. Ultracentrifigation was done on a Du Pont Instruments Sorvall RC 5B Refrigerated Superspeed Centrifuge or an Eppendorf model 5415C or 5417C. Where appropriate, reactions were run under an argon atmosphere. All potentially light sensitive reactions were wrapped in foil to exclude light. Generally, after each addition the contents of each tube were mixed by vortexing. None of the reactions were optimized.

Coating Buffer: 0.2 M MES pH 6.0
Reducing Buffer: 3.5 M NaOAc pH 5.3
Pre-coupling Buffer: 5 mM $Na_2HPO_4$, 2 mM EDTA, pH 6
Coupling Buffer: 0.1 M borate, 0.64 M $Na_2SO_4$, 0.58 mM EDTA, pH 9.5

Blocking Buffer: 0.1 M NaCl, 0.17 M glycine, 10 mg/mL BSA, 0.1% Tween-20, 1 mM EDTA, 50 uL/mL calf thymus DNA, pH 9.2

LOCI Buffer: 0.1 M Tris base, 0.3 M NaCl, 0.025 M EDTA, 1 mg/mL Dextran T-500, 1 mg/mL BSA (RIA gade), 1/320 dilution HBR-1, 0.05% Kathon, 0.01% Gentamicin, pH 8.3

Pre-stressing Buffer: Std. LOCI buffer, 10 mM Bis-tris propane, pH 9.2

Storage Buffer: 50 mM KCl, 10 mM Tris, 4 mM EDTA, 0.02% Ac-BSA, pH 8.2

In House Buffer (IHBB): 40 mM Tris pH 8.0, 4 mM $MgCl_2$, 70 mM KCl, 200 ug/mL Ac-BSA Preparation of Thioxene-BPEA Dyed Acceptor Beads:

Seradyn beads (2.5 mL, 100 mg/mL, 203 nm, carboxy coated) were combined with 4.75 mL ethylene glycol, 2.5 nL ethoxyethanol, and 0.25 mL 0.10 N NaOH. This bead suspension was dispensed into four glass tubes (2.0 mL each). Separately, 10.0, 5.0, 1.0, and zero mg portions of thioxene-linked-BPEA (T-BPEA) were each dissolved in 1.00 mL of ethoxyethanol. After the eight tubes were equilibrated for 5 min at 95° C., the 1 mL dye solutions were rapidly added and mixed with the appropriately marked 2 mL bead suspensions. Intermittent mixing was continued for 15 min at 95° C. After cooling, each loading of dyed beads was transferred with 4 mL ethanol to 10 cc Oakridge centrifuge tubes. The beads were compacted by centrifugation (1 hr, 16,000 rpm), and each re-suspended in 4 mL 50% ethanol/water. Following a second centrifugation and resuspension of each in 2.0 mL 10% ethanol water, the beads were subjected to a slow spin (5 min, 2.5 K rpm) and decanted from free dye. These bead suspensions were stored at 4° C.

Preparation of BrAc Dextran/EDAC Coated T-BPEA Acceptor Beads:

A portion (1.0 mL) of each respective dye loaded bead suspension was added to each of four vortexed tubes containing 1 mL 6 mg/mL solutions of bromo acetyl-dextran ("BrAc-dextran") in coating buffer. 1-Ethyl-3-(3-dimethylaminopropyl)carbodiimide ("EDAC") (0.25 mL, 10 mg/mL water) was added while vortexing. After mixing (shaker table) for 16 h at ambient temperature, each set of beads was diluted with 5 mL water, compacted by centrifuge, and re-suspended in 5 mL 0.5 M NaCl. After washing each twice with 5 mL water, the beads were finally re-suspended in 0.95 mL water. A final compaction of aliquots from these bead suspensions was done just prior to coupling with oligo.

Preparation of Sulfo-SMCC/EDAC Coated Phthalocyaninine Sensitizer Beads:

This section describes preparation of an amino dextran maleimid (MAD) for the attachment of oligos, similar to the BrAC dextran coated bead preparation. The procedure for preparation of silicon tetra-t-butyl phthalocyanine, phthalocyanine sensitizer beads, and hydroxypropylaminodextran coated sensitizer beads are described in Example 5. Sulfo-Succinimidyl-4-(N-Maleimidomethyl) ("sulfo-SMCC") (11.55 mg) was dissolved in 0.5 mL distilled water. Slowly, during 10 sec, the above solution was added to 5 mL of stirring aminodextran (Molecular Probes, Eugene, Oreg.) solution (12.5 mg/mL in 50 mM MOPS, pH 7.2), The mixture was incubated for 1 hr at room temperature.

To the stirring solution above was added 5 mL of 20 mg/mL (100 mg) of the sensitizer beads in distilled water. Then, 1 mL of 200 mg/mL NHS (prepared fresh in 50 mM MES, pH adjusted to 6.0 with 6 N NaOH), 200 mg EDAC was dissolved in 1 mL distilled water and this solution was added slowly with stirring to the sensitizer beads. The pH was adjusted to 6.0 by addition of 450 µL of 1N HCl and the mixture was incubated overnight in the dark. A solution of 100 mg of succinic anhydride in 0.5 mL of DMSO was added to the sensitizer beads and the mixture was incubated for 30 min at room temperature in the dark. To this mixture was added 0.13 mL 10% Tween-20 bringing the final concentration of Tween-20 to 0.1%. The beads were centrifuged for 45 min at 15,000 rpm. The supernatant was discarded and the beads were resuspended in 10 mL of buffer (50 mM MOPS, 50 mM EDTA and 0.1% Tween-20, pH 7.2). The mixture was sonicated to disperse the beads. The beads were centrifuged for 30 min as described above; the supernatant was discarded and the beads were resuspended. This procedure was repeated twice. Then, the beads were resuspended to 40 mg/mL in 2.5 mL of the above buffer, saturated with argon and Tween-20 was added to a concentration of 0.1%. The beads were stored at 4° C.

Preparation of Oligo for Coupling to T-BPEA Dyed Beads:

To 215 uL of 0.8 mM disulfide modified oligo 5'$(AGTA)_6$(C-3SS)3' (SEQ ID NO:4) contained in a 1 cc Eppendorf tube, was added 17 uL reducing buffer and 41 uL tris carboxyethyl phosphine (TCEP), 20 mM in water. The solution was mixed for 1 h at ambient temperature. Four volumes of −20° C. ethanol were added and the mixture was cooled at −20° C. for 2 h. Following centrifugation, the pellet was re-suspended in 0.25 mL ethanol and re-compacted. The pellet was finally redissolved in 126 uL of pre-coupling buffer.

Coupling of Oligo to T-BPEA Dyed Beads:

To four 1 cc Eppendorf tubes each containing 4 mg of the various T-BPEA dye loaded and coated beads, was added 29 uL of the oligo solution. Coupling buffer (88 uL) and 1% Tween-20 (3.3 ul) was added to each tube. Following overnight incubation under argon at 37° C., 14 uL of 0.1 M sodium thioglycolic acid was added and the mixture was incubated at 37° C. for one additional hour. The cooled beads were compacted and each was washed twice with 1.0 mL water, and re-suspended in 1.0 mL blocking buffer. Each dye loading of beads was again washed with 1.0 mL water, re-suspended in 1.0 mL prestressing buffer, and incubated for 1.5 h at 95° C. under argon. After cooling, the beads were washed twice with 1.0 mL water, once with 0.5 mL storage buffer, and re-suspended in 0.40 mL storage buffer to give ca. 10 mg/mL of each dye loading of coated oligo beads. For T-BPEA beads the individual oligo loadings were calculated following fluorescence depletion analysis using complimentary fluorescein-$(TACT)_{10}$ (SEQ ID NO:5) (and non-complimentary fluorescein-$(TATC)_{10}$ (SEQ ID NO:6) fluorescent probes. The complimentary probes revealed oligo loadings of 4.5K, 3.4K, 2.4K, and 3.6K oligos/bead respectively for the zero, 20, 100, and 200 mM theoretical dye loaded beads. A crude calculation from UV indicated that the actual dye loadings were about 50% of theory. The non-complimentary probes were not depleted.

Preparation of Oligo for Coupling to Sensitizer Beads

To a solution of disulfide modifed oligo $d(A)_{24}$ (SEQ ID NO: 1) (220 µl 0.9 mM in water), was added 18 µl of reducting buffer and 43 µl of TCEP (20 mM, in water). The solution mixture was mixed for one hour at ambient temperature and the procedure for the preparation of oligo for coupling to T-BPEA dyed beads was followed. The pellet was finally redissolved in 126 µL of coupling buffer.

Coupling of Oligo to Sensitizer Dyed Beads:

To the previously described sensitizer dyed MAD coated beads (1 mL of 4 mg/mL in 50 mM MOPS, 50 mM EDTA and 0.1% Tween-20, pH 7.2) was added 30 μl of the oligo solution and essentially the procedure for coupling of oligo to T-BPEA dyed beads was followed.

Example 15

FOCI Nucleic Acid Detection Assay

Referring to FIG. 15, this specific example of the FOCI nucleic acid detection assay of the present invention utilizes the ability of Thioxene-BPEA to be unquenched by reaction with singlet oxygen.

Figure 16:
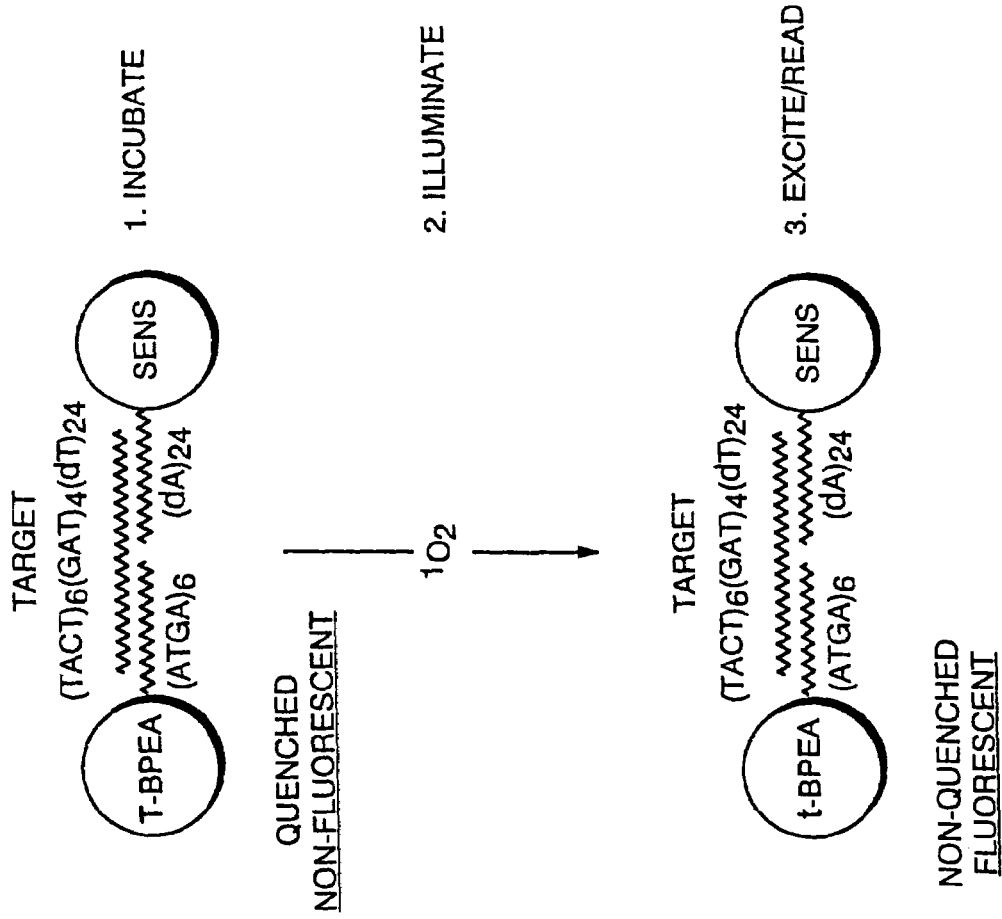
FIG. 16 illustrates the FOCI nucleic acid procedure (Example 15).
Figure 17:
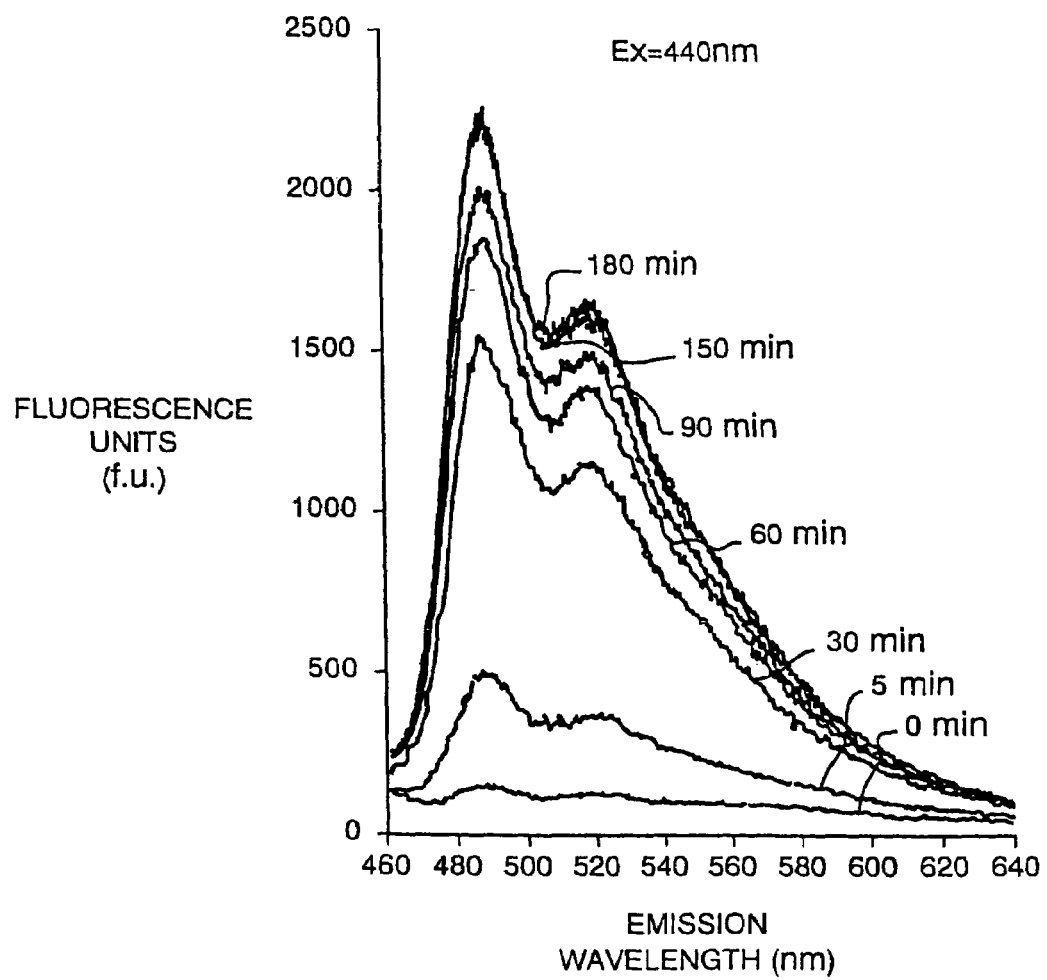
FIG. 17 illustrates the fluorescence profile after illumination with varying illumination times (Example 15).
Figure 18:
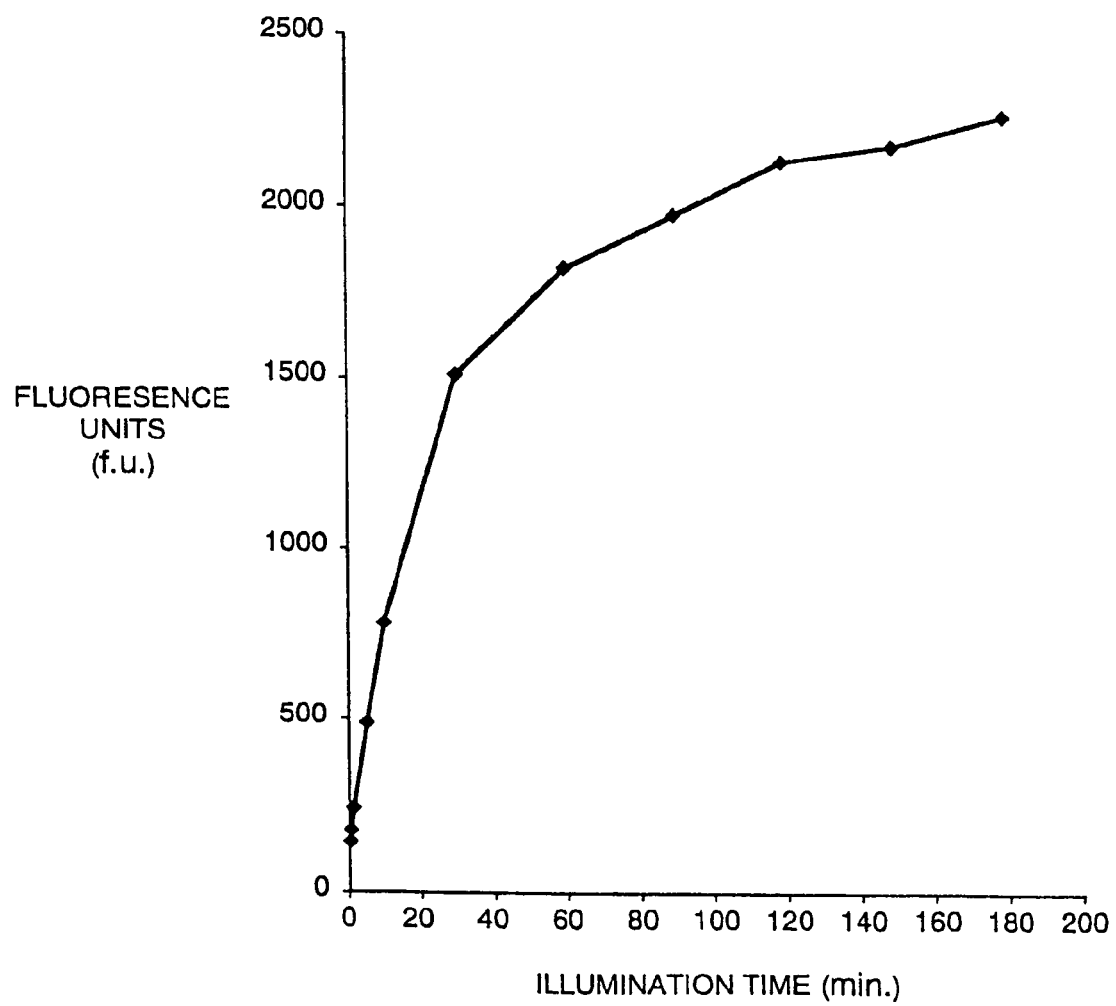
FIG. 18 illustrates the increasing fluorescence of reaction mixtures after increasing irradiation times (Example 15).

Referring to FIG. 16, a portion (150 ug in 0.75 mL IHBB) of the ca. 100 mM T-BPEA dye loaded oligo beads were combined with tetra-t-butyl(trihexylsilyl) silicon phthalocyanine-dA$_{24}$ (SEQ ID NO:1) sensitizer beads (150 ug in 0.75 mL IHBB) and 30 uL of 500 nM target oligonucleotide (TACT)$_6$(GAT)$_4$T$_{24}$ (SEQ ID NO:2) (10 nM per 1.5 mL assay). The assay suspension was incubated for 1 h at 37° C. Illumination of a 10 fold diluted aliquot for increasing times using a Dolen-Jenner lamp with a 610 nm cut off filter, resulted in corresponding increases of fluorescence following excitation at 440 nm (see FIGS. 16 and 17, and table 1). Increased fluorescence at 30 seconds of illumination could be detected. Following irradiation for 180 min, fluorescence was not significantly increased with further irradiation for 30 min in the presence of 150 uL of 10 uM methylene blue.

TABLE 1

Fluorescence after illumination with varying illumination times

| Illumination Time (min) | Fluorescence Intensity (f.u.) at 480 nm |
|---|---|
| 0 | 138.135 |
| 0.5 | 171.01 |
| 1 | 217.899 |
| 5 | 374.934 |
| 10 | 626.741 |
| 30 | 1178.251 |
| 60 | 1438.015 |
| 90 | 1593.165 |
| 120 | 1699.709 |

TABLE 1-continued

Fluorescence after illumination with varying illumination times

| Illumination Time (min) | Fluorescence Intensity (f.u.) at 480 nm |
|---|---|
| 150 | 1714.496 |
| 180 | 1727.793 |

Detection Limit:

Using the same beads as above, each of seven tubes containing 100 uL (20 ug) T-BPEA beads and 100 uL (20 ug) sensitizer beads were treated with 8 uL of series 10 fold dilutions of target oligo (SEQ ID NO:2). The tubes were incubated for 2 h at 55° C. The contents of each tube was diluted 10 fold with IHBB and tested for fluorescence after illumination (dolen-Jenner lamp with a 610 nm cutoff filter) 10 min (T$_{10}$) versus no illumination (T$_0$). A zero target control was used for comparison. The three highest serial 10 fold dilutions (1.25 nM, 125 pM, and 12.5 pM) could be readily detected. The fourth 10 fold dilution (1.25 pM) could not be readily detected by fluorescene (see Table 2).

TABLE 2

Fluorescence after illumination with varying amounts of target oligonucleotide

| Concentration of Target | Illumination Time (min) | Fluorescence Intensity (f.u.) at 480 nm |
|---|---|---|
| 0 | 10 | 165.046 |
| 1.25 pM | 10 | 168.772 |
| 12.5 pM | 10 | 224.060 |
| 125 pM | 10 | 527.487 |
| 1.25 nM | 10 | 671.327 |
| 1.25 pM | 0 | 171.556 |
| 12.5 pM | 0 | 169.998 |
| 125 pM | 0 | 159.460 |
| 1.25 nM | 0 | 141.973 |

Although the foregoing invention has been described in some detail by way of illustration and example for purposes of clarity and understanding, it will be obvious that certain changes or modifications may be practiced within the scope of the appended claims.

We claim:

1. A method for determining the presence or concentration of an analyte in a medium, said method comprising:

providing a reaction mixture comprising in combination:
- a medium suspected of containing an analyte;
- a first specific binding pair member bound to a water-insoluble solid support;
- a second specific binding pair member bound to a sensitizer, said sensitizer capable in its excited state of generating a reactive oxygen species, wherein the proximity of the first specific binding pair member with the second specific binding pair member is modulated by the presence of the analyte; and
- digoxigenin-linked biotin linked to the solid support through a reactive oxygen cleavable linker;

incubating the reaction mixture;

exciting the sensitizer, said excitation of the sensitizer causing the formation of reactive oxygen, which cleaves the cleavable linker and releases digoxigenin-linked biotin from the solid support; and detecting the released digoxigenin-linked biotin, the amount thereof being related to the amount of analyte in said medium.

2. The method of claim 1 wherein:

the proximity of the first and second specific binding pair members to one another results from the binding of the first and second specific binding pair members to the analyte;

the sensitizer is a photosensitizer;

the reactive oxygen species is singlet oxygen; and the excitation step comprises irradiation of the photosensitizer with light.

3. The method of claim 1 wherein:

the step of detecting the released digoxigenin-linked biotin is carried out by a detection method employing, as a third specific binding pair member, avidin bound to a member of a signal producing system or anti-digoxigenin antibodies bound to a member of a signal producing system or both.

* * * * *

UNITED STATES PATENT AND TRADEMARK OFFICE
CERTIFICATE OF CORRECTION

| | | |
|---|---|---|
| PATENT NO. | : 7,635,571 B2 | Page 1 of 1 |
| APPLICATION NO. | : 09/732047 | |
| DATED | : December 22, 2009 | |
| INVENTOR(S) | : Ullman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1648 days.

Signed and Sealed this

Ninth Day of November, 2010

David J. Kappos
*Director of the United States Patent and Trademark Office*

SEQUENCE LISTING

<160> NUMBER OF SEQ ID NOS: 7

<210> SEQ ID NO 1
<211> LENGTH: 24
<212> TYPE: DNA
<213> ORGANISM: Artificial Sequence
<220> FEATURE:
<223> OTHER INFORMATION: hybridization oligo

<400> SEQUENCE: 1
aaaaaaaaaa aaaaaaaaaa aaaa                                    24

```
<210> SEQ ID NO 2
<211> LENGTH: 60
<212> TYPE: DNA
<213> ORGANISM: Artificial Sequence
<220> FEATURE:
<223> OTHER INFORMATION: hybridization oligo

<400> SEQUENCE: 2
tacttactta cttacttact tactgatgat gatgattttt tttttttttt tttttttttt      60

<210> SEQ ID NO 3
<211> LENGTH: 24
<212> TYPE: DNA
<213> ORGANISM: Artificial Sequence
<220> FEATURE:
<223> OTHER INFORMATION: hybridization oligo

<400> SEQUENCE: 3
agtaagtaag taagtaagta agta                                            24

<210> SEQ ID NO 4
<211> LENGTH: 25
<212> TYPE: DNA
<213> ORGANISM: Artificial Sequence
<220> FEATURE:
<223> OTHER INFORMATION: hybridization oligo

<400> SEQUENCE: 4
agtaagtaag taagtaagta agtac                                           25

<210> SEQ ID NO 5
<211> LENGTH: 40
<212> TYPE: DNA
<213> ORGANISM: Artificial Sequence
<220> FEATURE:
<223> OTHER INFORMATION: hybridization oligo

<400> SEQUENCE: 5
tacttactta cttacttact tacttactta cttacttact                           40

<210> SEQ ID NO 6
<211> LENGTH: 40
<212> TYPE: DNA
<213> ORGANISM: Artificial Sequence
<220> FEATURE:
<223> OTHER INFORMATION: hybridization oligo

<400> SEQUENCE: 6
tatctatcta tctatctatc tatctatcta tctatctatc                           40

<210> SEQ ID NO 7
<211> LENGTH: 40
<212> TYPE: DNA
<213> ORGANISM: Artificial Sequence
<220> FEATURE:
<223> OTHER INFORMATION: hybridization oligo

<400> SEQUENCE: 7
aaaaaaaaaa aaaaaaaaaa aaaaaaaaaa aaaaaaaaaa                           40
```